(12) United States Patent
Bangera et al.

(10) Patent No.: US 8,073,632 B2
(45) Date of Patent: Dec. 6, 2011

(54) COMPUTATIONAL METHODS AND SYSTEMS FOR TREATMENT IN RELATION TO MODULATION OF CYP450 ENZYME ACTIVITY

(75) Inventors: Mahalaxmi Gita Bangera, Renton, WA (US); Roderick A. Hyde, Redmond, WA (US); Muriel Y. Ishikawa, Livermore, CA (US); Elizabeth A. Sweeney, Seattle, WA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 528 days.

(21) Appl. No.: 12/319,153

(22) Filed: Dec. 30, 2008

(65) Prior Publication Data
US 2010/0169022 A1 Jul. 1, 2010

Related U.S. Application Data

(63) Continuation-in-part of application No. 12/319,154, filed on Dec. 30, 2008.

(51) Int. Cl.
*G06F 19/00* (2011.01)
(52) U.S. Cl. ...................................... 702/19; 435/288.4
(58) Field of Classification Search ............... 702/19, 702/182–185; 435/288.4
See application file for complete search history.

(56) References Cited

U.S. PATENT DOCUMENTS

| | | |
|---|---|---|
| 5,658,881 A | 8/1997 | Gelland et al. |
| 5,731,319 A | 3/1998 | Aberg et al. |
| 6,037,157 A | 3/2000 | Norbeck et al. |
| 6,610,489 B2 | 8/2003 | Wolffe et al. |
| 6,625,547 B1 | 9/2003 | Korzekwa et al. |
| 6,673,778 B1 | 1/2004 | Iversen |
| 6,686,338 B1 | 2/2004 | Iversen |
| 6,790,632 B2 | 9/2004 | Zweig |
| 6,911,438 B2 | 6/2005 | Wright |
| 7,179,597 B2 | 2/2007 | Woosley |
| 7,208,600 B2 | 4/2007 | Cottrell et al. |
| 7,378,422 B2 | 5/2008 | Perni et al. |
| 2002/0142950 A1 | 10/2002 | Hayward et al. |
| 2003/0023387 A1 | 1/2003 | Gill-Garrison et al. |
| 2003/0167135 A1 | 9/2003 | Ewing |
| 2003/0212497 A1 | 11/2003 | Korzekwa et al. |
| 2004/0052865 A1 | 3/2004 | Gower et al. |
| 2004/0180392 A1 | 9/2004 | Prueksaritanont |
| 2004/0229829 A1 | 11/2004 | Iversen |
| 2004/0241714 A1 | 12/2004 | Branch et al. |
| 2005/0049294 A1 | 3/2005 | Palladino et al. |
| 2005/0222071 A1 | 10/2005 | Duranton et al. |
| 2006/0178837 A1 | 8/2006 | Gill-Garrison et al. |

(Continued)

OTHER PUBLICATIONS

Akutsu, Tomoko; Kobayashi, Kaoru; Sakurada, Koichi; Ikegaya, Hiroshi; Furihata, Tomomi; and Chiba, Kan; "Identification of Human Cytochrome P450 Isozymes Involved in Diphenhydramine *N*-Demethylation"; Drug Metabolism and Disposition; bearing a date of 2007; pp. 72-78; vol. 35, No. 1; The American Society for Pharmacology and Experimental Therapeutics; U.S.A.

(Continued)

*Primary Examiner* — Edward Raymond

(57) ABSTRACT

Methods and systems such as those described herein include accepting input, identifying CYP450-family enzymes, identifying at least one modulator of an enzyme, and communicating one or more treatments to a system user.

42 Claims, 32 Drawing Sheets

U.S. PATENT DOCUMENTS

| | | | |
|---|---|---|---|
| 2006/0188562 A1 | 8/2006 | Gower et al. | |
| 2006/0253263 A1 | 11/2006 | Meshkin | |
| 2006/0289019 A1 | 12/2006 | Marchand et al. | |
| 2007/0003931 A1 | 1/2007 | Mrazek et al. | |
| 2007/0026480 A1 | 2/2007 | Modak et al. | |
| 2007/0166816 A1* | 7/2007 | Campbell et al. | 435/288.4 |
| 2008/0085240 A1 | 4/2008 | Flockhart et al. | |

OTHER PUBLICATIONS

Al Omari, Amal; and Murry, Daryl J.; "Pharmacogenetics of the Cytochrome P450 Enzyme System: Review of Current Knowledge and Clinical Significance"; Journal of Pharmacy Practice; bearing a date of 2007; pp. 206-218; vol. 20.3; SAGE Publications.

"AmpliChip CYP450 Test for In Vitro Diagnostic Use"; Roche Diagnostics; bearing a date of Oct. 2007; pp. 1-36; Roche Molecular Systems, Inc.

Bailey, David G.; Malcolm, J.; Arnold, O.; and Spence, J. David; "Grapefruit juice-drug interactions"; British Journal of Clinical Pharmacology; bearing a date of 1998; pp. 101-110; vol. 46; Blackwell Publishing Ltd.

Beaird, Sandra L.; "HMG-CoA Reductase Inhibitors: Assessing Differences in Drug Interactions and Safety Profiles"; Journal of the American Pharmaceutical Association; bearing a date of 2000; pp. 637-644; vol. 40(5); American Pharmaceutical Association; found at http://www.medscape.com/viewarticle/406700.

Benet, Leslie Z.; and Cummins, Carolyn L.; "The drug efflux-metabolism alliance: biochemical aspects"; Advanced Drug Delivery Reviews; bearing a date of 2001; pp. S3-S11; vol. 50; Elsevier Science B.V.

Carruthers, S. George; Shoeman, Don W.; Hignite, Charles E.; and Azarnoff, Daniel L.; "Correlation between plasma diphenhydramine level and sedative and antihistamine effects"; Clinical Pharmacology & Therapeutics; bearing a date of Apr. 1978; vol. 23, No. 4: pp. 375-382.

Cederbaum, Arthur I.; "CYP2E1—Biochemical and Toxicological Aspects and Role in Alcohol-Induced Liver Injury"; The Mount Sinai Journal of Medicine; bearing a date of Jul. 2006; vol. 73, No. 4; pp. 657-672.

Chen, Jie; Yang, Xiao-Xia; Min, Huang; Hu, Ze-Ping; He, Ming; Duan, Wei; Chan, Eli; Sheu, Fwu-Shan; Chen, Xiao; and Zhou Shu-Feng; "Small Interfering RNA-Mediated Silencing of Cytochrome P450 3A4 Gene"; DMD Fast Forward; bearing a date of Jun. 7, 2006; as doi:10.1124/dmd.106.009837; pp. 1-48; American Society for Pharmacology and Experimental Therapeutics.

Coumoul, Xavier; Diry, Monique; Robillot, Cedric; and Barouki, Robert; "Differential Regulation of Cytochrome P450 1A1 and 1B1 by a Combination of Dioxin and Pesticides in the Breast Tumor Cell Line MCF-7"; Cancer Research; bearing a date of May 15, 2001; vol. 61; pp. 3942-3948.

"CYP3A4"; Wikipedia; pp. 1-6; found at http://en.wikipedia.org/wiki/CYP3A4; printed Nov. 7, 2008.

"Cytochrome P450"; Wikipedia; pp. 1-9; found at http://en.wikipedia.org/wiki/Cytochrome_P450; printed Nov. 7, 2008.

Dai, Yan; and Cederbaum, Arthur I.; "Inactivation and Degradation of Human Cytochrome P4502E1 by $CCl_4$ in a Transfected Hep62 Cell Line"; The Journal of Pharmacology and Experimental Therapeutics; bearing a date of 1995; pp. 1614-1622; vol. 275, No. 3; found at jpet.aspetjournals.org.

Do Rego, Amalia Cinthia Meneses; Filho, Irami Araujo; Damasceno, Bolivar P G L; Egito, Eryvaldo Socrates Tabosa; Da Silveira, Ivanaldo Amancio; Brandao-Neto, Jose; and Medeiros, Aldo Cunha; "Simvastatin improves the healing of infected skin wounds of rats"; Acta Cirurgica Brasileira; bearing a date of 2007; pp. 57-63; vol. 22, Supplement 1.

Girre, Catherine; Lucas, Daniele; Hispard, Eric; Menez, Catherine; Dally, Sylvain; and Menez, Jean-Francois; "Assessment of Cytochrome P4502E1 Induction in Alcoholic Patients by Chlorzoxazone Pharmacokinetics"; bearing a date of 1994; Biochemical Pharmacology; pp. 1503-1508; vol. 47, No. 9; Elsevier Science Ltd.

Guengerich, F. Peter; "Cytochrome P450 and Chemical Toxicology"; Chemical Research in Toxicology; bearing a date of 2008; pp. 70-83; vol. 21, No. 1; American Chemical Society.

Gupta, Rajesh; Plantinga, Laura C.; Fink, Nancy E.; Melamed, Michal L.; Coresh, Josef; Fox, Caroline S.; Levin, Nathan W.; and Powe, Neil R.; "Statin Use and Hospitalization for Sepsis in Patients With Chronic Kidney Disease"; Journal of the American Medical Association; bearing a date of Apr. 4, 2007; pp. 1455-1464; vol. 297, No. 13; American Medical Association; located at http://jama.ama-assn.org/cgi/content/full/297/13/1455.

Gupta, Rajesh; Plantinga, Laura C.; and Powe, Neil R.; "Correction: Inaccurate Classification and Information Reported in a Study of Statin Use and Sepsis in Patients With Chronic Kidney Disease"; Journal of the American Medical Association; bearing a date of Feb. 20, 2008; pp. 765-766; vol. 299, No. 7; American Medical Association.

Hanna, Imad H.; Dawling, Sheila; Roodi, Nady; Guengerich, F. Peter; and Parl, Fritz F.; "Cytochrome P450 1B1 (CYP1B1) Pharmacogenetics: Association of Polymorphismms with Functional Differences in Estrogen Hydroxylation Activity"; Cancer Research; bearing a date of Jul. 1, 2000; pp. 3440-3444; vol. 60.

Hanukoglu, Israel; "Steroidogenic enzymes: structure, function, and role in regulation of steroid hormone biosynthesis"; Laboratory of Steroid Molecular Biology; bearing a date of 1992; pp. 1-38.

Hedl, Matija; and Rodwell, Victor W.; "Inhibition of the Class II HMG-CoA reductase of *Pseudomonas mevalonii*"; Protein Science; bearing a date of 2004; pp. 1693-1697; vol. 13; Cold Spring Harbor Laboratory Press.

Hunter, Janice; and Hirst, Barry H.; "Intestinal secretion of drugs. The role of P-glycoprotein and related drug efflux systems in limiting oral drug absorption"; Advanced Drug Delivery Reviews; bearing a date of 1997; pp. 129-157; vol. 25; Elsevier Science B.V.

Jaeschke, Hartmut; Gores, Gregory J.; Cederbaum, Arthur I.; Hinson, Jack A.; Pessayre, Dominique; and Lemasters, John J.; "Forum Mechanisms of Hepatotoxicity"; Toxicological Sciences; bearing a date of 2001; pp. 166-176; vol. 65; The Society of Toxicology.

Jenwitheesuk, Ekachai; Horst, Jeremy A.; Rivas, Kasey L.; Van Voorhis, Wesley C.; and Samudrala, Ram; "Novel paradigms for drug discovery: computational multitarget screening"; Trends in Pharmacological Sciences; bearing a date of Jan. 10, 2008; pp. 62-71; vol. 29, No. 2; Elsevier Ltd.

Kalra, Bhupinder Singh; "Cytochrome P450 Enzyme Isoforms and Their Therapeutic Implications: An Update"; Indian Journal of Medical Sciences; bearing a date of Feb. 2007; pp. 102-116; vol. 61, No. 1.

Kivisto, Kari T.; Kroemer, Heyo K.; and Eichelbaum, Michel; "The role of human cytochrome P450 enzymes in the metabolism of anticancer agents: implications for drug interactions"; British Journal of Clinical Pharmacology; bearing a date of 1995; pp. 523-530; vol. 40; Blackwell Science Ltd.

Liappis, A. P.; Kan, V. L.; Rochester, C. G.; and Simon, G. L.; "The Effect of Statins on Mortality in Patients with Bacteremia"; Clinical Infectious Diseases; bearing a date of Oct. 15, 2001; pp. 1352-1357; vol. 33; Infectious Diseases Society of America.

Madan, Ajay; Graham, Richard A.; Carroll, Kathleen M.; Mudra, Daniel R.; Burton, L. Alayne; Krueger, Linda A.; Downey, April D.; Czerwinski, Maciej; Forster, Jameson; Ribadeneira, Maria D.; Gan, Liang-Shang; Lecluyse, Edward L.; Zech, Karl; Robertson, Philmore Jr.; Koch, Patrick; Antonian, Lida; Wagner, Greg; Yu, Li; and Parkinson, Andrew; "Effects of Prototypical Microsomal Enzyme Inducers on Cytochrome P450 Expression in Cultured Human Hepatocytes"; Drug Metabolism and Disposition; bearing a date of 2003; pp. 421-431; vol. 31, No. 4; The American Society for Pharmacology and Experimental Therapeutics.

McFadyen, Mce; Melvin, WT; and Murray, GI; "Cytochrome P450 CYP1B1 activity in renal cell carcinoma"; British Journal of Cancer; bearing a date of 2004; pp. 966-971; vol. 91(5); Cancer Research UK.

Neuvonen, Pertti J.; Kantola, Teemu; and Kivisto, Kari T.; "Simvastatin but not pravastatin is very susceptible to interaction with the CYP3A4 inhibitor itraconazole"; Clinical Pharmacology & Therapeutics; bearing a date of Mar. 1998; pp. 332-341; vol. 63, No. 3; Mosby, Inc.

Oscarson, Mikael; "Pharmacogenetics of Drug Metabolising Enzymes: Importance for Personalised Medicine"; Clinical Chemistry and Laboratory Medicine; bearing a date of 2003; pp. 573-580; vol. 41, No. 4; Walter de Gruyter • Berlin • New York.

"Personalized Medicine Europe: Health, Genes & Society"; Abstracts presented The Yoran Institute for Human Genome Research, Tel-Aviv University/European Science Foundation Workshop; bearing a date of Jun. 19-21, 2005; Personalized Medicine; pp. 143-185; vol. 2, No. 2; Future Medicine Ltd.

"Pierce® BCA Protein Assay Kit Instructions"; Thermo Scientific; bearing a date of 2008; pp. 1-7; Thermo Fisher Scientific Inc.; U.S.A.; found at www.thermo.com/pierce.

Robertson, Philmore; Decory, Heleen H.; Madan, Ajay; and Parkinson, Andrew; "In Vitro Inhibition and Induction of Human Hepatic Cytochrome P450 Enzymes by Modafinil"; Drug Metabolism and Disposition; bearing a date of 2000; pp. 664-671; vol. 28, No. 6; The American Society for Pharmacology and Experimental Therapeutics; U.S.A.

Rodriguez-Antona, C; and Ingelman-Sundberg, M; "Cytochrome P450 pharmacogenetics and cancer"; Oncogene; bearing a date of 2006; pp. 1679-1691; vol. 25; Nature Publishing Group.

Roy, Partha; Yu, Li J.; Crespi, Charles L.; and Waxman, David J.; "Development of a Substrate-Activity Based Approach to Identify the Major Human Liver P-450 Catalysts of Cyclophosphamide and Ifosfamide Activation Based on cDNA-Expressed Activities and Liver Microsomal P-450 Profiles"; Drug Metabolism and Disposition; bearing a date of 1999; pp. 655-666; vol. 27, No. 6; The American Society for Pharmacology and Experimental Therapeutics; U.S.A.

Tabernero, Lydia; Rodwell, Victor W.; and Stauffacher, Cynthia V.; "Crystal Structure of a Statin Bound to a Class II Hydroxymethylglutaryl-CoA Reductase"; The Journal of Biological Chemistry; bearing a date of May 30, 2003; pp. 19933-19938; vol. 278, No. 22; JBC Papers in Press.

Takada, Kazuki; Arefayene, Million; Desta, Zeruesenay; Yarboro, Cheryl H.; Boumpas, Dimitrios T.; Balow, James E.; Flockhart, David A.; and Illei, Gabor G.; "Cytochrome P450 Pharmacogenetics as a Predictor of Toxicity and Clinical Response to Pulse Cyclophosphamide in Lupus Nephritis"; Arthritis & Rheumatism; bearing a date of Jul. 2004; pp. 2202-2210; vol. 50, No. 7; American College of Rheumatology.

Takahashi, S; Takahashi, T; Mizobuchi, S; Matsumi, M; Morita, K; Miyazaki, M; Namba, M; Akagi, R; and Hirakawa, M; "Increased Cytotoxicity of Carbon Tetrachloride in a Human Hepatoma Cell Line Overexpressing Cytochrome P450 2E1"; The Journal of International Medical Research; bearing a date of 2002; pp. 400-405; vol. 30; Cambridge Medical Publications.

Wilding, E. Imogen; Brown, James R.; Bryant, Alexander P.; Chalker, Alison F.; Holmes, David J.; Ingraham, Karen A.; Iordanescu, Serban; So, Chi Y.; Rosenberg, Martin; and Gwynn, Michael N.; "Identification, Evolution, and Essentiality of the Mevalonate Pathway for Isopentenyl Diphosphate Biosynthesis in Gram-Positive Cocci"; Journal of Bacteriology; bearing a date of Aug. 2000; pp. 4319-4327; vol. 182, No. 15; American Society for Microbiology.

Zanger, Ulrich M.; Raimundo, Sebastian; and Eichelbaum, Michel; "Cytochrome P450 2D6: overview and update on pharmacology, genetics, biochemistry"; Naunyn-Schmiedeberg's Archives of Pharmacology; bearing a date of 2004; pp. 23-37; vol. 369; Springer-Verlag.

* cited by examiner

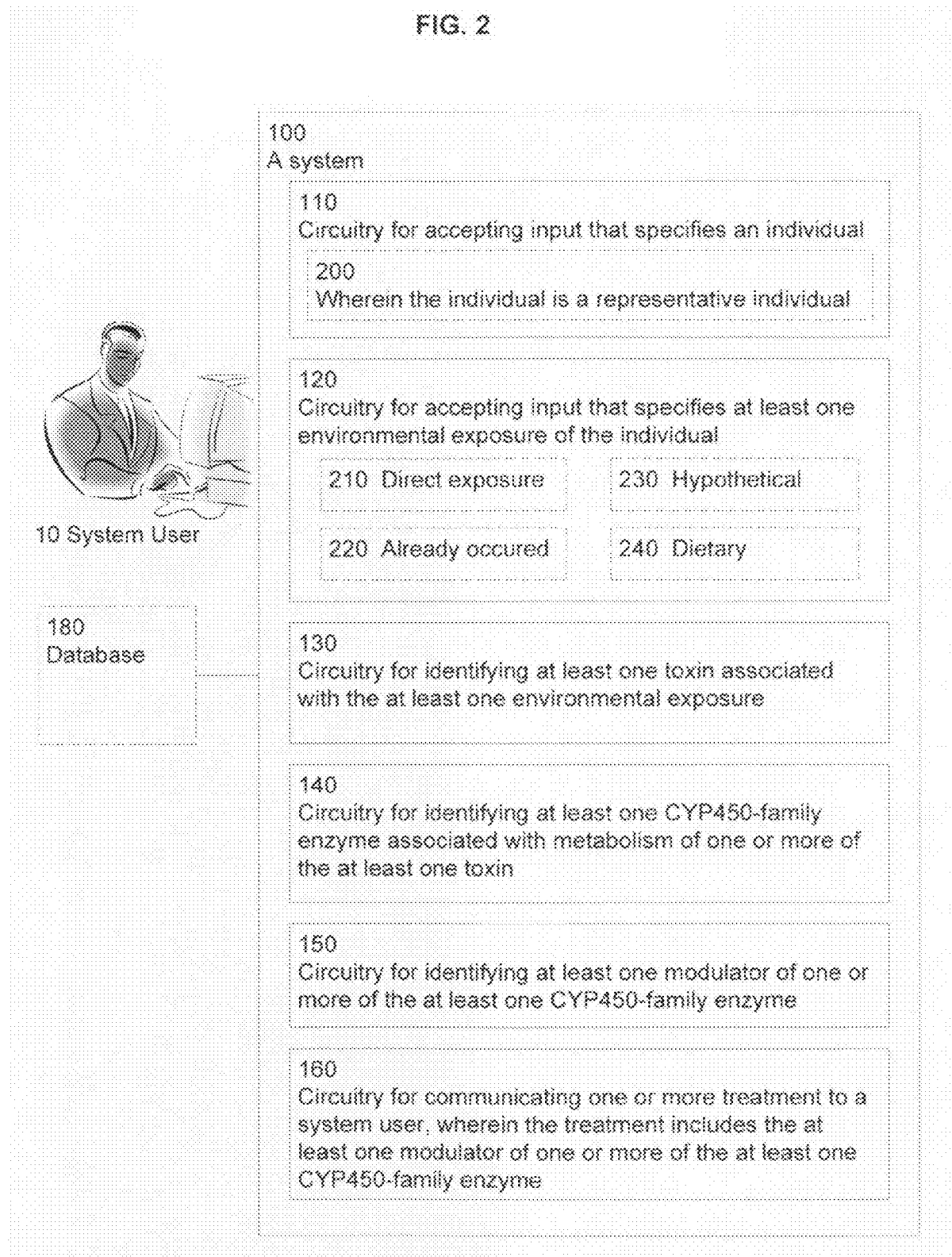

FIG. 3

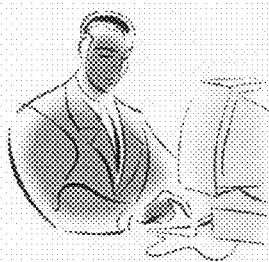

10 System User

180
Database

100
A system

110
  Circuitry for accepting input that specifies an individual

120
  Circuitry for accepting input that specifies at least one environmental exposure of the individual 130
  Circuitry for identifying at least one toxin associated with the at least one environmental exposure 140
  Circuitry for identifying at least one CYP450-family enzyme associated with metabolism of one or more of the at least one toxin 300
    Wherein the at least one CYP450-family enzyme associated with metabolism of one or more of the toxin directly metabolizes the toxin 150
  Circuitry for identifying at least one modulator of one or more of the at least one CYP450-family enzyme 310  Endogenous modulator
    320  Exogenous modulator
    330  Synthetic modulator 160
  Circuitry for communicating one or more treatment to a system user, wherein the treatment includes the at least one modulator of one or more of the at least one CYP450-family enzyme 340  Circuitry for communicating the at least one modulator to a system user

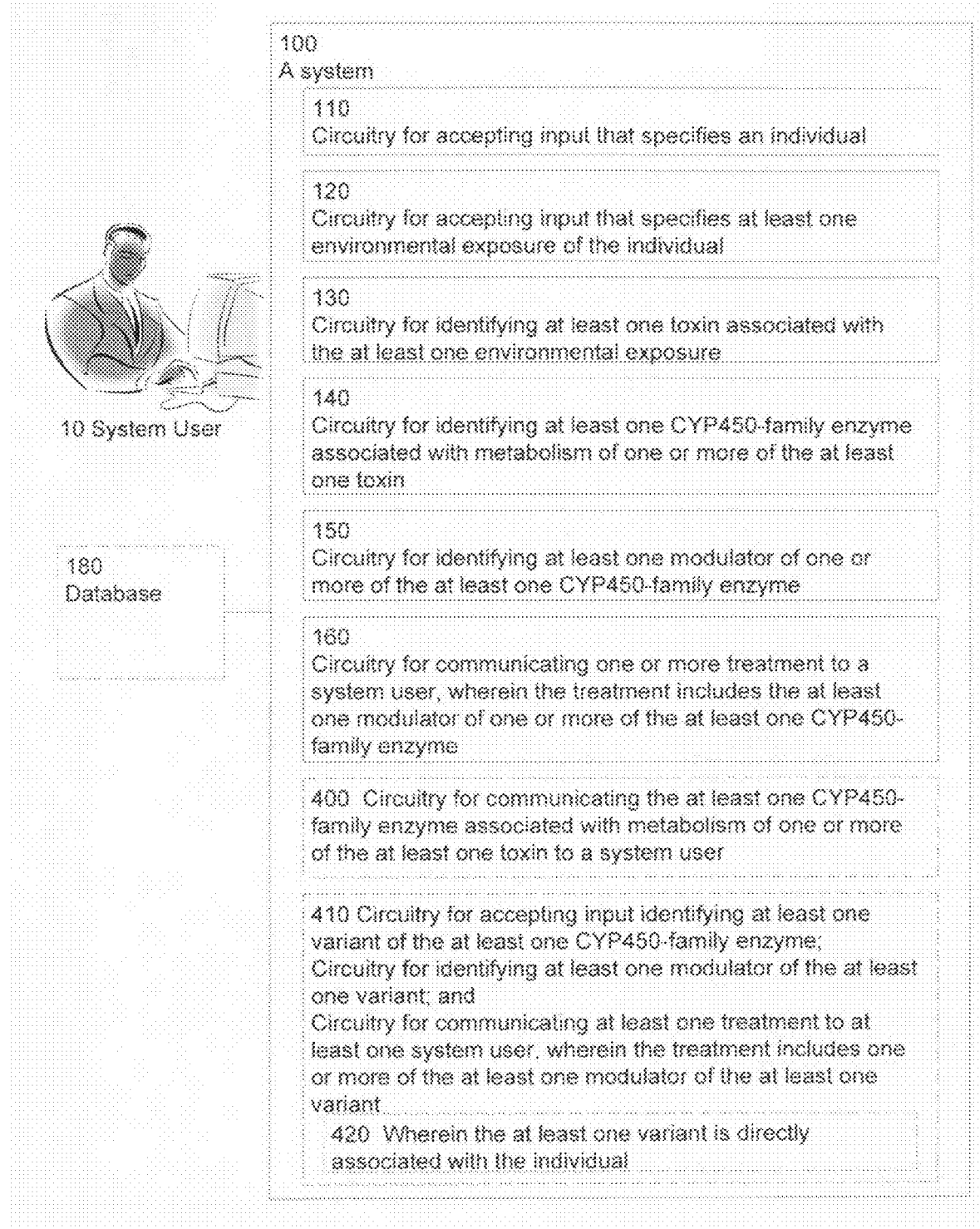

FIG. 9

10 System User

100 A system

110
Circuitry for accepting input that specifies an individual

120
Circuitry for accepting input that specifies at least one environmental exposure of the individual 130
Circuitry for identifying at least one toxin associated with the at least one environmental exposure 140
Circuitry for identifying at least one CYP450-family enzyme associated with metabolism of one or more of the at least one toxin 150
Circuitry for identifying at least one modulator of one or more of the at least one CYP450-family enzyme 180
Database 160
Circuitry for communicating one or more treatment to a system user, wherein the treatment includes the at least one modulator of one or more of the at least one CYP450-family enzyme 900 Circuitry for suggesting one or more dosages of the one or more treatment to a system user;
Circuitry for identifying at least one dietary factor associated with an alteration in activity of at least one of the one or more treatment; and
Circuitry for communicating one or more alternate dosages of the one or more treatment to at least one system user, wherein the one or more alternate dosages are calculated to compensate for the alteration in activity of at least one of the one or more treatment 910 Wherein the at least one dietary factor is associated with the individual 920 Circuitry for associating at least one anatomic location with predicted activity of the at least one CYP450-family enzyme;
Circuitry for associating the at least one anatomic location with one or more of the at least one modulator; and
Circuitry for communicating at least one treatment to a system user, wherein the treatment includes the at least one modulator of the at least one CYP450-family enzyme associated with the at least one anatomic location

FIG. 14

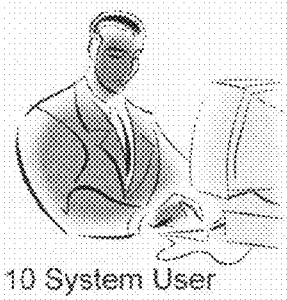
10 System User

1060 Database

1000
A system

1010 Circuitry for accepting input relating to microbial infection associated with an individual 1020 Circuitry for identifying at least one statin therapy, wherein the at least one statin therapy is associated with a reduction in the microbial infection 1030 Circuitry for identifying at least one CYP450-family enzyme, wherein the CYP450-family enzyme is associated with metabolism of the at least one statin therapy 1040 Circuitry for identifying at least one modulator of the at least one CYP450-family enzyme 1050 Circuitry for communicating one or more treatment to a system user, wherein the at least one treatment includes the at least one statin therapy and the at least one modulator 1400
Circuitry for suggesting one or more dosages of the one or more treatment to a system user;
Circuitry for identifying at least one dietary factor associated with an alteration in activity of at least one of the one or more treatment; and
Circuitry for communicating one or more alternate dosages of the one or more treatment to a system user, wherein the one or more alternate dosages are calculated to compensate for the alteration in activity of at least one of the one or more treatment 1410
Circuitry for communicating at least one treatment to a system user, wherein the treatment includes one or more of the at least one statin therapy and one or more of the at least one modulator

COMPUTATIONAL METHODS AND SYSTEMS FOR TREATMENT IN RELATION TO MODULATION OF CYP450 ENZYME ACTIVITY

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 12/319,154, entitled COMPUTATIONAL METHODS AND SYSTEMS FOR SUGGESTING MODULATORS OF CYP450 AS TREATMENT OPTIONS, naming Mahalaxmi Gita Bangera, Roderick A. Hyde, Elizabeth A. Sweeney, and Lowell L. Wood, Jr. as inventors, filed Dec. 30, 2008, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

In one aspect, a method includes but is not limited to: accepting input that specifies an individual; accepting input that specifies at least one environmental exposure of the individual; identifying at least one toxin associated with the at least one environmental exposure; identifying at least one CYP450-family enzyme associated with metabolism of one or more of the at least one toxin; identifying at least one modulator of one or more of the at least one CYP450-family enzyme; and invoking circuitry for communicating one or more treatment to a system user, wherein the treatment includes the at least one modulator of one or more of the at least one CYP450-family enzyme.

In one aspect, a method includes but is not limited to: accepting input relating to microbial infection associated with an individual; identifying at least one statin therapy, wherein the at least one statin therapy is associated with a reduction in the microbial infection; identifying at least one CYP450-family enzyme, wherein the at least one CYP450-family enzyme is associated with metabolism of the at least one statin therapy; identifying at least one modulator of the at least one CYP450-family enzyme; and invoking circuitry for communicating at least one treatment to a system user, wherein the at least one treatment includes the at least one statin therapy and the at least one modulator.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In one aspect, a system includes but is not limited to: circuitry for accepting input that specifies an individual; circuitry for accepting input that specifies at least one environmental exposure of the individual; circuitry for identifying at least one toxin associated with the at least one environmental exposure; circuitry for identifying at least one CYP450-family enzyme associated with metabolism of one or more of the at least one toxin; circuitry for identifying at least one modulator of one or more of the at least one CYP450-family enzyme; and circuitry for communicating one or more treatment to a system user, wherein the treatment includes the at least one modulator of one or more of the at least one CYP450-family enzyme.

In one aspect, a system includes but is not limited to: circuitry for accepting input relating to microbial infection associated with an individual; circuitry for identifying at least one statin therapy, wherein the at least one statin therapy is associated with a reduction in the microbial infection; circuitry for identifying at least one CYP450-family enzyme, wherein the at least one CYP450-family enzyme is associated with metabolism of the at least one statin therapy; circuitry for identifying at least one modulator of the at least one CYP450-family enzyme; and circuitry for communicating at least one treatment to a system user, wherein the at least one treatment includes the at least one statin therapy and the at least one modulator.

In one aspect, a system includes but is not limited to: at least one computer program for use with at least one computer system and wherein the computer program includes a plurality of instructions including but not limited to: one or more instructions for accepting input that specifies an individual; one or more instructions for accepting input that specifies at least one environmental exposure of the individual; one or more instructions for identifying at least one toxin associated with the at least one environmental exposure; one or more instructions for identifying at least one CYP450-family enzyme associated with metabolism of one or more of the at least one toxin; one or more instructions for identifying at least one modulator of one or more of the at least one CYP450-family enzyme; and one or more instructions for communicating one or more treatment to a system user, wherein the treatment includes the at least one modulator of one or more of the at least one CYP450-family enzyme.

In one aspect, a system includes but is not limited to: at least one computer program for use with at least one computer system and wherein the computer program includes a plurality of instructions including but not limited to: one or more instructions for accepting input relating to microbial infection associated with an individual; one or more instructions for identifying at least one statin therapy, wherein the at least one statin therapy is associated with a reduction in the microbial infection; one or more instructions for identifying at least one CYP450-family enzyme, wherein the CYP450-family enzyme is associated with metabolism of the at least one statin therapy; one or more instructions for identifying at least one modulator of the at least one CYP450-family enzyme; and one or more instructions for communicating at least one treatment to a system user, wherein the at least one treatment includes the at least one statin therapy and the at least one modulator.

The foregoing summary is illustrative only and is not intended to be in any way limiting. In addition to the illustrative aspects, embodiments, and features described above, further aspects, embodiments, and features will become apparent by reference to the drawings and the following detailed description. In addition to the foregoing, various other method and/or system and/or program product aspects are set forth and described in the teachings such as text (e.g., claims and/or detailed description) and/or drawings of the present disclosure.

BRIEF DESCRIPTION OF THE FIGURES

FIG. 2 is a diagram illustrating some aspects of a system such as the one depicted in FIG. 1.
FIG. 3 is a diagram showing some aspects of a system such as the one depicted in FIG. 1.
FIG. 4 is a diagram illustrating some aspects of a system such as the one depicted in FIG. 1.
FIG. 9 is a diagram showing some aspects of a system such as the one depicted in FIG. 1.
FIG. 14 is a diagram illustrating some aspects of a system such as the one depicted in FIG. 10.

The use of the same symbols in different drawings typically indicates similar or identical items.

DETAILED DESCRIPTION

Figure 1:
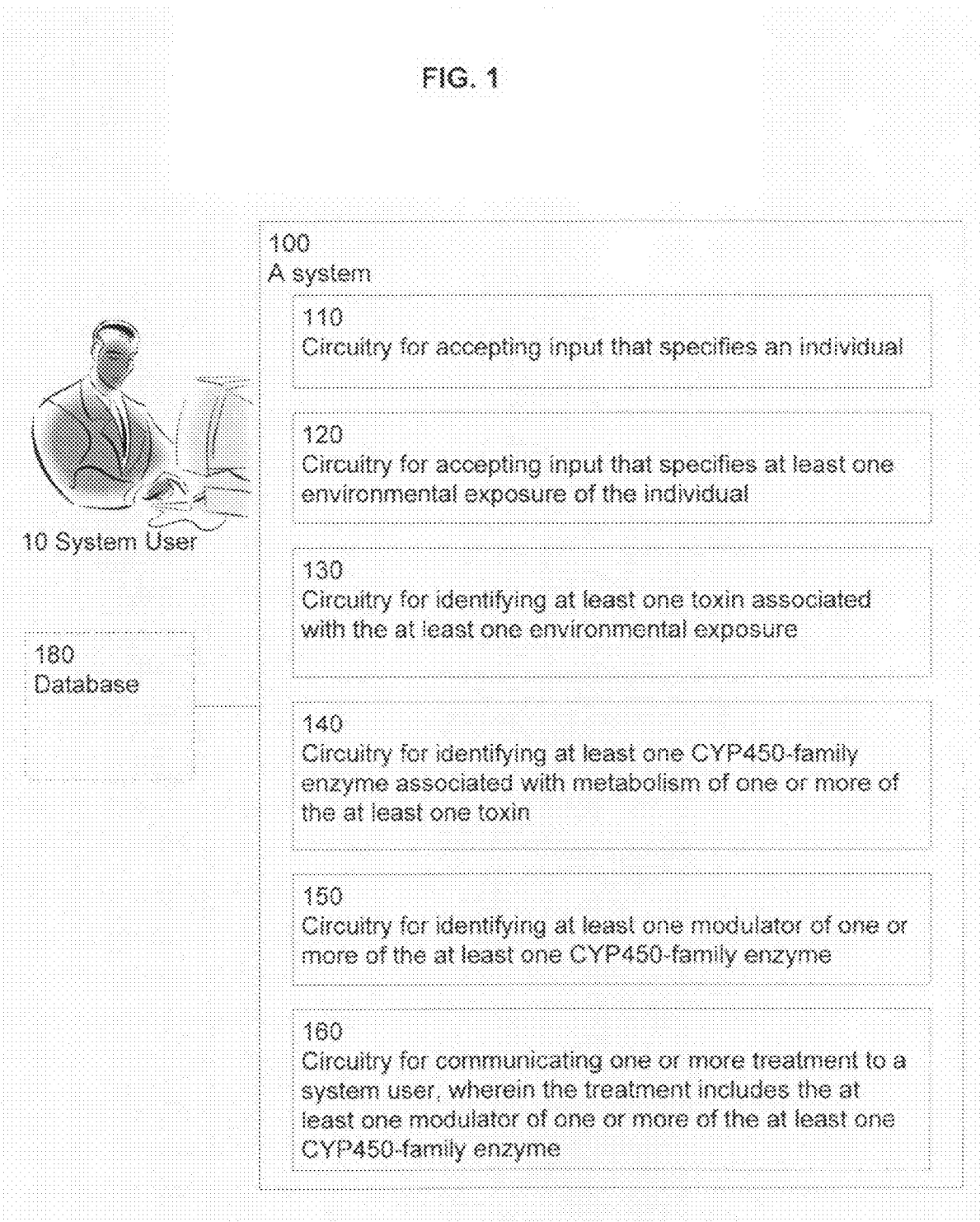
FIG. 1 is a diagram showing some aspects of a system.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 depicts some aspects of a system including circuitry. A system 100 may include: circuitry for accepting input that specifies an individual 110; circuitry for accepting input that specifies at least one environmental exposure of the individual 120; circuitry for identifying at least one toxin associated with the at least one environmental exposure 130; circuitry for identifying at least one CYP450-family enzyme associated with metabolism of one or more of the at least one toxin 140; circuitry for identifying at least one modulator of one or more of the at least one CYP450-family enzyme 150; and circuitry for communicating one or more treatment to a system user, wherein the treatment includes the at least one modulator of one or more of the at least one CYP450-family enzyme 160. The system 100 may include or may be connected to at least one database, such as that depicted as database 180. A database may be a publicly-available, privately-available, or a limited-access database, and may include, for example, information regarding: CYP450-family enzymes, genes and variants; metabolic pathways that include or are influenced by CYP450-family enzymes; toxins; environmental exposures; modulators of CYP450-family enzymes and variants; treatments, including those that contain at least one modulator of a CYP450-family enzyme; population-based data regarding individuals, CYP450-family variants, or environmental exposures; dosage schedules; dietary factors; and specific data regarding individuals. A system 100 may accept input and communicate with a system user 10.

A system may include at least one computer program for use with at least one computer system and wherein the computer program includes a plurality of instructions including but not limited to: one or more instructions for accepting input that specifies an individual; one or more instructions for accepting input that specifies at least one environmental exposure of the individual; one or more instructions for identifying at least one toxin associated with the at least one environmental exposure; one or more instructions for identifying at least one CYP450-family enzyme associated with metabolism of one or more of the at least one toxin; one or more instructions for identifying at least one modulator of one or more of the at least one CYP450-family enzyme; and one or more instructions for communicating one or more treatment to a system user, wherein the treatment includes the at least one modulator of one or more of the at least one CYP450-family enzyme.

A system may include at least one computer program for use with at least one computer system and wherein the computer program includes a plurality of instructions including but not limited to: one or more instructions for accepting input relating to microbial infection associated with an individual; one or more instructions for identifying at least one statin therapy, wherein the at least one statin therapy is associated with a reduction in the microbial infection; one or more instructions for identifying at least one CYP450-family enzyme, wherein the CYP450-family enzyme is associated with metabolism of the at least one statin therapy; one or more instructions for identifying at least one modulator of the at least one CYP450-family enzyme; and one or more instructions for communicating at least one treatment to a system user, wherein the at least one treatment includes the at least one statin therapy and the at least one modulator.

A system, such as systems depicted as 100 and 1000, may be connected to a user interface and communicate with a system user such as that depicted as system user 10. A user interface may include visual interfaces such as monitors or display devices, may include audio devices that communicate through sound or vibration, may include tactile interfaces, or may include some combination of types of user interfaces. A user interface may be used by the system user to input information or data into the system. For example, the user interface may include one or more: keyboards; sound receivers; computer mouses; "dropdown" menu options; or touchpads. A user interface may be used to communicate information from the system to the user. For example, a user interface may include one or more of: sound transmitters; optical transmitters; monitors; or visual interaction interfaces. A system user may include medical personnel such as a physician, nurse, pharmacist or therapist, or may include a medical team. A system user may include researchers, scientists, or medical investigators, such as those involved in, for example, a clinical trial or a research program including human subjects. In some instances a system user may include drug developers, such as drug testing personnel or experimental pharmacists. In some instances, a system user may include patients or individuals associated with one or more drug therapies. Although system user 10 is shown herein as a single illustrated figure, those skilled in the art will appreciate that system user 10 may be representative of a human user, a robotic user (e.g., computational entity), and/or substantially any combination thereof (e.g., a user may be assisted by one or more robotic agents) unless context dictates otherwise. Those skilled in the art will appreciate that, in general, the same may be said of "sender" and/or other entity-oriented terms as such terms are used herein unless context dictates otherwise.

A system user may communicate input with the system. For example, a system user may type into a keyboard or manipulate preset visual menus via mouse, touchscreen, or other user interface. For example, a system user may make sound or visual cues which are interpreted as input by the user interface. A system user may, for example, send input to communicate with the system. Input may include information that specifies an individual. Input may include information that identifies at least one environmental exposure associated with the individual. Input may include information specifying one or more variant of at least one CYP450-family enzyme. Input may include information relating to microbial infection associated with an individual. Input may include information that specifies at least one environmental exposure associated with the individual.

A system may communicate with a system user. For example, a system may communicate one or more treatment to a system user. For example, a system may invoke circuitry for communicating one or more treatment to a system user. A system may communicate with a system user through a user interface.

An "environmental exposure," as used herein, includes any actual, potential, assumed, or hypothetical exposure to one or more factors in the environment. An "environmental exposure" includes, but is not limited to, physical exposure to some aspect of a person's surroundings. An "environmental exposure" includes, but is not limited to, gasses, liquids, gels, powders, slurries, and solids, or a combination thereof. An "environmental exposure" may come into contact with an individual, for example, though direct contact, inhalation, ingestion, or transdermally. An environmental exposure may include exposure in any quantity, and may or may not be recognized at the time of exposure. For example, a person may be exposed to a toxin in a small quantity and experience few if any effects from the exposure at the time or soon thereafter. For example, a person may be exposed to a toxin in a large quantity and experience a sudden effect, such as: allergic response, disease state, sickness, loss of consciousness, shortness of breath, or dizziness. In some situations, different individuals may have divergent symptoms or experiences in relation to the same environmental exposure, which may be in relation to one or more of: quantity of exposure by each individual: quality of exposure (i.e. location or means of exposure); duration of exposure; and individual-based differences (such as different CYP450-family variants, genes or alleles). A quantity of an environmental exposure may yield different effects depending on, for example, formulation, co-factors, temperature, composition, or physical state. In some situations, an environmental exposure may include more than one component that leads to effects for one or more individuals.

A "toxin," as used herein, includes any compound, component or chemical which is known or suspected to have negative physiological effects, including sickness, disease or increased risk of sickness or disease states. As used herein, a "toxin" may include one or more chemicals or compounds with negative effects for at least one individual. In some instances, a toxin may be associated with death, serious metabolic disorder, or substantial physiological impairment. In some aspects, a toxin may be a synthetic chemical. In some aspects, a toxin may be naturally derived from plant, bacteria, yeast, or animals. In some instances, a toxin may be a previously-identified toxin, while in others it may be completely unknown, only partially characterized, or minimally understood. In some instances a toxin may be part of or have origins in a known pathogen. For example, toxins may include aflatoxin $B_1$, or ethyl carbamate.

At least one toxin may be associated with an environmental exposure. In some situations, a toxin may have negative effects for some number of individuals while having no discernable effect for some number of individuals. A toxin may include a pesticide, herbicide, cleaning solution, or industrial chemical. For example, a toxin may include at least one of: dioxin, a-endosulfan, or furans. A toxin may be a carcinogenic agent. In some situations, the effect of a toxin is related to an individual's CYP450-family enzymes, variants, or genes. In some situations, the effect of a toxin is related to quantity, quality, route, duration or means of exposure by a person or group. In some situations, a toxin originates from a prokaryotic or eukaryotic organism, while in other situations a toxin has purely or predominately chemical origin. A toxin may be associated with an environmental exposure, for example, by being a known or suspected component of the environmental exposure, or by being a suspected component of the environmental exposure. In some situations, a toxin may be associated with an environmental exposure through indirect, statistical, or population-based methods although no specific component or compound has been detected. In some embodiments, a toxin may be the result of multiple exposures to different substances which combine or interact to create at least one toxin.

A "CYP450-family enzyme," as used herein, may include any of the polypeptides encoded by the cytochrome p-450 family of genes. For example, a CYP450-family enzyme may include polypeptides encoded by one or more of the following genes: CYP1A1, CYP1A2, CYP2C9, CYP2A6, CYP2B6, CYP2C8, CYP2C9, CYP2C19, CYP2D6, CYP2E1, CYP3A4, and CYP3A5. A CYP450-family enzyme may include, for example, the enzyme encoded by the CYP1A1 gene which may be referred to in various contexts as the CYP1A1 protein, or the CYP1A1 enzyme, or cytochrome p450 1A1, or xenobiotic monooxygenase, or aryl hydrocarbon hydroxylase, or flavoprotein-linked monooxygenase, or dioxin-inducible cytochrome P1-450, or cytochrome p450 polypeptide 1 subfamily I (aromatic compound-inducible). For example, CYP450-family enzymes include a group of enzymes which are steroidogenic, as described in: Hanukoglu, Steroidogenic enzymes: structure, function, and role in regulation of steroid hormone biosynthesis. J. Steroid Biochem. Mol. Biol. 43:779-804, 1992, which is herein incorporated by reference.

A CYP450-family enzyme may be associated with metabolism of one or more of the at least one toxin either directly or indirectly. For example, a CYP450-family enzyme may influence metabolism of a toxin by directly acting as a cofactor in the metabolism of some portion of the toxin. For example, a CYP450-family enzyme may influence metabolism of a toxin by directly participating in one or more reactions as part of the physiological processing of some portion of the toxin. For example, a CYP450-family enzyme may influence metabolism of a toxin by indirectly influencing a metabolic pathway that includes the metabolism of some portion of the toxin. A toxin may be identified with a metabolism that may be influenced by a CYP450-family enzyme through computational or predictive methods, such as those described in US Patent Application 20030212497 to Korzekwa, entitled "Relative rates of cytochrome P450 metabolism," which is incorporated by reference herein. A toxin may be predicted to be metabolized by one or more CYP450-family enzymes by methods such as those described in U.S. Pat. No. 6,625,547 to Korezkwa, entitled "Relative rates of Cytochrome P450 metabolism," which is herein incorporated by reference.

In some aspects, a toxin may itself influence one or more CYP450-family enzymes by directly altering the bioavailability of the enzyme itself. For example, a toxin may increase or decrease the bioavailability of the enzyme itself. For example, a toxin may be an estrogen or a estrogen mimic, and therefore compete for bioavailability of CYP1B1 or CYP1A1 (see Hanna et al., Cytochrome P450 1B1 (CYP1B1 pharmacogenetics: association of polymorphisms with functional differences in estrogen hydroxylation activity, Cancer Research 60, 3440-3444, (2000), which is incorporated by reference herein. For example, a toxin may directly decrease functional CYP450-family enzyme levels (see Coumoul et al., Differential Regulation of Cytochrome P450 1A1 and 1B1 by a combination of dioxin and pesticides in the breast tumor cell line MCF-7, Cancer Research 61, 3942-3948 (2001), which is incorporated by reference herein.) A toxin may be associated with an environmental exposure, such as pesticide exposure.

Some aspects of the systems and methods described herein include identifying at least one modulator of one or more CYP450-family enzyme. A "modulator" of a CYP450-family enzyme, as used herein, includes any compound, material, drug, chemical, or agent that is predicted or known to act to modulate the activity of at least one CYP450-family enzyme. For example, a modulator of a CYP450-family enzyme may be a compound that is predicted to inhibit the enzymatic activity of the CYP450-family enzyme. For example, a modulator may include a compound predicted to bind to one or more CYP450-family enzymes in a binding assay such as those described in U.S. Pat. No. 6,790,632 to Zweig, entitled "Membrane receptor reagent and assay," which is herein incorporated by reference. For example, a modulator may be a compound that is predicted to enhance the enzymatic activity of the CYP450-family enzyme. For example, a modulator may include a compound that is known or predicted to increase or decrease transcription of a CYP450-family gene corresponding to a CYP450-family enzyme, and therefore is predicted to result in the increased expression and activity of the CYP450-family enzyme. For example, ethanol has been shown to increase expression of CYP2E1; see Dai and Cederbaum, Inactivation and degradation of human Cytochrome P4502E1 by $CCl_4$ in a transfected Hep62 cell line, The Journal of Pharmacology and Experimental Therapeutics, 275, 1614-1622 (1995), which is incorporated by reference herein. For example, a modulator may be identified through methods such as those described in U.S. Pat. No. 6,610,489 to Wolffe, entitled "Pharmacogenomics and identification of drug targets by reconstruction of signal transduction pathways based on sequences of accessible regions," which is herein incorporated by reference. For example, a modulator may include a RNAi compound that acts or is predicted to act to limit the available RNA transcribed from a CYP450-family gene and therefore limit the levels of CYP450-family enzyme available for activity. For example, a modulator may include RNAi oligonucleotides as described by Chen et al., or be developed using the methods discussed by Chen et al (Chen et al., Small interfering RNA-mediated silencing of Cytochrome p450 3A4 gene, DMD Fast Forward, published Jun. 7, 2006 as doi: 10.1124/dmd.106.009837, which is herein incorporated by reference).

For example, a modulator may include a snRNA compound that acts or is predicted to act to limit the available RNA transcribed from a CYP450-family gene and therefore limit the levels of CYP450-family enzyme available for activity. For example, a modulator may include an antisense oligonucleotide-containing compound that acts or is predicted to act to limit the available RNA transcribed from a CYP450-family gene and therefore limit the levels of CYP450-family enzyme available for activity. For example, a modulator may include oligomers such as those described in US Patent Application No. 20040229829 to Iversen, entitled "Enzyme inhibitors for metabolic redirection," which is incorporated by reference herein. For example, a modulator may be developed incorporating the methods described in U.S. Pat. Nos. 6,673,778 and 6,686,338 to Iversen, entitled "Enzyme inhibitors for metabolic redirection," which is incorporated by reference herein. For example, a modulator may include at least one double-stranded RNA oligonucleotide such as those described in US Patent Application No. 20050222071 to Duranton, entitled "Topical administrations of at least one double-stranded RNA oligonucleotide (dsRNA)," which is herein incorporated by reference. For example, a modulator may be a compound that is known or predicted to act to increase translation of the RNA transcript from the CYP450-family gene and therefore increase available CYP450-family enzyme. For example, a modulator may include a compound that increases metabolic catalysis of the CYP450-family enzyme, thereby decreasing the bioavailability of the CYP450-family enzyme. For example, a modulator may include a compound that decreases metabolic catalysis of the CYP450-family enzyme, thereby increasing the bioavailability of the CYP450-family enzyme. A modulator may be directed to a specific anatomic location, such as an organ, region, or area of the body, for example, the small intestine, the large intestine, the stomach, the liver, or the kidneys. For example, a modulator may be delivered into a body within a particle such as those described in US Patent Application Nos. 20040052865 and 20060188562 to Gower, entitled "Materials and methods for drug delivery and uptake," which are herein incorporated by reference. A modulator may include methods and compositions such as those described in US Patent Application No. 20020142950 to Hayward, entitled "Methods for enhancing the bioavailability of a drug," which is incorporated by reference herein. A modulator may be predicted to bind to at least one CYP450-family enzyme, for example using prediction methods such as those described in US Patent Application No. 20030167135 to Ewing, entitled "Non-linear modeling of biological activity of chemical compounds," which is incorporated by reference herein. A modulator may be developed in part through computational methods such as those described in Jenwitheesuk et al., Novel paradigms for drug discovery: computational multitarget screening, Trends in Pharmacological Sciences 29(2), 62-71, 2008, which is herein incorporated by reference.

In some aspects, a system includes circuitry for communicating one or more treatment to a system user. A "treatment," as used herein, may include a therapy, medicinal, plan of action, dosage schedule, course of treatment or a combination thereof which is reasonably expected to mitigate a medical situation experienced by the individual. In some aspects, a treatment may include a known drug treatment, including pharmaceutical treatments, herbal remedies, traditional therapy (such as traditional Chinese, Indian, or European remedies) or a combination thereof. In some aspects, a treatment may be directed to a known medical situation or it may be directed to a nonapparent, hypothetical, predicted or supposed medical situation. In some aspects, a treatment may include a negative suggestion, such as to avoid an environmental exposure (e.g. "do not breathe air from this area, which is known or suspected to be contaminated with toxin").

In some aspects, a treatment may include a positive suggestion, which may also mitigate environmental exposure (e.g. include a directive to drink liquid from a source which is not known or suspected to contain toxin). In some aspects, a treatment may include suggestions directed toward overall health (e.g. to drink sufficient liquids to maintain body hydration). A treatment may include one or more of the identified at least one modulator of one or more of the at least one first CYP450-family enzyme and one or more of the identified at least one modulator of one or more of the at least one second CYP450-family enzyme. For example, a treatment may include a compound that includes both one or more of the identified at least one modulator of one or more of the at least one first CYP450-family enzyme and one or more of the identified at least one modulator of one or more of the at least one second CYP450-family enzyme in the same intended dosage or administration. For example, a treatment may include one or more of the identified at least one modulator of one or more of the at least one first CYP450-family enzyme and one or more of the identified at least one modulator of one or more of the at least one second CYP450-family enzyme in distinct dosages or administrations, including via different modes of administration (e.g. oral and intravenous). A treatment may include aspects or compositions targeted for delivery in certain regions or to certain tissues. A treatment may be delivered through particle-based delivery, such as those described in US Patent Application No. 20020142950 to Hayward, entitled "Methods for enhancing the bioavailability of a drug," which is incorporated by reference herein. A treatment may include topical administration, for example as described in U.S. Pat. No. 5,658,881 to Gelland, entitled "Method for topical inhibition of the metabolic activity of Cytochrome P450," which is herein incorporated by reference. A treatment may be further refined with methods such as those described in U.S. Pat. No. 6,037,157 to Norbeck, entitled "Method for improving pharmacokinetics," which is herein incorporated by reference. A treatment may include one or more modulators such as those described in U.S. Pat. No. 7,208,600 to Cottrell, entitled "Inhibitors of serine proteases, particularly HCV NS3-NS4A proteases," which is herein incorporated by reference. A treatment may be one or more modulators such as those described in U.S. Pat. No. 7,378,422 to Perni, entitled "Inhibitors of serine proteases, particularly HCV NS3-NS4A protease," which is herein incorporated by reference.

In some embodiments, treatments may include one or more drugs packaged or sorted in such a manner as to facilitate suggested dosages or dosage schedules such as those developed by methods and systems disclosed herein. For example, a treatment may be: dispensed or packaged in a manner to facilitate daily, weekly, or monthly dosages; or packaged or dispensed in combinations and composition amounts for each administration.

In some embodiments, systems and methods such as those described herein may be used in conjunction with methods for assessing disease susceptibility associated with environmental risk factors, such as those described in US Patent Application Nos. 20030023387 and 20060178837 to Gill-Garrison entitled "Computer-assisted means for assessing lifestyle risk factors," which are incorporated by reference herein.

In some embodiments, systems and methods such as those described herein may be used in conjunction with methods to optimize drug selection, such as those described in US Patent Application 20060253263 to Meshkin, entitled "Method to optimize drug selection, dosing and evaluation and to help predict therapeutic response and toxicity from immunosuppressant therapy," which is herein incorporated by reference.

In some embodiments, systems and methods such as those described herein may be used in conjunction with information methods and systems for generating data for optimizing a medical treatment, such as those described in US Patent Application No. 20060289019 to Marchand, entitled "Information method and system for generating data for optimizing a medical treatment, and equipment used in this system," which is herein incorporated by reference.

In some embodiments, systems and methods such as those described herein may be used in conjunction with methods for selecting medications, such as those described in US Patent Application No. 20070003931 to Mrazek, entitled "Methods for selecting medications," which is herein incorporated by reference.

In some aspects, an individual may be a specific identified person or entity, such as an individual person identified by name (e.g. Jane Doe) or identification number (e.g. 12345). In some aspects, an individual may be a representative individual. For example, the individual may be a composite, median, average or hypothetical individual. For example, the individual may include representative characteristics from a population, cohort or group and represent aspects of the group. For example, an individual may be a person known or suspected to have one or more particular CYP450-family gene alleles. For example, an individual may be part of a population, cohort or group with known or putative CYP450-family allele frequencies and probabilities. In some embodiments, an individual may be a generic or population-based individual and one or more treatments may be developed in advance, and stored until such time as they become needful for one or more patients in a given situation. For example, the individual may be specified generally by age, gender, race, body mass, disease state, health status or other physiological condition. For example, the individual may be specified generally by place of residence, place of employment or exposure through having been in a location. For example, the individual may be specified generally by environmental exposure profile, such as, for example, drinking water from a specific source, coming in contact with a known or potential environmental hazard, or employment in a specific industry or location. For example, the individual may be specified generally by known or suspected microbial exposure, such as a person who has tested positive for an infection, come into contact with a person who has the infection, or been in a location where one or more infectious agents are known or suspected to be present. For example, the individual may be identified as a 55 year old African-American male with a history of heart disease who obtains drinking water from a specific location. For example, the individual may be identified as a 35 year old Caucasian woman with type I diabetes who smokes. For example, the individual may be identified as a 45 year old Asian man with a BMI of 30 and exposure to cleaning products. For example, the individual may be identified as a woman of mixed racial ancestry in her sixth decade with no known substantial medical history and who has recently completed 20 years of employment in a dry-cleaning establishment. For example, the individual may be specified as a person with no known medical history who works as a medical provider in a medical institution, such as a hospital, clinic, nursing home, care facility, or laboratory. For example, the individual may be specified as a person with no known medical history who has recently spent time in a location where a specific pathogen is known or suspected to exist. In some aspects, an individual may be specified by their relationship to another person, such as, for example, "mother of patient XYZ" or "brother of individual with microbial infection." An individual may be specified by their inclusion in a specific ethnic, population or family group, such as, for example, "Caucasian," "first-degree relative of patient VPR" or "predominately of Italian descent."

FIG. 2 depicts some aspects of a system such as the one shown in FIG. 1. In some embodiments, circuitry for accepting input that specifies an individual 110 may include circuitry wherein the individual is a representative individual 200. In some embodiments, circuitry for accepting input that specifies an individual 110 may include circuitry wherein the individual is an identified person. In some embodiments, circuitry for accepting input that specifies at least one environmental exposure of the individual 120 may include circuitry wherein the at least one environmental exposure is a direct exposure to the individual 210. In some embodiments, circuitry for accepting input that specifies at least one environmental exposure of the individual 120 may include circuitry wherein the at least one environmental exposure is an indirect exposure to the individual. In some embodiments, circuitry for accepting input that specifies at least one environmental exposure of the individual 120 may include circuitry wherein the at least one environmental exposure has already occurred 220. In some embodiments, circuitry for accepting input that specifies at least one environmental exposure of the individual 120 may include circuitry wherein the at least one environmental exposure is ongoing. In some embodiments, circuitry for accepting input that specifies at least one environmental exposure of the individual 120 may include circuitry wherein the at least one environmental exposure is continuous. In some embodiments, circuitry for accepting input that specifies at least one environmental exposure of the individual 120 may include circuitry wherein the at least one environmental exposure is hypothetical 230. In some embodiments, circuitry for accepting input that specifies at least one environmental exposure of the individual 120 may include circuitry wherein the at least one environmental exposure is known. In some embodiments, circuitry for accepting input that specifies at least one environmental exposure of the individual 120 may include circuitry wherein the at least one environmental exposure is suspected. In some embodiments, circuitry for accepting input that specifies at least one environmental exposure of the individual 120 may include circuitry wherein the at least one environmental exposure is dietary 240. In some embodiments, circuitry for accepting input that specifies at least one environmental exposure of the individual 120 may include circuitry wherein the at least one environmental exposure is transdermal. In some embodiments, circuitry for accepting input that specifies at least one environmental exposure of the individual 120 may include circuitry wherein the at least one environmental exposure is inhaled. In some embodiments, circuitry for accepting input that specifies at least one environmental exposure of the individual 120 may include circuitry wherein the at least one environmental exposure is via mucus membranes.

FIG. 3 depicts aspects of a system such as the one shown in FIG. 1. In some embodiments, circuitry for identifying at least one CYP450-family enzyme associated with metabolism of one or more of the at least one toxin 140 includes circuitry wherein the at least one CYP450-family enzyme associated with metabolism of one or more of the toxin directly metabolizes the toxin 300. The at least one CYP450-family enzyme that associated with metabolism of one or more of the toxin may be known or predicted to influence metabolism of the toxin associated with the individual. The at least one CYP450-family enzyme that associated with metabolism of one or more of the toxin may influence metabolism through directly metabolizing all or some component of the toxin or it may influence metabolism of the toxin therapy indirectly through an effect on a metabolic pathway. For example, a toxin may have xenoestrogenic effects and influence a hormone-related pathway. The at least one CYP450-family associated with metabolism of one or more of the toxin may influence metabolism directly, such as through acting directly on some component of the toxin or acting in concert with other biological factors on the metabolism of some component of the toxin. In some embodiments, circuitry for identifying at least one CYP450-family enzyme associated with metabolism of one or more of the at least one toxin 140 includes circuitry wherein the at least one CYP450-family enzyme associated with metabolism of one or more of the toxin indirectly metabolizes the toxin. In some embodiments, circuitry for identifying at least one CYP450-family enzyme associated with metabolism of one or more of the at least one toxin 140 includes circuitry wherein the at least one CYP450-family enzyme associated with metabolism of one or more of the toxin is known to metabolize the toxin. In some embodiments, circuitry for identifying at least one CYP450-family enzyme associated with metabolism of one or more of the at least one toxin 140 includes circuitry wherein the at least one CYP450-family enzyme associated with metabolism of one or more of the toxin is hypothesized to metabolize the toxin. In some embodiments, circuitry for identifying at least one modulator of one or more of the at least one CYP450-family enzyme 150 includes circuitry wherein the at least one modulator of one or more of the at least one CYP450-family enzyme is an endogenous modulator 310. An "endogenous modulator," as used herein, includes a modulator that includes components that are endogenous to the individual, such as endogenous proteins, polypeptides, RNA species, or signaling molecules. In some embodiments, circuitry for identifying at least one modulator of one or more of the at least one CYP450-family enzyme 150 includes circuitry wherein the at least one modulator of one or more of the at least one CYP450-family enzyme is an exogenous modulator 320. An "exogenous modulator," as used herein, includes a modulator that includes components that are exogenous to the individual, such as, for example, externally-derived drugs, xenobiotics, compounds, active ingredients or materials. In some aspects, an exogenous modulator may be derived from a biological source, such as a protein or polypeptide that is purified from biological materials. In some embodiments, circuitry for identifying at least one modulator of one or more of the at least one CYP450-family enzyme 150 includes circuitry wherein the at least one modulator of one or more of the at least one CYP450-family enzyme is a synthetic modulator 330. As used herein a "synthetic modulator" includes a compound or component which is entirely synthetic, such as, for example, a chemical compound which is laboratory-derived or chemically created. In some embodiments, a system 100 may include circuitry for communicating the at least one modulator to a system user 340.

FIG. 4 depicts aspects of a system such as the one illustrated in FIG. 1. In some embodiments, a system 100 may include circuitry for communicating the at least one CYP450-family enzyme associated with metabolism of one or more of the at least one toxin to a system user 400. For example, a system may communicate a specific CYP450-family enzyme such as "CYP1A1" or "CYP2D6," or may communicate a class or group of CYP450-family enzymes such as "CYP1B" or "CYP2." In some embodiments, a system 100 may include: circuitry for accepting input identifying at least one variant of the at least one CYP450-family enzyme; circuitry for identifying at least one modulator of the at least one variant; and circuitry for communicating at least one treatment to at least one system user, wherein the treatment includes one or more of the at least one modulator of the at least one variant 410. In some embodiments, circuitry 410 may include circuitry wherein the at least one variant is directly associated with the individual 420. In some embodiments, circuitry 410 may include circuitry wherein the at least one variant is indirectly associated with the individual.

Figure 5:
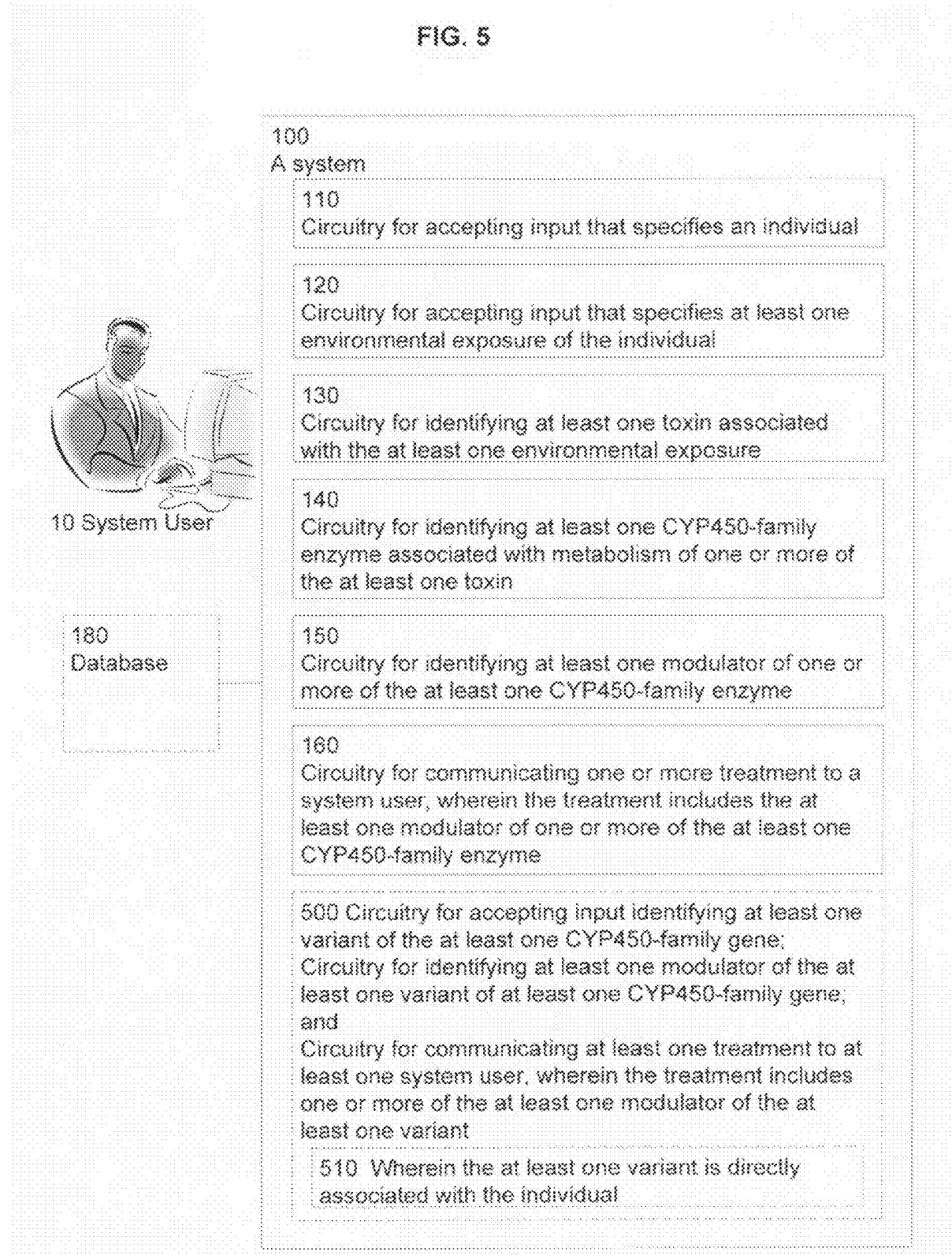
FIG. 5 is a diagram showing some aspects of a system such as the one depicted in FIG. 1.

FIG. 5 shows aspects of a system such as the one depicted in FIG. 1. In some embodiments, a system 100 may include: circuitry for accepting input identifying at least one variant of the at least one CYP450-family gene; circuitry for identifying at least one modulator of the at least one variant of at least one CYP450-family gene; and circuitry for communicating at least one treatment to at least one system user, wherein the treatment includes one or more of the at least one modulator of the at least one variant 500. In some embodiments, circuitry 500 may include circuitry wherein the at least one variant is directly associated with the individual 510. In some embodiments, circuitry 500 may include circuitry wherein the at least one variant is indirectly associated with the individual.

Figure 6:
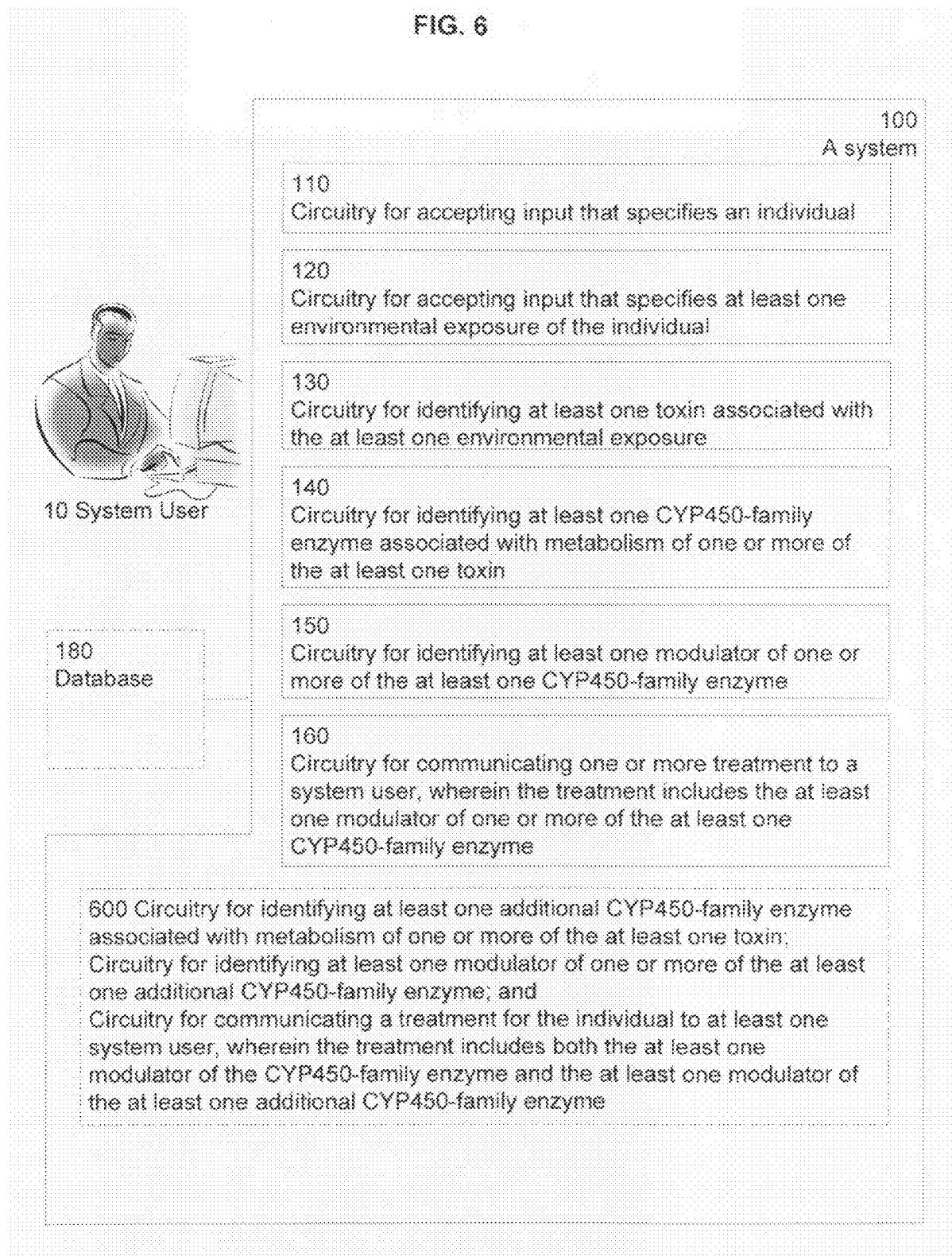
FIG. 6 is a diagram illustrating some aspects of a system such as the one depicted in FIG. 1.

FIG. 6 depicts aspects of a system such as the one illustrated in FIG. 1. In some embodiments, a system 100 includes: circuitry for identifying at least one additional CYP450-family enzyme associated with metabolism of one or more of the at least one toxin; circuitry for identifying at least one modulator of one or more of the at least one additional CYP450-family enzyme; and circuitry for communicating a treatment for the individual to at least one system user, wherein the treatment includes both the at least one modulator of the CYP450-family enzyme and the at least one modulator of the at least one additional CYP450-family enzyme 600.

Figure 7:
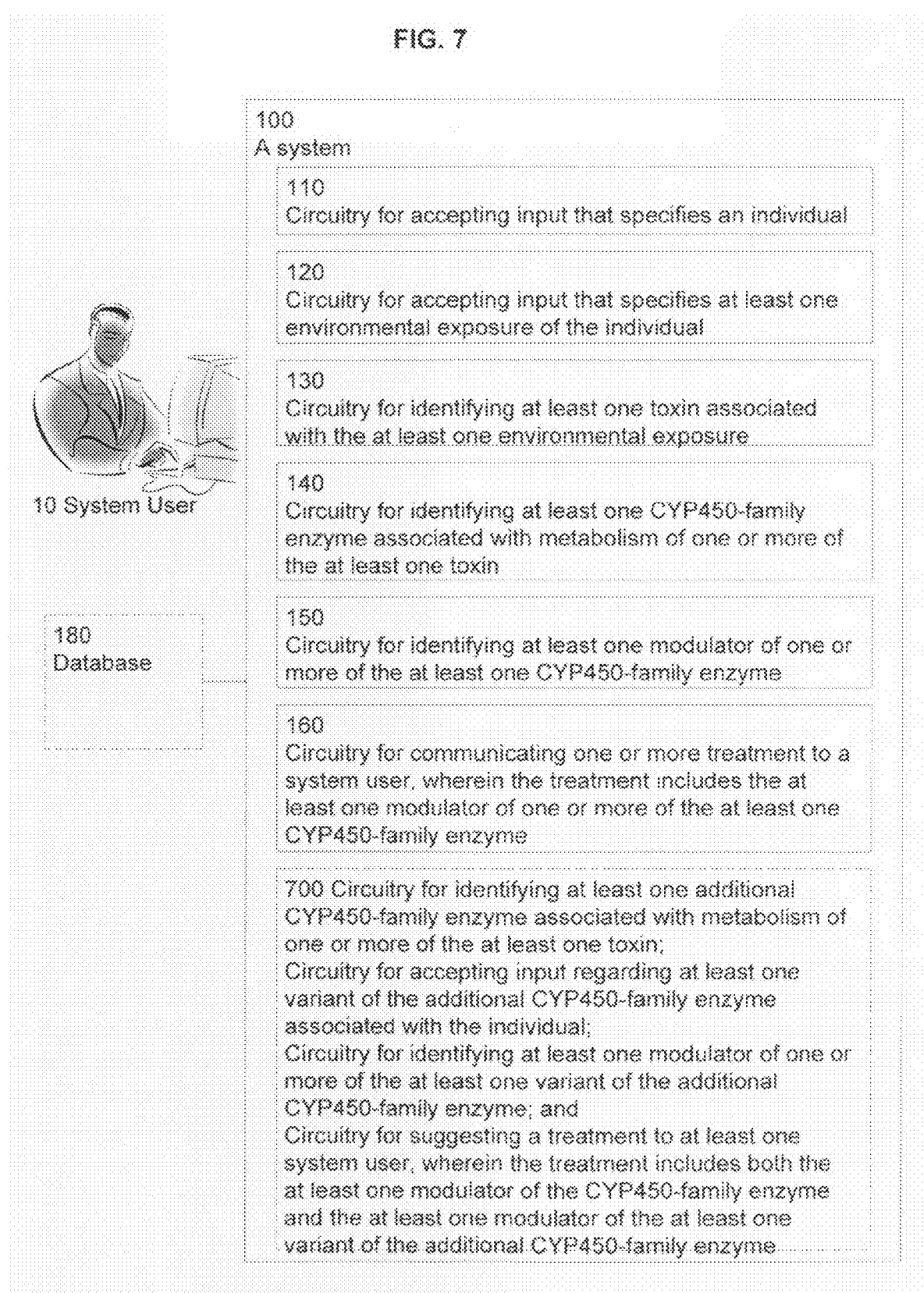
FIG. 7 is a diagram showing some aspects of a system such as the one depicted in FIG. 1.

FIG. 7 shows aspects of a system such as the one depicted in FIG. 1. In some embodiments, a system 100 includes: circuitry for identifying at least one additional CYP450-family enzyme associated with metabolism of one or more of the at least one toxin; circuitry for accepting input regarding at least one variant of the additional CYP450-family enzyme associated with the individual; circuitry for identifying at least one modulator of one or more of the at least one variant of the additional CYP450-family enzyme; and circuitry for suggesting a treatment to at least one system user, wherein the treatment includes both the at least one modulator of the CYP450-family enzyme and the at least one modulator of the at least one variant of the additional CYP450-family enzyme 700.

Figure 8:
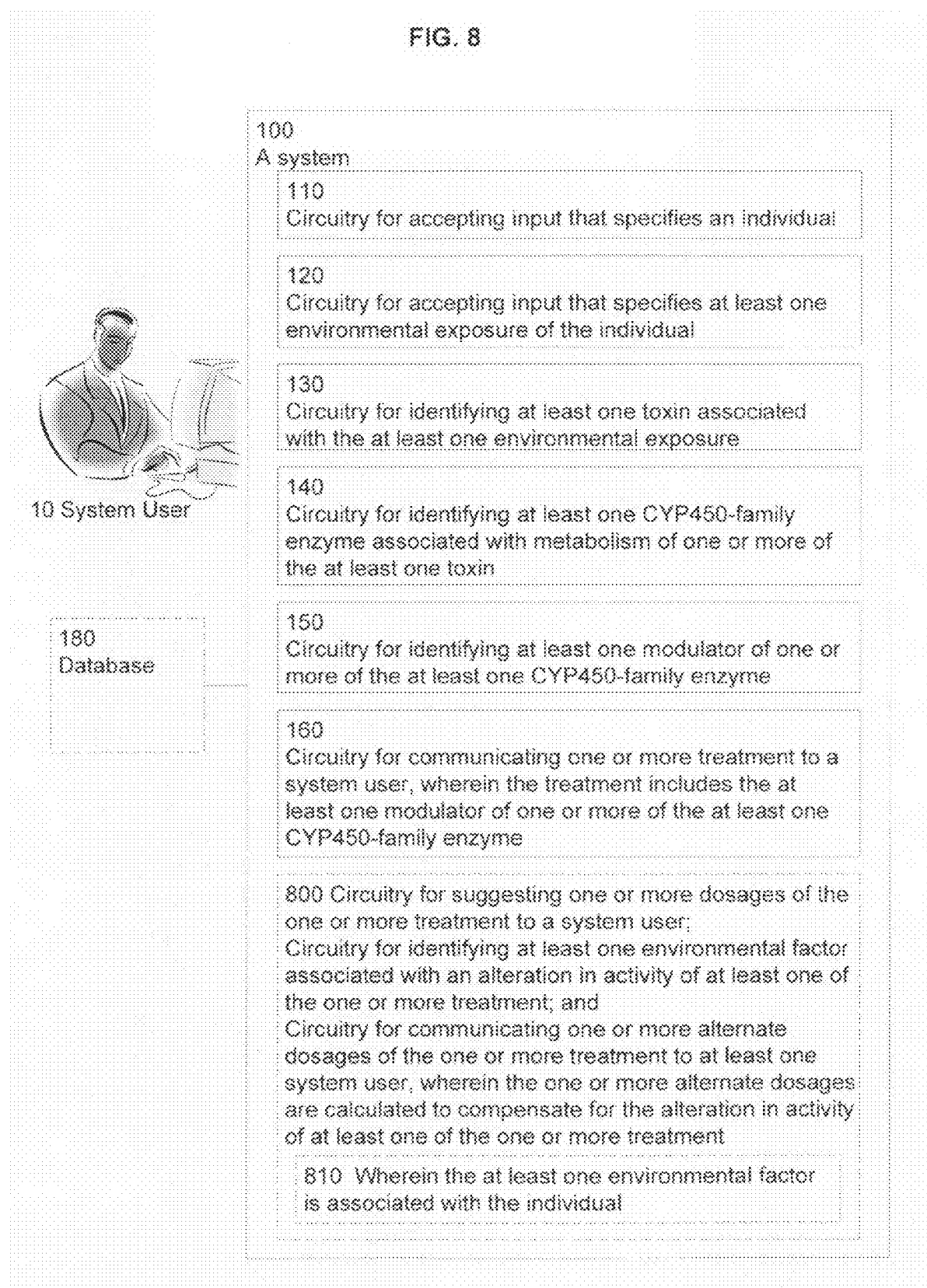
FIG. 8 is a diagram illustrating some aspects of a system such as the one depicted in FIG. 1.

FIG. 8 shows aspects of a system such as the one illustrated in FIG. 1. In some embodiments, a system 100 may include: circuitry for suggesting one or more dosages of the one or more treatment to a system user; circuitry for identifying at least one environmental factor associated with an alteration in activity of at least one of the one or more treatment; and circuitry for communicating one or more alternate dosages of the one or more treatment to at least one system user, wherein the one or more alternate dosages are calculated to compensate for the alteration in activity of at least one of the one or more treatment 800. In some embodiments, circuitry 800 may include circuitry wherein the at least one environmental factor is associated with the individual 810. In some embodiments, circuitry 800 may include circuitry wherein the at least one environmental factor is directly associated with the individual. In some embodiments, circuitry 800 may include circuitry wherein the at least one environmental factor is indirectly associated with the individual. In some embodiments, circuitry 800 may include circuitry wherein the at least one environmental factor is not associated with the individual.

FIG. 9 depicts aspects of a system such as the one shown in FIG. 1. In some embodiments, a system 100 includes: circuitry for suggesting one or more dosages of the one or more treatment to a system user; circuitry for identifying at least one dietary factor associated with an alteration in activity of at least one of the one or more treatment; and circuitry for communicating one or more alternate dosages of the one or more treatment to at least one system user, wherein the one or more alternate dosages are calculated to compensate for the alteration in activity of at least one of the one or more treatment 900. In some embodiments, circuitry 900 includes circuitry wherein the at least one dietary factor is associated with the individual 910. In some embodiments, circuitry 900 includes circuitry wherein the at least one dietary factor is directly associated with the individual. In some embodiments, circuitry 900 includes circuitry wherein the at least one dietary factor is indirectly associated with the individual. In some embodiments, circuitry 900 includes circuitry wherein the at least one dietary factor is not associated with the individual. In some embodiments, a system 100 includes: circuitry for associating at least one anatomic location with predicted activity of the at least one CYP450-family enzyme; circuitry for associating the at least one anatomic location with one or more of the at least one modulator; and circuitry for communicating at least one treatment to a system user, wherein the treatment includes the at least one modulator of the at least one CYP450-family enzyme associated with the at least one anatomic location 920. An anatomic location, as used herein, may include a body part, tissue, or portions thereof (e.g. "the liver" or "the aorta" or "the vasculature").

Figure 10:
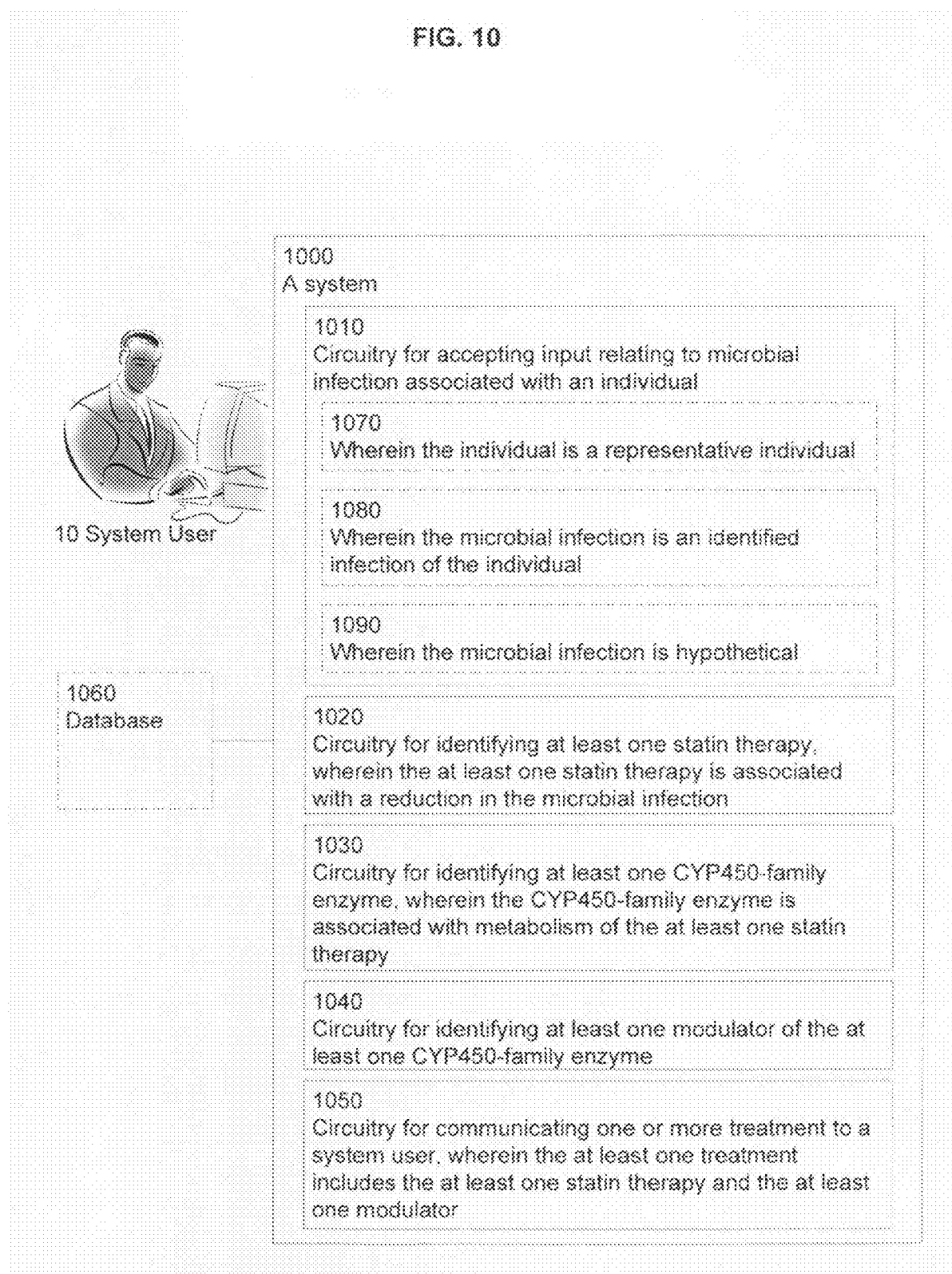
FIG. 10 is a diagram illustrating some aspects of a system.

FIG. 10 shows aspects of a system. A system 1000 includes circuitry for accepting input relating to microbial infection associated with an individual 1010. In some embodiments, circuitry 1010 includes circuitry wherein the individual is a representative individual 1070. In some embodiments, circuitry 1010 includes circuitry wherein the individual is a specified individual. In some embodiments, circuitry 1010 includes circuitry wherein the individual is identified via membership in a group or population. In some embodiments, circuitry 1010 includes circuitry wherein the individual is associated with a group, another individual or a location. In some embodiments, circuitry 1010 includes circuitry wherein the microbial infection is an identified infection of the individual 1080. In some embodiments, circuitry 1010 includes circuitry wherein the microbial infection is a suspected infection of the individual. In some embodiments, circuitry 1010 includes circuitry wherein the microbial infection is a hypothetical infection of the individual. For example, the microbial infection may be known to exist and potentially infect the individual, but evidence is lacking to clearly state that the individual is infected. In some embodiments, circuitry 1010 includes circuitry wherein the microbial infection is hypothetical 1090. For example, the microbial infection may not be known to exist or may not be known to exist in a location where the individual may be exposed to the microbial infection. A system 1000 includes circuitry for identifying at least one statin therapy, wherein the at least one statin therapy is associated with a reduction in the microbial infection 1020. A system 1000 includes circuitry for identifying at least one CYP450-family enzyme, wherein the CYP450-family enzyme is associated with metabolism of the at least one statin therapy 1030. A system 1000 includes circuitry for identifying at least one modulator of at least one CYP450-family enzyme 1040. A system 1000 includes circuitry for communicating one or more treatment to a system user, wherein the at least one treatment includes that at least one statin therapy and the at least one modulator 1050. In some embodiments, a system 1000 may include a database 1060. A system 1000 may accept input and communicate with a system user 10.

As used herein, "microbial" includes agents which are microscopic, such as prokaryotes and smaller eukaryotes. Microbial may include bacteria, including bacteria and archaea species. Microbial may include protists and fungi. In some instances, microbial may include microscopic plants, including algae. For example, microbial may include gram-positive cocci, such as *staphylococcus, streptococcus* and *enterococcus* species. For example, microbial may include the spirochete *Borrelia burgdorferi*. For example, microbial may include bacteria such as *Bacillus subtilis* and *Escherichia coli*. For example, microbial may include *Pseudomonas mevalonii, Archaeoglobus fulgidus, Staphylococcus aureus, Streptococcus pneumoniae, Enterococcus faecalis*, and *Enterococcus faecalis* species.

As used herein, a statin therapy includes therapies that include at least one drug in the statin family, including hydroxylmethylglutaryl-CoA (HMG-CoA) reductase inhibitors. For example, a statin therapy may include one or more of: atorvastatin, cerivastatin, lovastatin, fluvastatin, cerivastatin, pravastatin or simvastatin. A CYP450-family enzyme may be associated with metabolism of the statin therapy. For example, atorvastatin, cerivastatin, lovastatin and simvastatin are metabolized primarily by CYP3A4; fluvastatin is metabolized mainly by CYP2C9; cerivastatin is metabolized by CYP3A4 and CYP2C8 and pravastatin is not extensively metabolized (see, e.g. Beaird, HMG-CoA reductase inhibitors: assessing differences in drug interactions and safety profiles, Am. Pharm. Assoc. 40: 637-644, 2000; which is incorporated by reference herein). A statin therapy may be associated with a reduction in a microbial infection. For example, a statin therapy may be associated with a reduction in microbial infection through biochemical analysis, in vivo, in vitro or population-based studies. See, for example: de Rego, Simvastatin improves the healing of infected skin wounds of rats, Acta Cirfúrgica Basileria, 22: 57-63, 2007; Hedl, Inhibition of the class II HMG-CoA reductase of *Pseudomonas mevalonii*, Protein Science 13, 1693-1697, 2004; Taberno, Crystal structure of a statin bound to a class II hydroxymetylglutaryl-CoA reductase, Journal of Biological Chemistry, 278, 19933-19938, 2003; and Wilding, Identification, evolution, and essentiality of the mevalonate pathway for isopentenyl diphospate biosynthesis in gram-positive cocci, Journal of Bacteriology, 182, 4319-4327, 2000, which are incorporated by reference herein.

Figure 11:
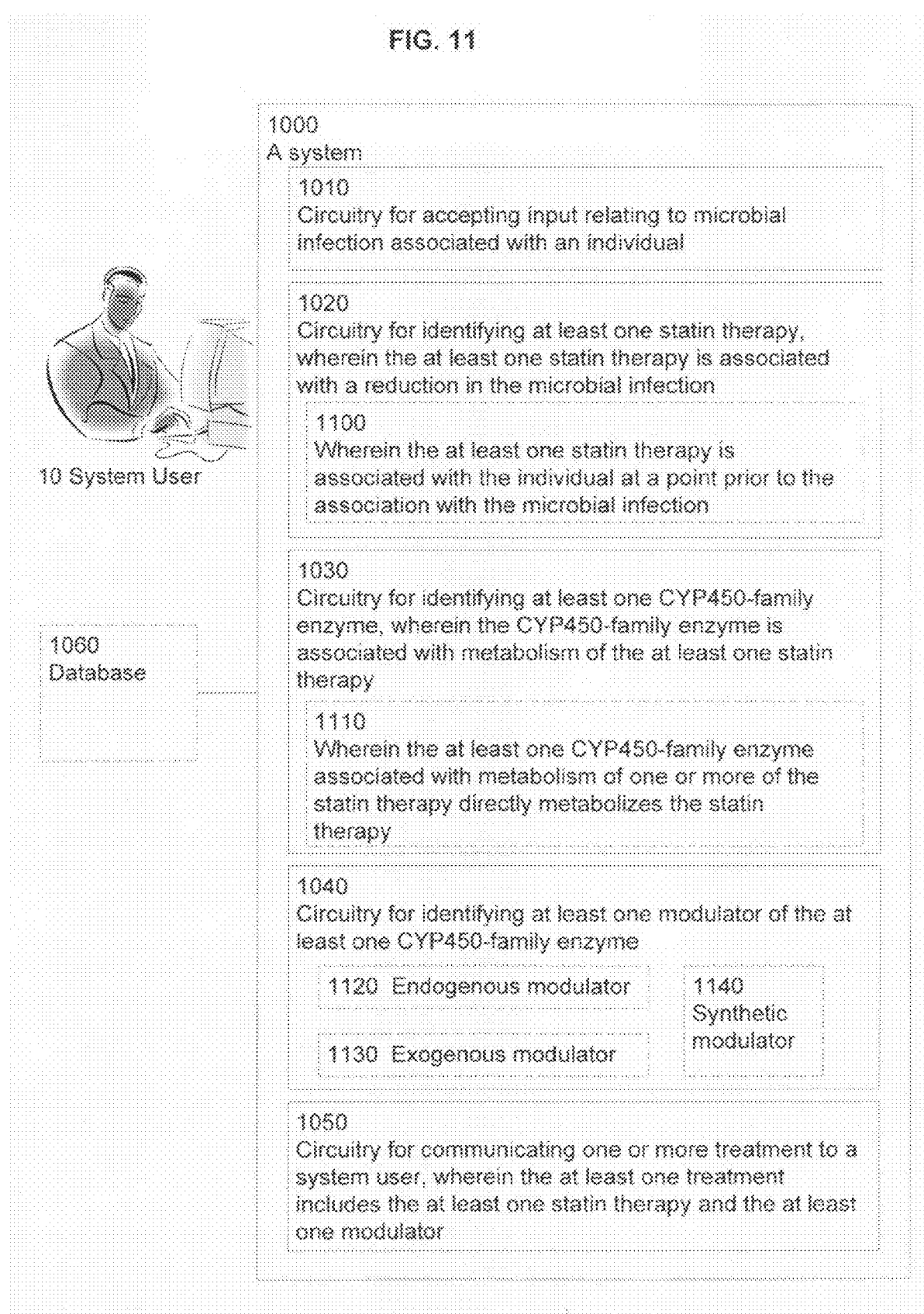
FIG. 11 is a diagram showing some aspects of a system such as the one depicted in FIG. 10.

FIG. 11 shows aspects of a system such as the one illustrated in FIG. 10. In some embodiments, circuitry 1020 may include circuitry wherein the at least one statin therapy is associated with the individual at a point prior to the association with the microbial infection 1100. In some embodiments, circuitry 1020 may include circuitry wherein the at least one statin therapy is associated with the individual at after the association with the microbial infection. In some embodiments, circuitry 1020 may include circuitry wherein the at least one statin therapy is associated with the individual after the association with the microbial infection is identified. In some embodiments, circuitry 1020 may include circuitry wherein the at least one statin therapy is associated with the individual in response to the association with the microbial infection. In some embodiments, circuitry 1030 includes circuitry wherein the at least one CYP450-family enzyme associated with metabolism of one or more of the statin therapy directly metabolizes the statin therapy 1110. In some embodiments, circuitry 1030 includes circuitry wherein the at least one CYP450-family enzyme associated with metabolism of one or more of the statin therapy indirectly metabolizes the statin therapy. In some embodiments, circuitry 1040 includes circuitry wherein the at least one modulator of one or more of the at least one CYP450-family enzyme is an endogenous modulator 1120. In some embodiments, circuitry 1040 includes circuitry wherein the at least one modulator of one or more of the at least one CYP450-family enzyme is an exogenous modulator 1130. In some embodiments, circuitry 1040 includes circuitry wherein the at least one modulator of one or more of the at least one CYP450-family enzyme is a synthetic modulator 1140.

Figure 12:
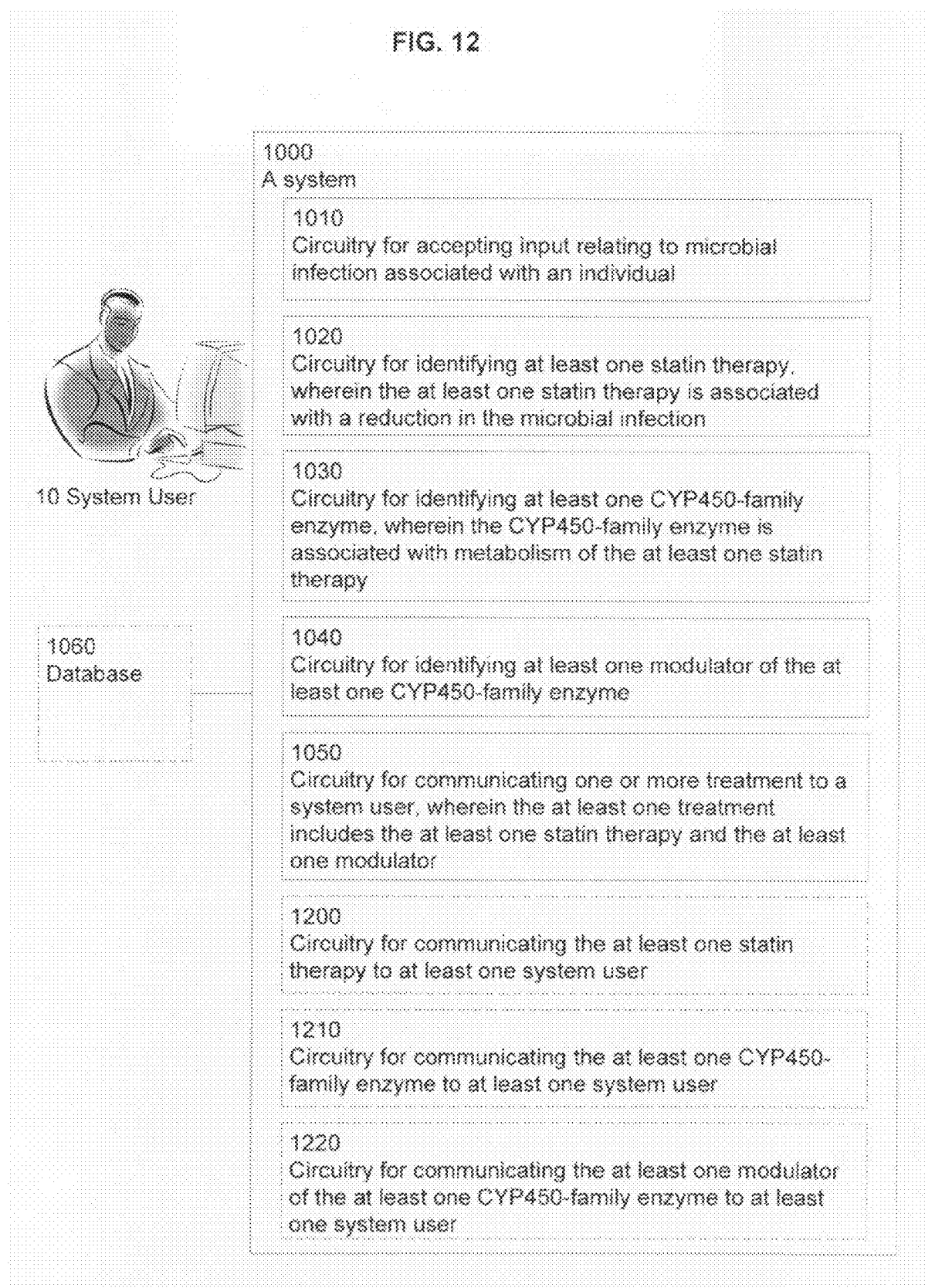
FIG. 12 is a diagram illustrating some aspects of a system such as the one depicted in FIG. 10.

FIG. 12 depicts aspects of a system such as the one illustrated in FIG. 10. In some embodiments, a system 1000 includes circuitry for communicating the at least one statin therapy to at least one system user 1200. In some embodiments, a system 1000 includes circuitry for communicating the at least one CYP450-family enzyme to at least one system user 1210. In some embodiments, a system 1000 includes circuitry for communicating the at least one modulator of the at least one CYP450-family enzyme to at least one system user 1220.

Figure 13:
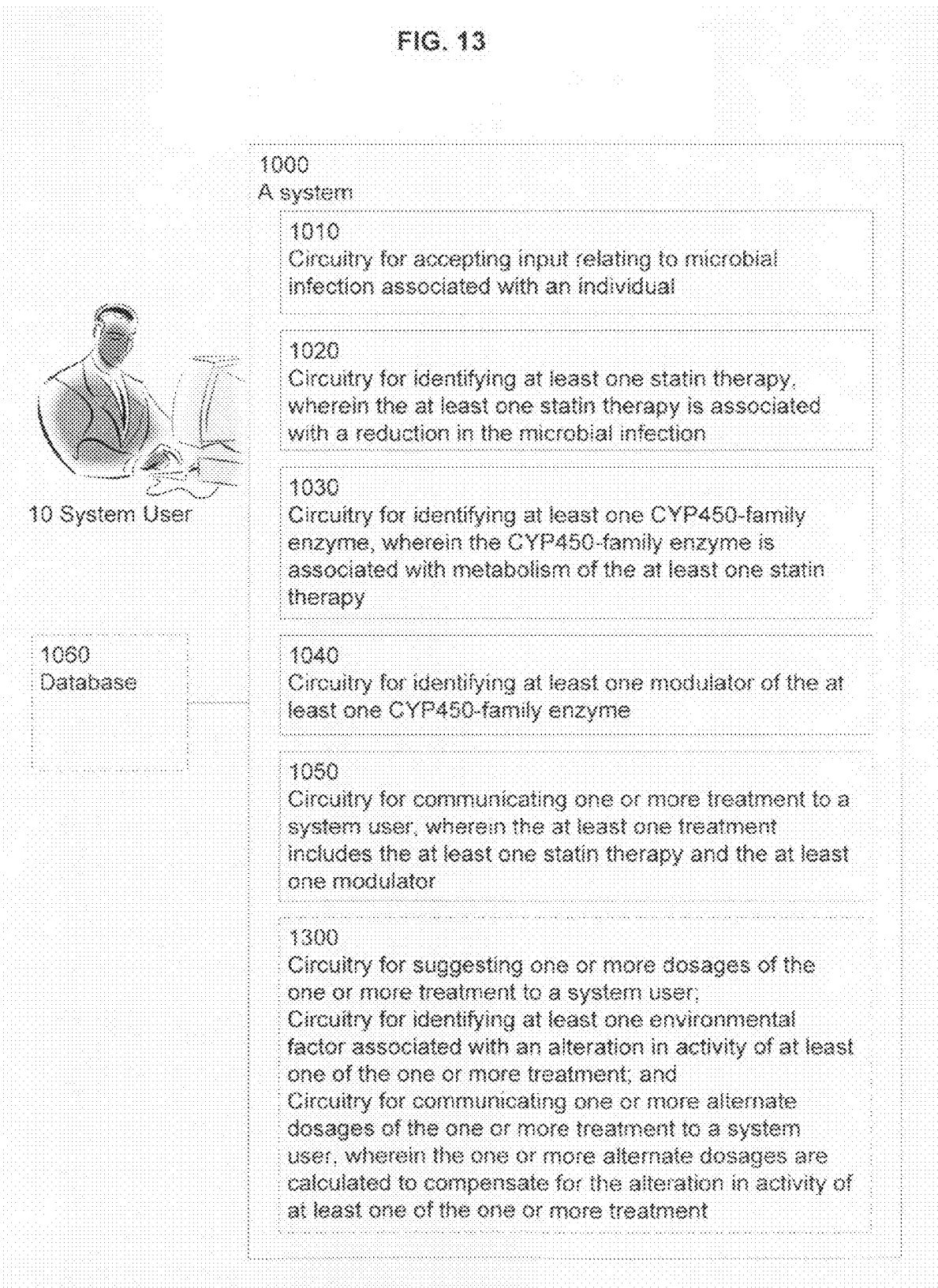
FIG. 13 is a diagram showing some aspects of a system such as the one depicted in FIG. 10.

FIG. 13 shows aspects of a system such as those illustrated in FIG. 10. In some embodiments, a system 1000 includes: circuitry for suggesting one or more dosages of the one or more treatment to a system user; circuitry for identifying at least one environmental factor associated with an alteration in activity of at least one of the one or more treatment; and circuitry for communicating one or more alternate dosages of the one or more treatment to a system user, wherein the one or more alternate dosages are calculated to compensate for the alteration in activity of at least one of the one or more treatment 1300.

FIG. 14 shows aspects of a system such as the one illustrated in FIG. 10. In some embodiments, a system 1000 includes: circuitry for suggesting one or more dosages of the one or more treatment to a system user; circuitry for identifying at least one dietary factor associated with an alteration in activity of at least one of the one or more treatment; and circuitry for communicating one or more alternate dosages of the one or more treatment to a system user, wherein the one or more alternate dosages are calculated to compensate for the alteration in activity of at least one of the one or more treatment 1400. In some embodiments, a system 1000 includes circuitry for communicating at least one treatment to a system user, wherein the treatment includes one or more of the at least one statin therapy and one or more of the at least one modulator 1410.

Figure 15:
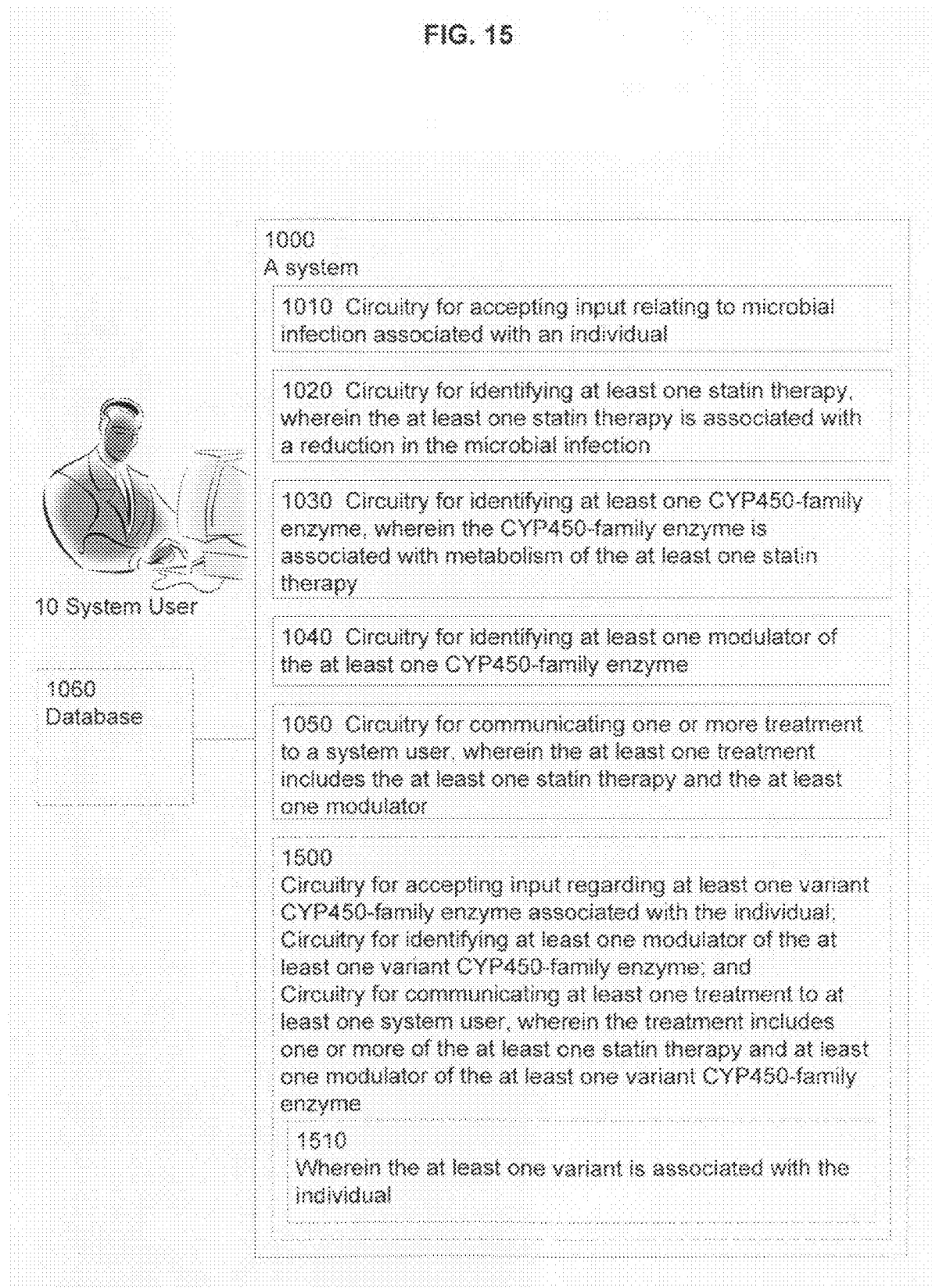
FIG. 15 is a diagram showing some aspects of a system such as the one depicted in FIG. 10.

FIG. 15 depicts aspects of a system such as the one shown in FIG. 10. In some embodiments, a system 1000 may include: circuitry for accepting input regarding at least one variant CYP450-family enzyme associated with the individual; circuitry for identifying at least one modulator of the at least one variant CYP450-family enzyme; and circuitry for communicating at least one treatment to at least one system user, wherein the treatment includes one or more of the at least one statin therapy and at least one modulator of the at least one variant CYP450-family enzyme 1500. In some embodiments circuitry 1500 may include circuitry wherein the at least one variant is associated with the individual 1510. In some embodiments circuitry 1500 may include circuitry wherein the at least one variant is directly associated with the individual. In some embodiments circuitry 1500 may include circuitry wherein the at least one variant is indirectly associated with the individual.

Figure 16:
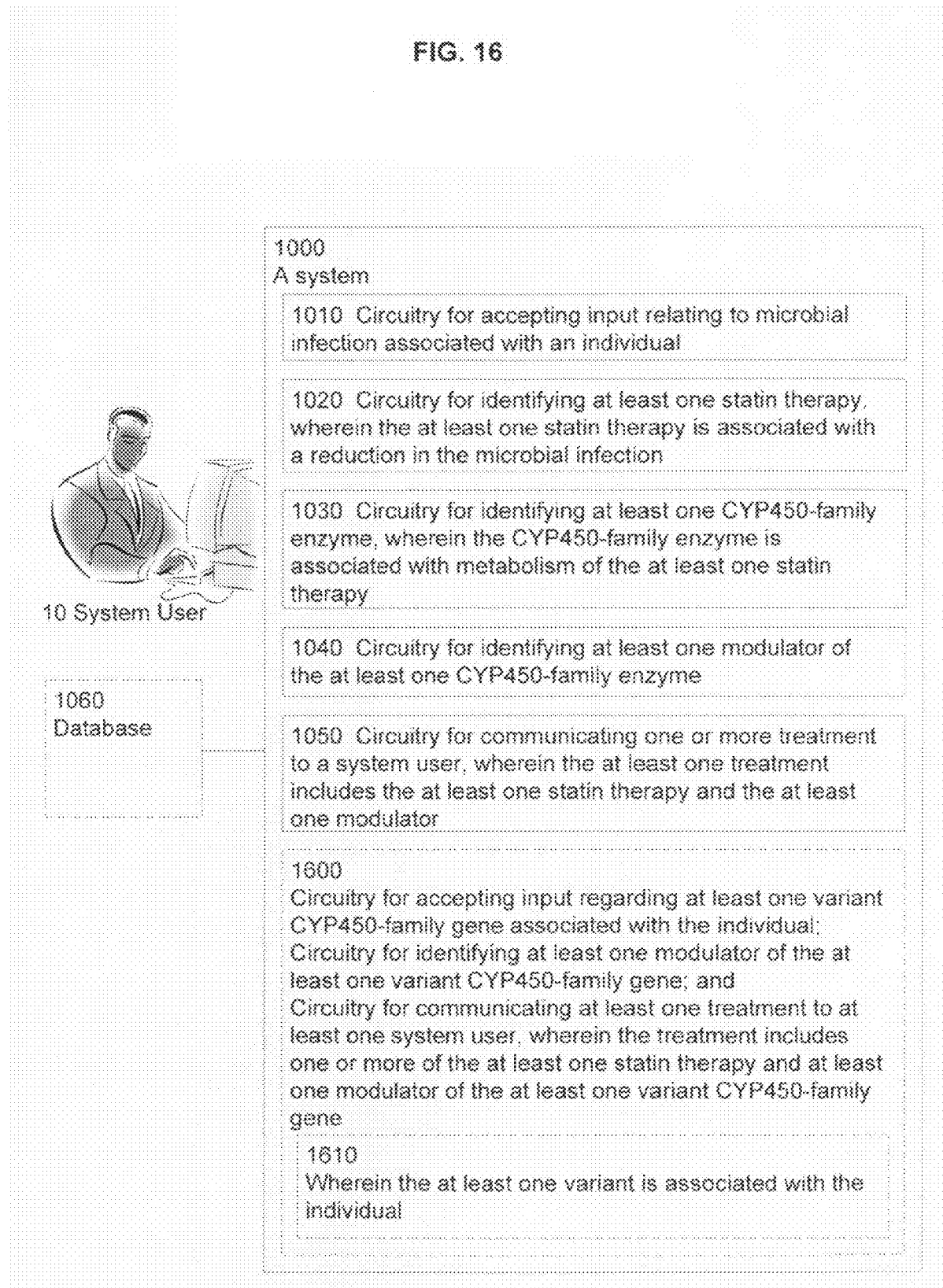
FIG. 16 is a diagram illustrating some aspects of a system such as the one depicted in FIG. 10.

FIG. 16 depicts aspects of a system such as the one illustrated in FIG. 10. In some embodiments, a system 1000 may include: circuitry for accepting input regarding at least one variant CYP450-family gene associated with the individual; circuitry for identifying at least one modulator of the at least one variant CYP450-family gene; and circuitry for communicating at least one treatment to at least one system user, wherein the treatment includes one or more of the at least one statin therapy and at least one modulator of the at least one variant CYP450-family gene 1600. In some embodiments circuitry 1600 may include circuitry wherein the at least one variant is associated with the individual 1610. In some embodiments circuitry 1600 may include circuitry wherein the at least one variant is directly associated with the individual. In some embodiments circuitry 1600 may include circuitry wherein the at least one variant is indirectly associated with the individual.

Figure 17:
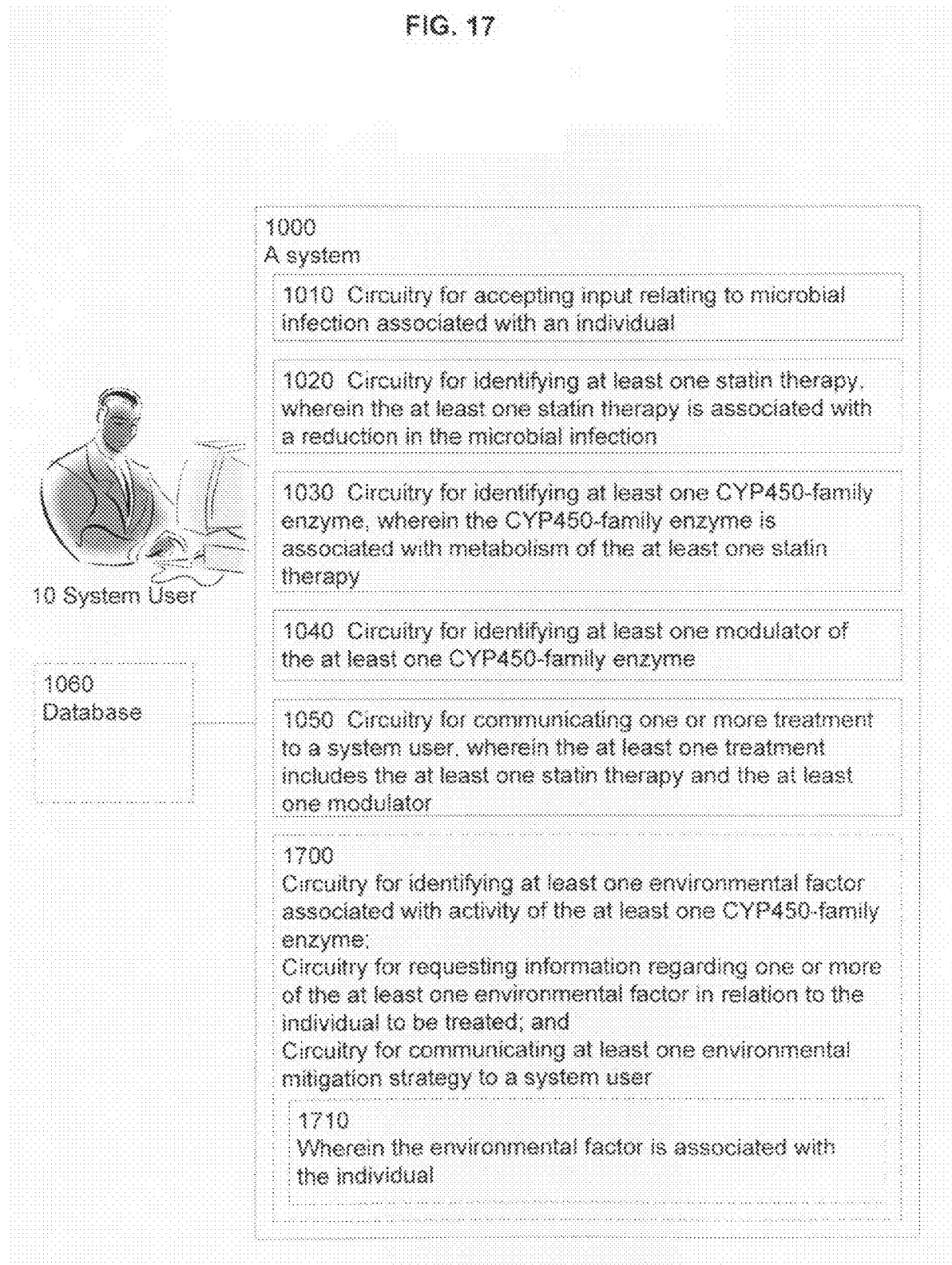
FIG. 17 is a diagram showing some aspects of a system such as the one depicted in FIG. 10.

FIG. 17 illustrates aspects of a system such as the one depicted in FIG. 10. In some embodiments, a system 100 may include: circuitry for identifying at least one environmental factor associated with activity of the at least one CYP450-family enzyme; circuitry for requesting information regarding one or more of the at least one environmental factor in relation to the individual to be treated; and circuitry for communicating at least one environmental mitigation strategy to a system user 1700. For example, at least one environmental factor may include pollutants, carcinogens, food additives, or gases. One or more of the at least one environmental factor may include factors that are predicted to be internalized by an individual, such as, for example, factors that may be ingested, absorbed transdermally, or inhaled. For example, an environmental mitigation strategy may include avoidance or mitigation or the at least one environmental factor. For example, an environmental mitigation strategy may include avoidance of a location where an environmental factor is present, avoidance of ingesting a liquid or substance which includes the environmental factor, or removal of an environmental factor. For example, an environmental mitigation strategy may include avoiding a contaminated region, avoiding consuming a specific food or liquid from a source, or breathing air that has been filtered to remove one or more environmental factors. In some embodiments, circuitry 1700 may include circuitry wherein the environmental factor is associated with the individual 1710. In some embodiments, circuitry 1700 may include circuitry wherein the environmental factor is directly associated with the individual. In some embodiments, circuitry 1700 may include circuitry wherein the environmental factor is indirectly associated with the individual.

Figure 18:
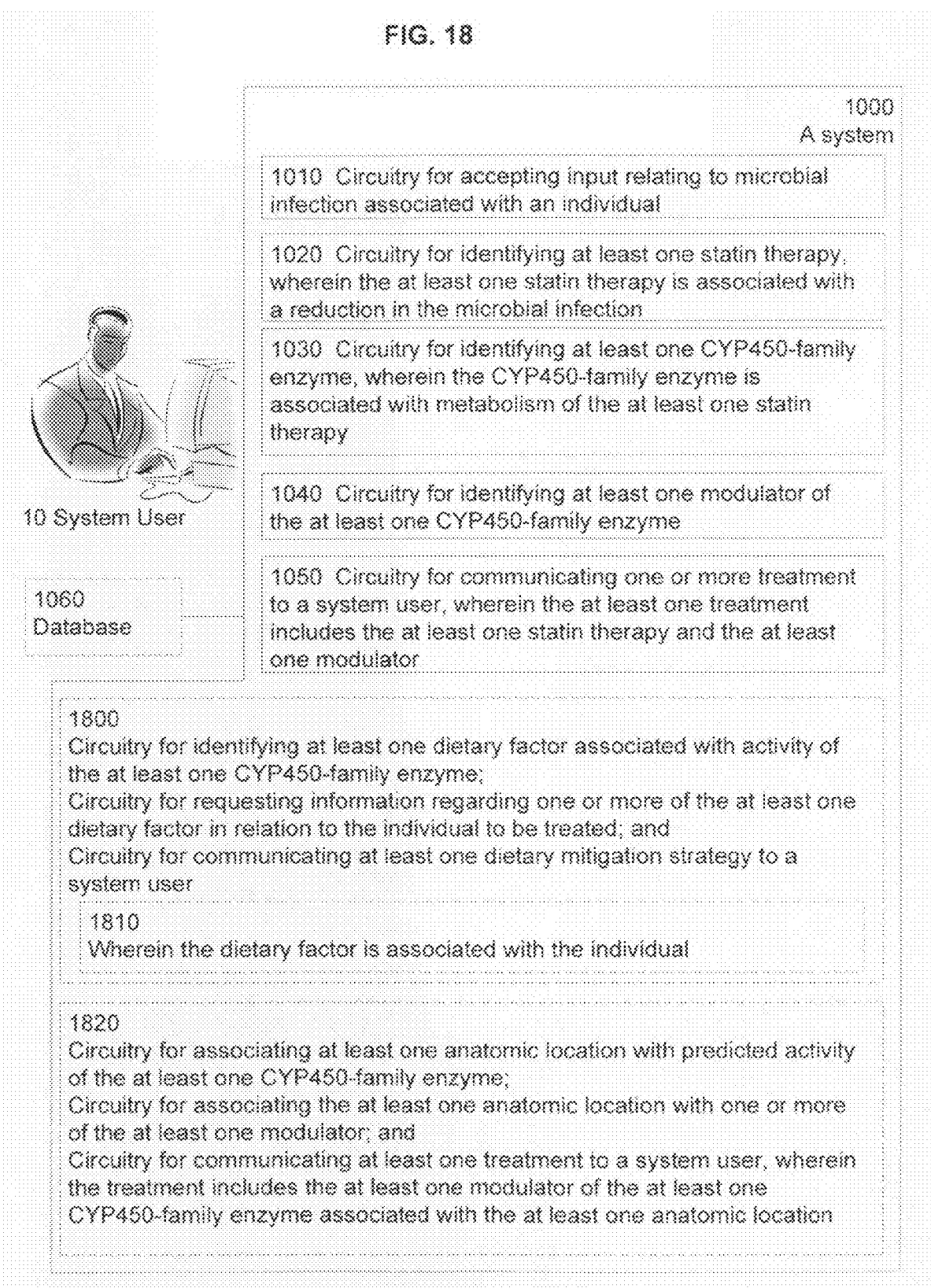
FIG. 18 is a diagram illustrating some aspects of a system such as the one depicted in FIG. 10.

FIG. 18 depicts aspects of a system such as the one illustrated in FIG. 10. In some embodiments, a system 1000 includes: circuitry for identifying at least one dietary factor associated with activity of the at least one CYP450-family enzyme; circuitry for requesting information regarding one or more of the at least one dietary factor in relation to the individual to be treated; and circuitry for communicating at least one dietary mitigation strategy to a system user 1800. In some embodiments, circuitry 1800 may include circuitry wherein the dietary factor is associated with the individual 1810. In some embodiments, circuitry 1800 may include circuitry wherein the dietary factor is directly associated with the individual. In some embodiments, circuitry 1800 may include circuitry wherein the dietary factor is indirectly associated with the individual. A system 1000 may include: circuitry for associating at least one anatomic location with predicted activity of the at least one CYP450-family enzyme; circuitry for associating the at least one anatomic location with one or more of the at least one modulator; and circuitry for communicating at least one treatment to a system user, wherein the treatment includes the at least one modulator of the at least one CYP450-family enzyme associated with the at least one anatomic location 1820.

Figure 19:
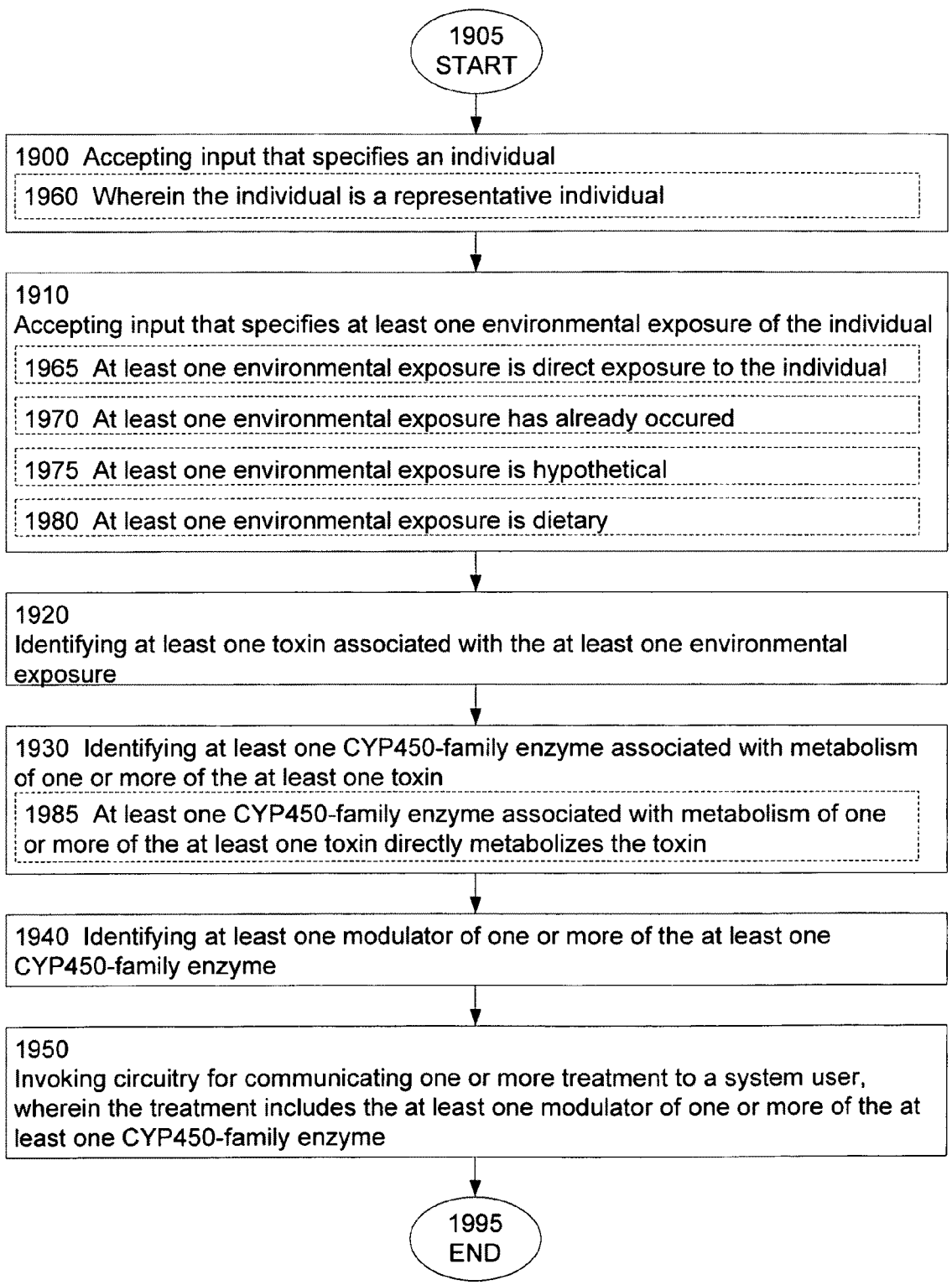
FIG. 19 is a flowchart depicting aspects of a method.

FIG. 19 shows aspects of a method. The method start is depicted with block 1905. It should be noted that any method blocks depicted herein as "start" or "stop" or "end" are for illustrative purposes and do not necessarily mean that the described method must "start" or "end" at a specified method block, or that there are no other method steps contemplated either prior to "start" or after "end" or "stop." The described method could be incorporated into or within another method, for example. Method block 1900 depicts accepting input that specifies an individual. Method block 1900 may include block 1960, illustrating wherein the individual is a representative individual. Method block 1910 shows accepting input that specifies at least one environmental exposure of the individual. Method block 1910 may include one or more of blocks 1965, 1970, 1975, or 1980. Method block 1965 depicts wherein at least one environmental exposure is direct exposure to the individual. Method block 1970 shows wherein at least one environmental exposure has already occurred. Method block 1975 illustrates wherein at least one environmental exposure is hypothetical. Method block 1980 shows wherein at least one environmental exposure is dietary. Method block 1920 depicts identifying at least one toxin associated with the at least one environmental exposure. Method block 1930 shows identifying at least one CYP450-family enzyme associated with metabolism of one or more of the at least one toxin. Method block 1930 may include method block 1985, illustrating wherein at least one CYP450-family enzyme associated with metabolism of one or more of the at least one toxin directly metabolizes the toxin. Method block 1940 illustrates identifying at least one modulator of one or more of the at least one CYP450-family enzyme. Method block 1950 shows invoking circuitry for communicating one or more treatment to a system user, wherein the treatment includes the at least one modulator of one or more of the at least one CYP450-family enzyme. In some embodiments, one or more steps of a method may be implemented by circuitry, or a computing device. In some embodiments, one or more steps of a method may be performed by or on a computing device or performed by or on circuitry. In some embodiments, one or more steps of a method may invoke circuitry. The method end is depicted by block 1995.

Figure 20:
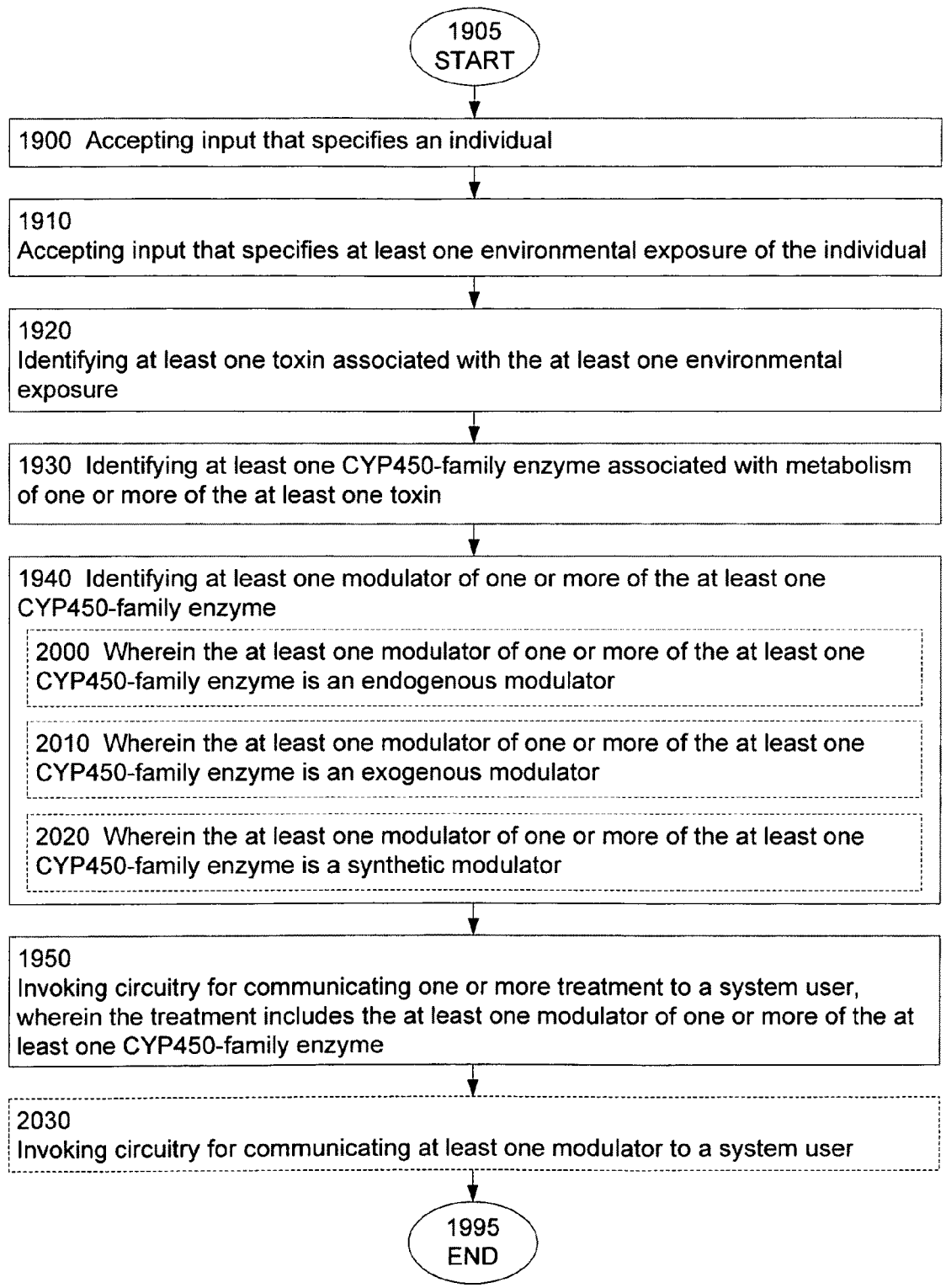
FIG. 20 is a flowchart depicting aspects of a method such as the one shown in FIG. 19.

FIG. 20 shows aspects of a method as depicted in FIG. 19. A method diagram may include block 2030, depicting invoking circuitry for communicating at least one modulator to a system user. Method block 1940 may include one or more of method blocks 2000, 2010 and 2020. Method block 2000 depicts wherein the at least one modulator of one or more of the at least one CYP450-family enzyme is an endogenous modulator. Method block 2010 depicts wherein the at least one modulator of one or more of the at least one CYP450-family enzyme is an exogenous modulator. Method block 2020 depicts wherein the at least one modulator of one or more of the at least one CYP450-family enzyme is a synthetic modulator.

Figure 21:
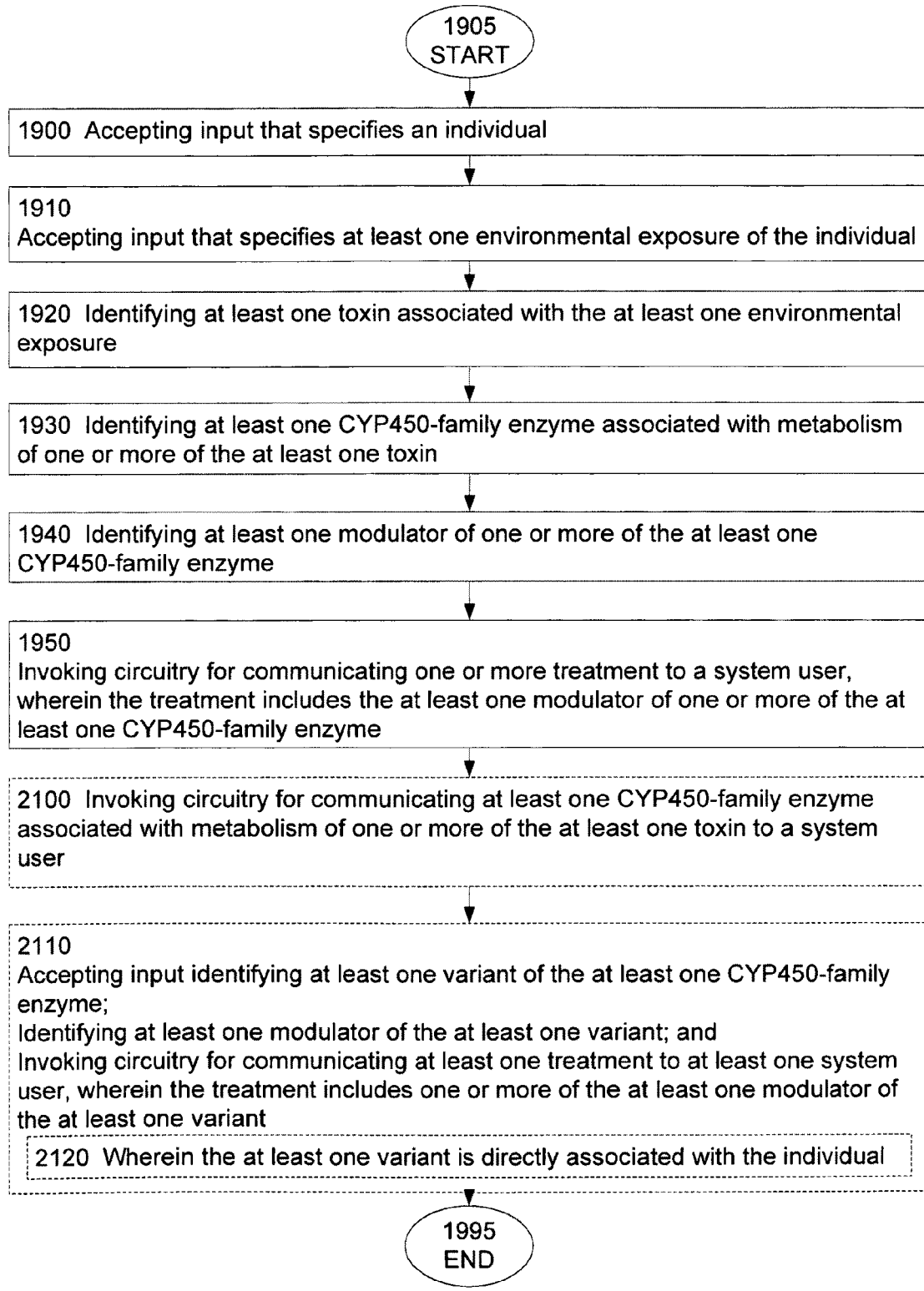
FIG. 21 is a flowchart illustrating aspects of a method such as the one depicted in FIG. 19.

FIG. 21 shows aspects of a system such as the one illustrated in FIG. 19. A method diagram may include block 2100, illustrating invoking circuitry for communicating at least one CYP450-family enzyme associated with metabolism of one or more of the at least one toxin to a system user. A method diagram may include block 2110, showing: accepting input identifying at least one variant of the at least one CYP450-family enzyme; identifying at least one modulator of the at least one variant; and invoking circuitry for communicating at least one treatment to at least one system user, wherein the treatment includes one or more of the at least one modulator of the at least one variant. Block 2110 may include block 2120, depicting wherein the at least one variant is directly associated with the individual.

Figure 22:
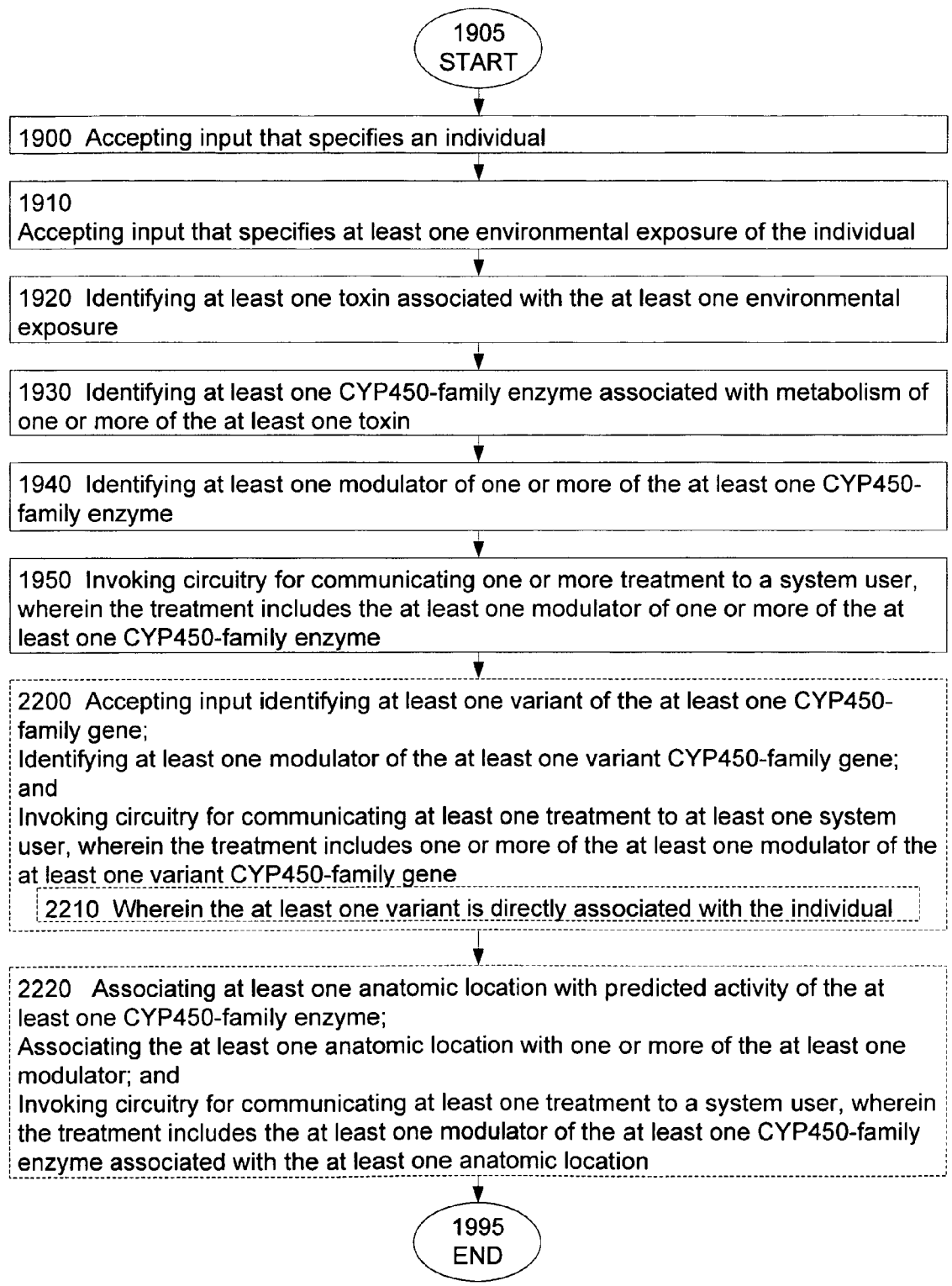
FIG. 22 is a flowchart depicting aspects of a method such as the one shown in FIG. 20.

FIG. 22 illustrates aspects of a method such as the one depicted in FIG. 19. A method diagram may include block 2200, showing: accepting input identifying at least one variant of the at least one CYP450-family gene; identifying at least one modulator of the at least one variant CYP450-family gene; and invoking circuitry for communicating at least one treatment to at least one system user, wherein the treatment includes one or more of the at least one modulator of the at least one variant CYP450-family gene. Block 2200 may include block 2210, showing wherein the at least one variant is directly associated with the individual. A method diagram may include block 2220, depicting: associating at least one anatomic location with predicted activity of the at least one CYP450-family enzyme; associating the at least one anatomic location with one or more of the at least one modulator; and invoking circuitry for communicating at least one treatment to a system user, wherein the treatment includes the at least one modulator of the at least one CYP450-family enzyme associated with the at least one anatomic location.

Figure 23:
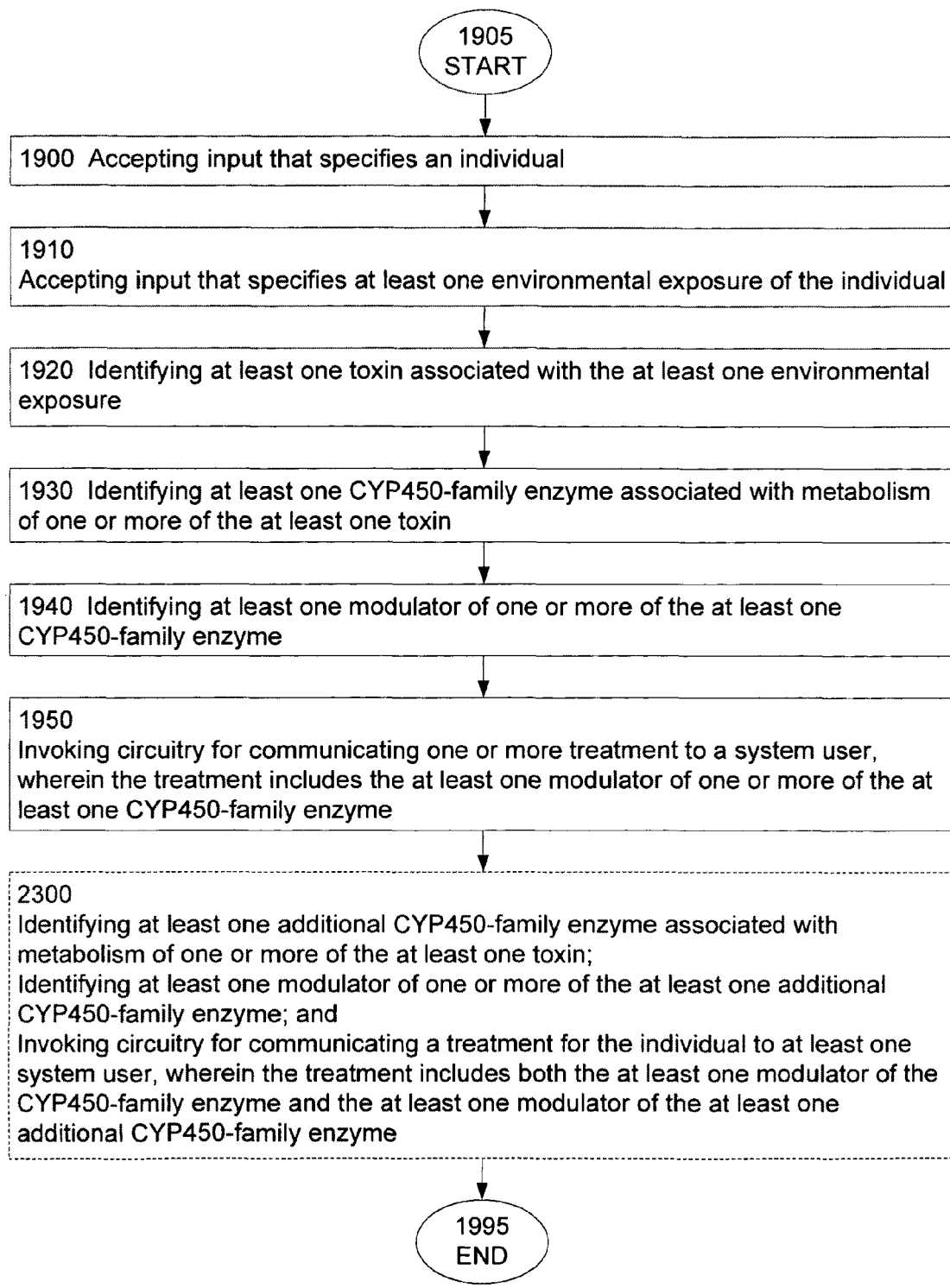
FIG. 23 is a flowchart illustrating aspects of a method such as the one depicted in FIG. 21.

FIG. 23 shows aspects of a method such as the one illustrated in FIG. 19. A method diagram may include block 2300, showing: identifying at least one additional CYP450-family enzyme associated with metabolism of one or more of the at least one toxin; identifying at least one modulator of one or more of the at least one additional CYP450-family enzyme; and invoking circuitry for communicating a treatment for the individual to at least one system user, wherein the treatment includes both the at least one modulator of the CYP450-family enzyme and the at least one modulator of the at least one additional CYP450-family enzyme.

Figure 24:
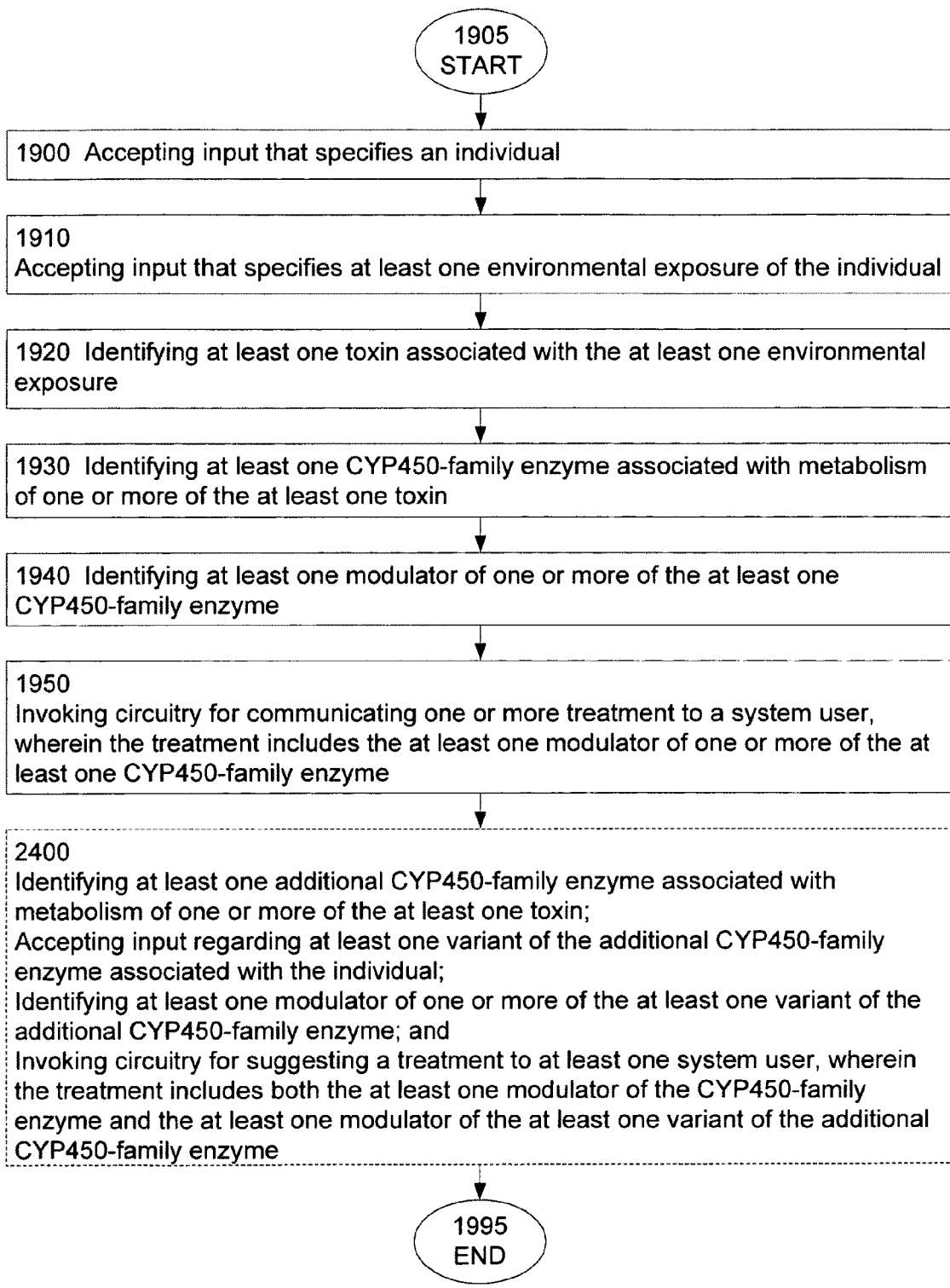
FIG. 24 is a flowchart depicting aspects of a method such as the one shown in FIG. 22.

FIG. 24 depicts aspects of a method such as the one illustrated in FIG. 19. A method diagram may include block 2400, depicting: identifying at least one additional CYP450-family enzyme associated with metabolism of one or more of the at least one toxin; accepting input regarding at least one variant of the additional CYP450-family enzyme associated with the individual; identifying at least one modulator of one or more of the at least one variant of the additional CYP450-family enzyme; and invoking circuitry for suggesting a treatment to at least one system user, wherein the treatment includes both the at least one modulator of the CYP450-family enzyme and the at least one modulator of the at least one variant of the additional CYP450-family enzyme.

Figure 25:
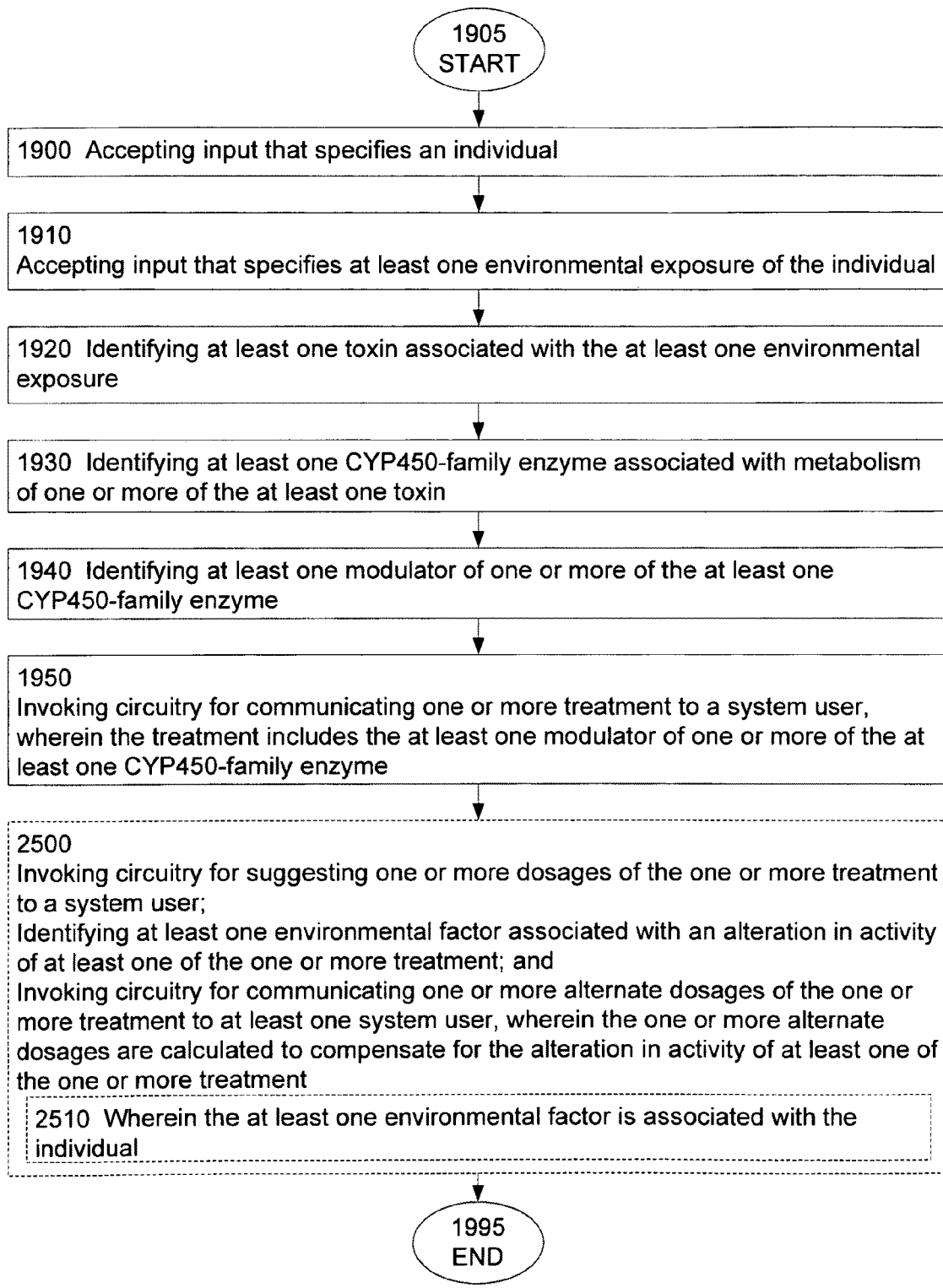
FIG. 25 is a flowchart illustrating aspects of a method such as the one depicted in FIG. 23.

FIG. 25 shows aspects of a method such as the one illustrated in FIG. 19. A method diagram may include block 2500, depicting: invoking circuitry for suggesting one or more dosages of the one or more treatment to a system user; identifying at least one environmental factor associated with an alteration in activity of at least one of the one or more treatment; and invoking circuitry for communicating one or more alternate dosages of the one or more treatment to at least one system user, wherein the one or more alternate dosages are calculated to compensate for the alteration in activity of at least one of the one or more treatment. Block 2500 may include block 2510, illustrating wherein the at least one environmental factor is associated with the individual.

Figure 26:
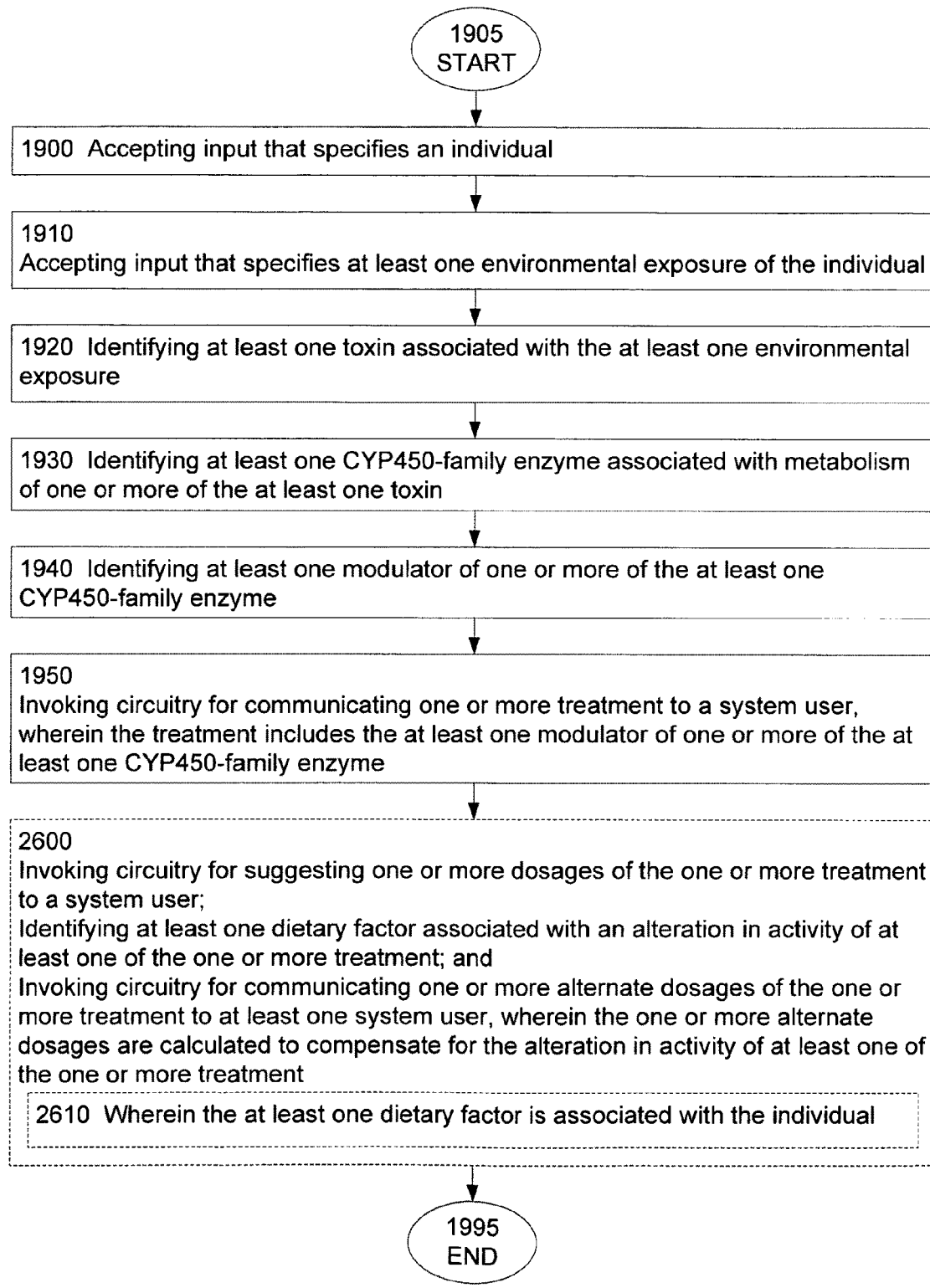
FIG. 26 is a flowchart depicting aspects of a method such as the one shown in FIG. 23.

FIG. 26 illustrates aspects of a method such as the one depicted in FIG. 19. A method diagram may include block 2600, showing: invoking circuitry for suggesting one or more dosages of the one or more treatment to a system user; identifying at least one dietary factor associated with an alteration in activity of at least one of the one or more treatment; and invoking circuitry for communicating one or more alternate dosages of the one or more treatment to at least one system user, wherein the one or more alternate dosages are calculated to compensate for the alteration in activity of at least one of the one or more treatment. Block 2600 may include block 2610, depicting wherein the at least one dietary factor is associated with the individual.

Figure 27:
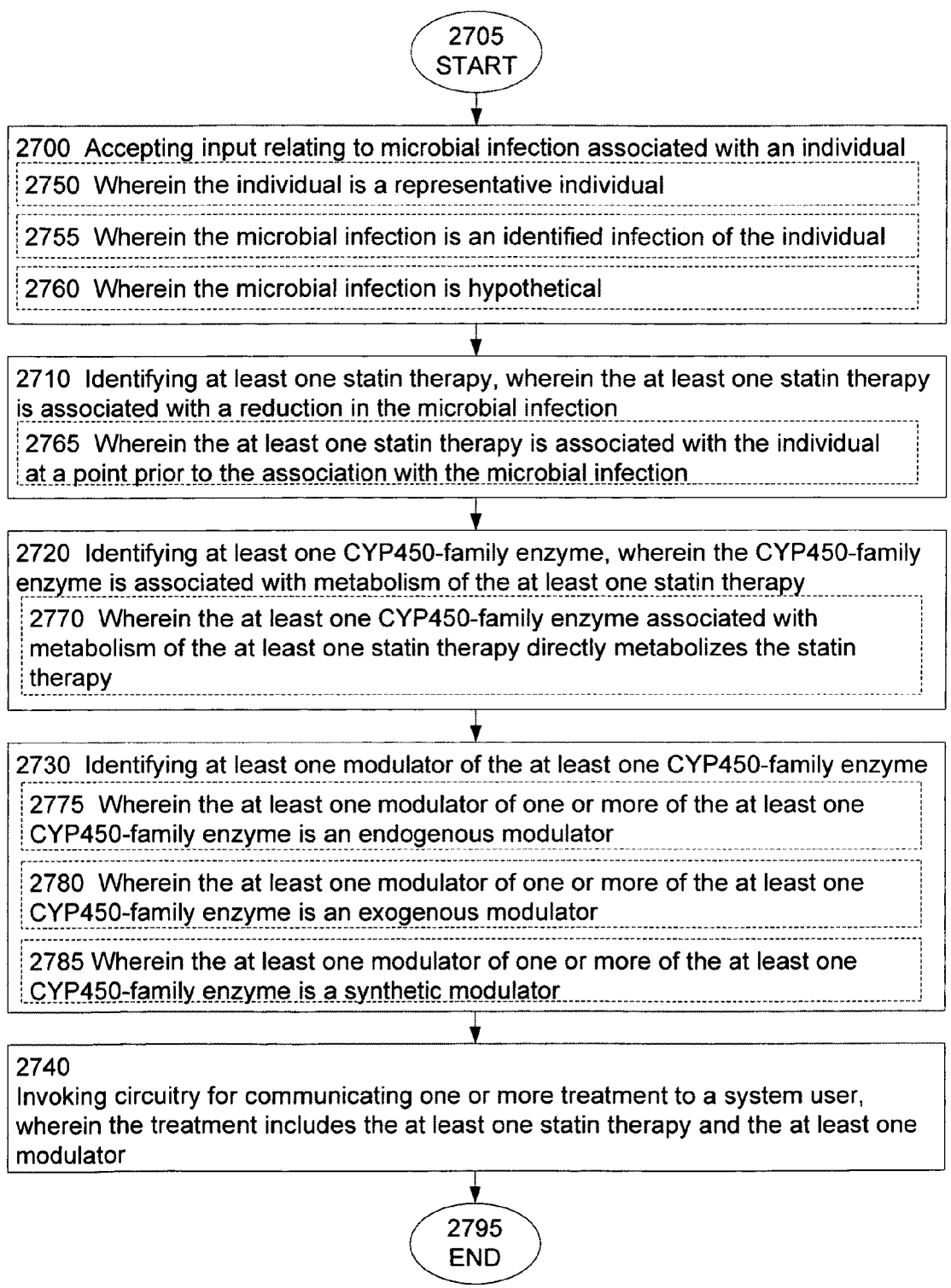
FIG. 27 is a flowchart illustrating aspects of a method.

FIG. 27 illustrates aspects of a method. The start of the method is depicted as block 2705. Block 2700 shows accepting input relating to microbial infection associated with an individual. Block 2700 may include one or more of blocks 2750, 2755 and 2760. Block 2750 depicts wherein the individual is a representative individual. Block 2755 shows wherein the microbial infection is an identified infection of the individual. Block 2760 illustrates wherein the microbial infection is hypothetical. Block 2710 shows identifying at least one statin therapy, wherein the at least one statin therapy is associated with a reduction in the microbial infection. Block 2710 may include block 2765, illustrating wherein the at least one statin therapy is associated with the individual at a point prior to the association with the microbial infection. Block 2720 depicts identifying at least one CYP450-family enzyme, wherein the CYP450-family enzyme is associated with metabolism of the at least one statin therapy. Block 2720 may include block 2770, showing wherein the at least one CYP450-family enzyme associated with metabolism of the at least one statin therapy directly metabolizes the statin therapy. Block 2730 shows identifying at least one modulator of the at least one CYP450-family enzyme. Block 2730 may include at least one of blocks 2775, 2780 and 2785. Block 2775 shows wherein the at least one modulator of one or more of the at least one CYP450-family enzyme is an endogenous modulator. Block 2780 shows wherein the at least one modulator of one or more of the at least one CYP450-family enzyme is an exogenous modulator. Block 2785 shows wherein the at least one modulator of one or more of the at least one CYP450-family enzyme is a synthetic modulator. Block 2740 depicts invoking circuitry for communicating one or more treatment to a system user, wherein the treatment includes the at least one statin therapy and the at least one modulator. Block 2795 depicts the end of the method.

Figure 28:
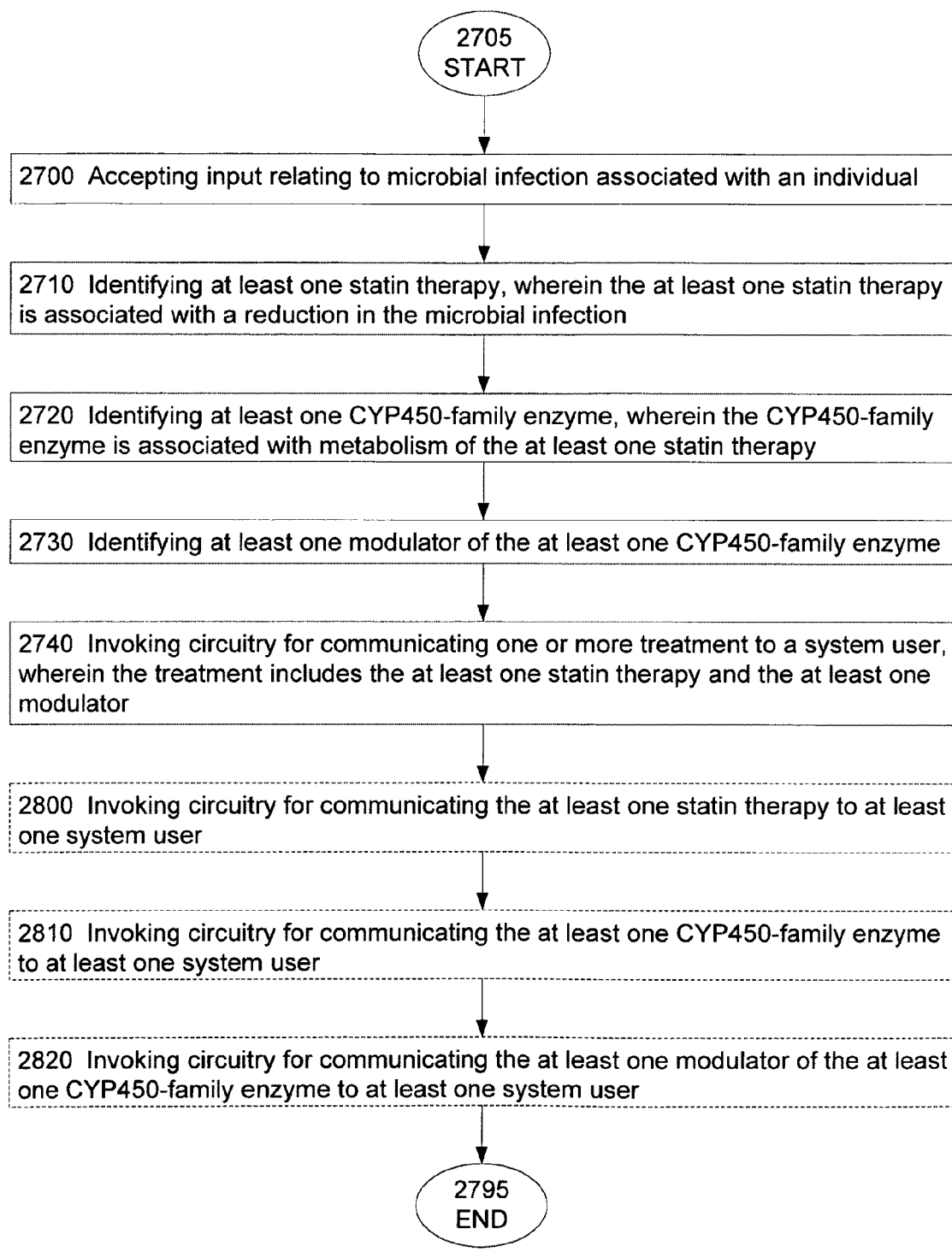
FIG. 28 is a flowchart showing aspects of a method such as the one depicted in FIG. 27.

FIG. 28 shows aspects of a method such as depicted in FIG. 27. A method diagram may include block 2800, depicting invoking circuitry for communicating the at least one statin therapy to at least one system user. A method diagram may include block 2810, showing invoking circuitry for communicating the at least one CYP450-family enzyme to at least one system user. A method diagram may include block 2820, showing invoking circuitry for communicating the at least one modulator of the at least one CYP450-family enzyme to at least one system user.

Figure 29:
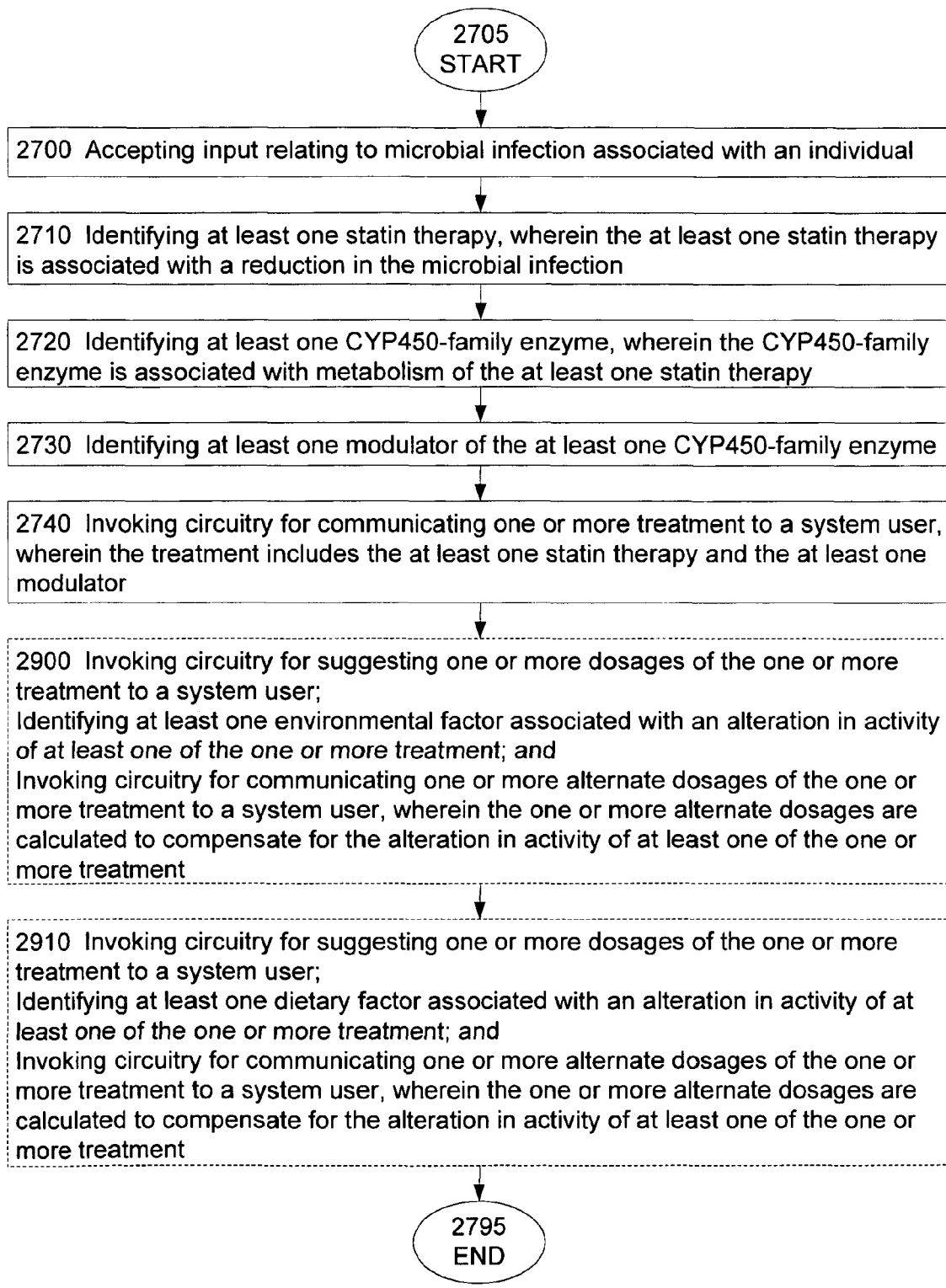
FIG. 29 is a flowchart depicting aspects of a method such as the one illustrated in FIG. 27.

FIG. 29 illustrates aspects of a method such as shown in FIG. 27. A method diagram may include block 2900, showing: invoking circuitry for suggesting one or more dosages of the one or more treatment to a system user; identifying at least one environmental factor associated with an alteration in activity of at least one of the one or more treatment; and invoking circuitry for communicating one or more alternate dosages of the one or more treatment to a system user, wherein the one or more alternate dosages are calculated to compensate for the alteration in activity of at least one of the one or more treatment. A method diagram may include block 2910, illustrating: invoking circuitry for suggesting one or more dosages of the one or more treatment to a system user; identifying at least one dietary factor associated with an alteration in activity of at least one of the one or more treatment; and invoking circuitry for communicating one or more alternate dosages of the one or more treatment to a system user, wherein the one or more alternate dosages are calculated to compensate for the alteration in activity of at least one of the one or more treatment.

Figure 30:
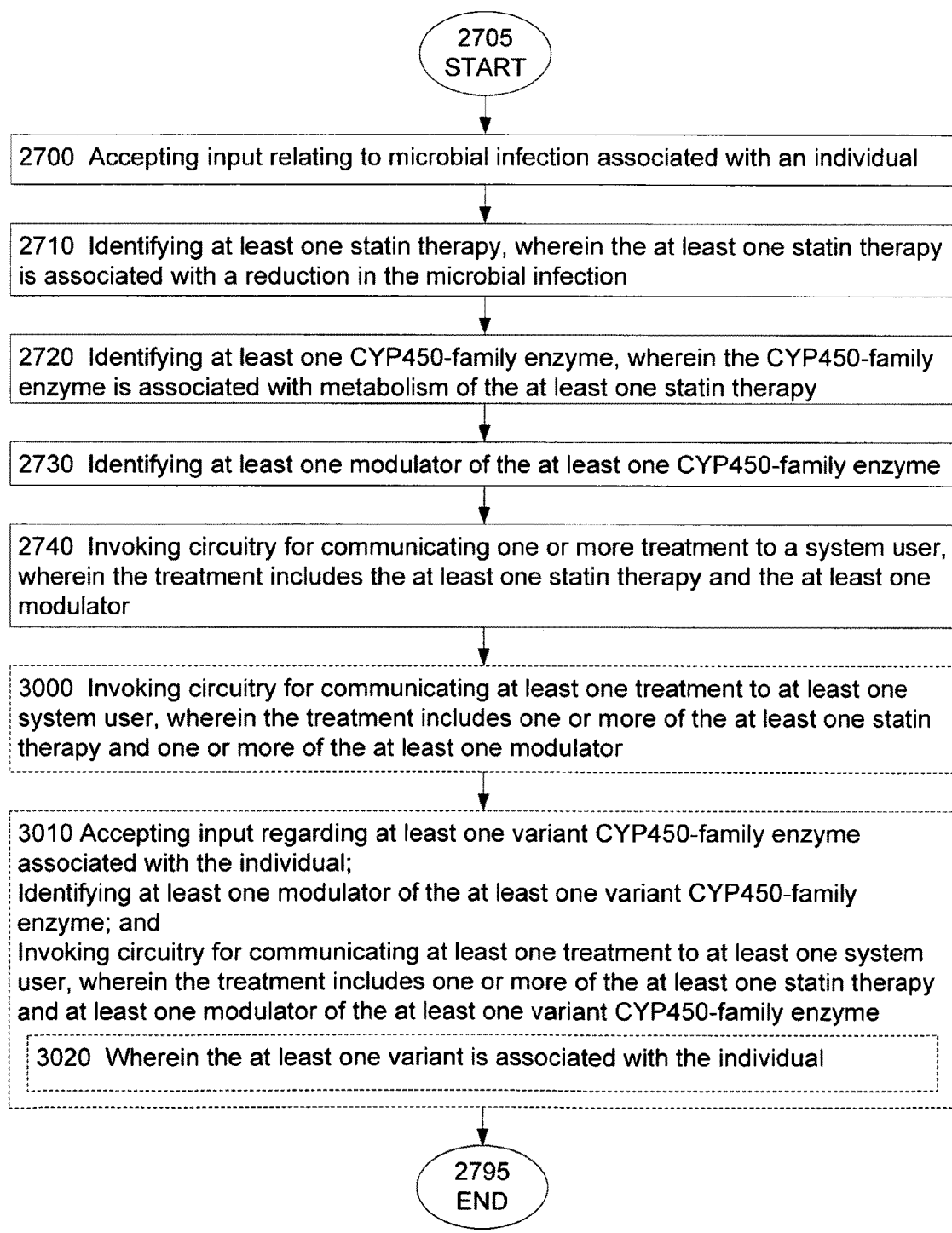
FIG. 30 is a flowchart showing aspects of a method such as the one depicted in FIG. 27.

FIG. 30 shows aspects of a method such as illustrated in FIG. 27. A method diagram may include block 3000, showing invoking circuitry for communicating at least one treatment to at least one system user, wherein the treatment includes one or more of the at least one statin therapy and one or more of the at least one modulator. A method diagram may include block 3010, depicting: accepting input regarding at least one variant CYP450-family enzyme associated with the individual; identifying at least one modulator of the at least one variant CYP450-family enzyme; and invoking circuitry for communicating at least one treatment to at least one system user, wherein the treatment includes one or more of the at least one statin therapy and at least one modulator of the at least one variant CYP450-family enzyme. Block 3010 may include block 3020, wherein the at least one variant is associated with the individual.

Figure 31:
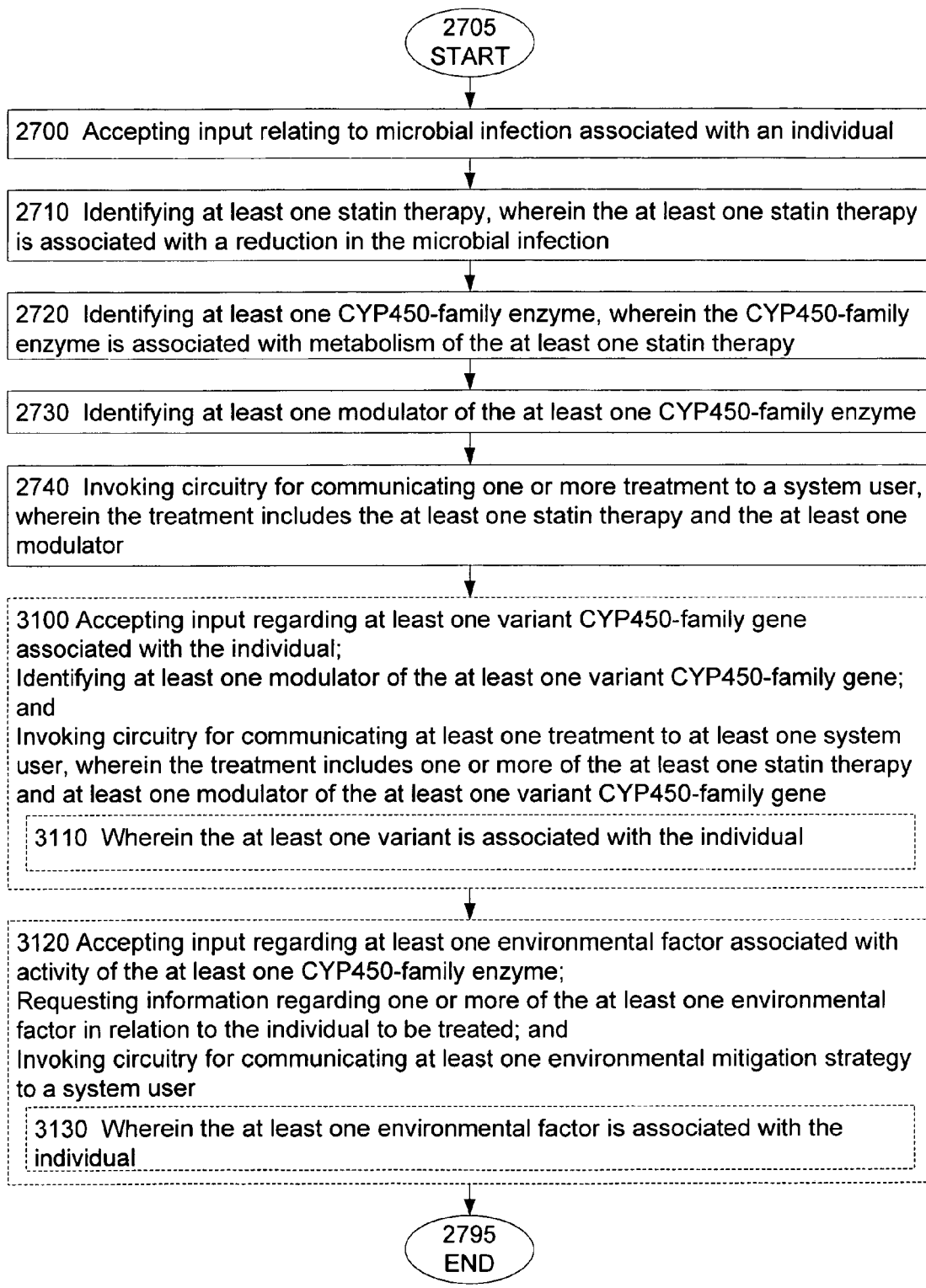
FIG. 31 is a flowchart depicting aspects of a method such as the one illustrated in FIG. 27.

FIG. 31 shows aspects of a method such as depicted in FIG. 27. A method diagram may include block 3100, showing: accepting input regarding at least one variant CYP450-family gene associated with the individual; identifying at least one modulator of the at least one variant CYP450-family gene; and invoking circuitry for communicating at least one treatment to at least one system user, wherein the treatment includes one or more of the at least one statin therapy and at least one modulator of the at least one variant CYP450-family gene. Block 3100 may include block 3110, illustrating wherein the at least one variant is associated with the individual. A method diagram may include block 3120, showing: accepting input regarding at least one environmental factor associated with activity of the at least one CYP450-family enzyme; requesting information regarding one or more of the at least one environmental factor in relation to the individual to be treated; and invoking circuitry for communicating at least one environmental mitigation strategy to a system user. Block 3120 may include block 3130, showing wherein the at least one environmental factor is associated with the individual.

Figure 32:
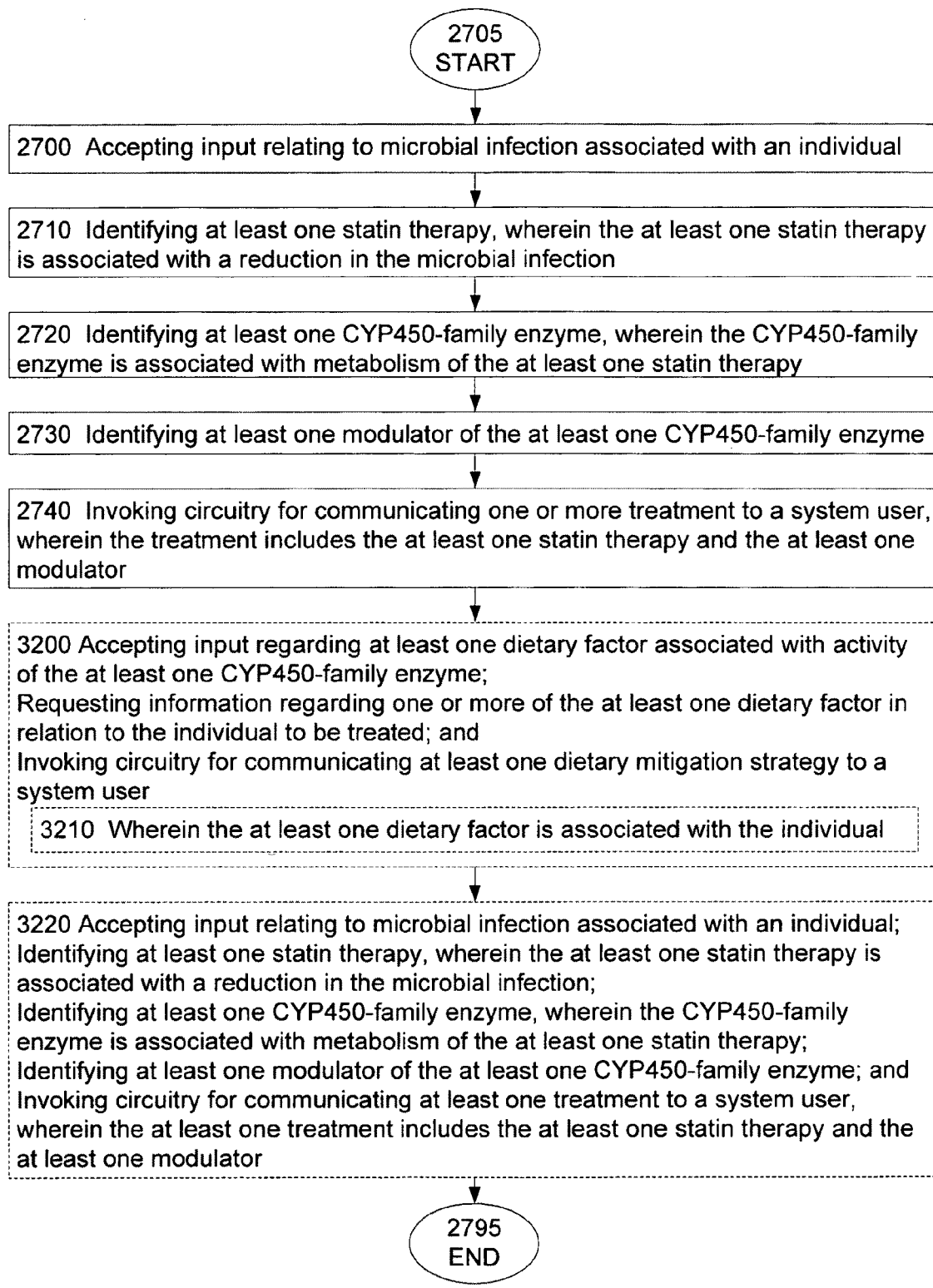
FIG. 32 is a flowchart showing aspects of a method such as the one depicted in FIG. 27.

FIG. 32 illustrates aspects of a method such as diagrammed in FIG. 27. A method diagram may include block 3200, showing: accepting input regarding at least one dietary factor associated with activity of the at least one CYP450-family enzyme; requesting information regarding one or more of the at least one dietary factor in relation to the individual to be treated; and invoking circuitry for communicating at least one dietary mitigation strategy to a system user. Block 3200 may include block 3210, showing wherein the at least one dietary factor is associated with the individual. A method diagram may include block 3220, illustrating: accepting input relating to microbial infection associated with an individual; identifying at least one statin therapy, wherein the at least one statin therapy is associated with a reduction in the microbial infection; identifying at least one CYP450-family enzyme, wherein the CYP450-family enzyme is associated with metabolism of the at least one statin therapy; identifying at least one modulator of the at least one CYP450-family enzyme; and invoking circuitry for communicating at least one treatment to a system user, wherein the at least one treatment includes the at least one statin therapy and the at least one modulator.

Although system user 10 is shown/described herein as a single illustrated figure, those skilled in the art will appreciate that system user 10 may be representative of a human user, a robotic user (e.g., computational entity), and/or substantially any combination thereof (e.g., a user may be assisted by one or more robotic agents) unless context dictates otherwise. Those skilled in the art will appreciate that, in general, the same may be said of "sender" and/or other entity-oriented terms as such terms are used herein unless context dictates otherwise.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures. Electronic circuitry, for example, may have one or more paths of electrical current constructed and arranged to implement various functions as described herein. In some implementations, one or more media may be configured to bear a device-detectable implementation when such media hold or transmit device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, C++ or other code sequences can be compiled or implemented in high-level descriptor languages (e.g., a logic-synthesizable language, a hardware description language, a hardware design simulation, and/or other such similar mode(s) of expression). For example, some or all of the logical expression may be manifested as a Verilog-type hardware description or other circuitry model before physical implementation in hardware. Those skilled in the art will recognize how to obtain, configure, and optimize suitable transmission or computational elements, material supplies, actuators, or other structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, the various aspects described herein which can be implemented, individually and/or collectively, by a wide range of hardware, software, firmware, and/or any combination thereof can be viewed as being composed of various types of "circuitry." Consequently, as used herein "circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). As used herein, "circuitry" includes, but is not limited to, optical, chemical, biological-based, or wireless circuitry. As used herein "circuitry" includes, but is not limited to, solid-state or integrated circuitry. As used herein, "circuitry" includes, but is not limited to, analog, digital, or mixed-signal circuitry. Those having skill in the art will recognize that the subject matter described herein may be implemented in an analog or digital fashion or some combination thereof.

At least a portion of the devices and/or processes described herein can be integrated into an image processing system. Those having skill in the art will recognize that a typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system may be implemented utilizing suitable commercially available components, such as those typically found in digital still systems and/or digital motion systems.

At least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

It is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory). Further, implementation of at least part of a system for performing a method in one territory does not preclude use of the system in another territory. A sale of a system or method may likewise occur in a territory even if components of the system or method are located and/or used outside the territory.

Aspects of the systems and methods described herein may be illustrated by the following non-limiting examples.

EXAMPLES

Example 1

Methods and systems such as those described herein including a drug therapy that includes a statin therapy, for example for use in the treatment of bacterial infections, may be of aid to healthcare providers. For example, methods and systems may access information from clinical studies that show a significant reduction in overall mortality for patients with bacteremia who are treated with statins (6% versus 28%, P=0.002; Liappis et al, The effect of statins on mortality in patients with bacteremia, Clin. Inf. Dis. 33, 1352-1357 (2001), which is herein incorporated by reference). Methods and systems may access information regarding metabolism of statins by CYP450-family enzymes, including the identity of major CYP450-family enzymes (e.g. CYP3A4, CYP2C9 and CYP2C8) responsible for statin metabolism, and the identities of modulators (inhibitors or inducers) of the relevant CYP450-family enzymes including endogenous, exogenous and synthetic compounds (e.g. steroid hormones, xenobiotics and pharmaceuticals respectively; see Beaird, HMG-CoA Reductase Inhibitors: Assessing Differences in Drug Interactions and Safety Profiles, J. Am. Pharm. Assoc. 40, 637-644 (2000) which is incorporated by reference herein). Methods and systems may access information regarding the relative amount of specific CYP450-family enzyme activity (e.g. CYP3A4 enzyme activity) that can vary considerably between individuals due to genetic differences (variant genes) and environmental factors (Omari et al, Pharmacogenetics of the cytochrome P450 enzyme system: review of current knowledge and clinical significance, J. Pharm. Pract. vol. 20, pp. 206-214).

The methods and systems described herein may aid health caregivers to prescribe treatments and give advice to patients with existing infections or to patients at risk of infection. Moreover, methods and systems with access to information generated in clinical studies may identify groups of patients or groups of individuals who are at risk for bacterial infection and candidates for antibacterial treatments as well as communicate relevant treatments. Exemplary groups include: organ or cell transplant patients; patients with chronic kidney disease (see: Gupta et al, Statin use and hospitalization for sepsis in patients with chromic kidney disease, J. Amer. Med. Assoc. vol. 297, pp. 1455-1464 (2007) which is incorporated by reference herein); hospital patients (e.g. nosocomial infections; Liappis et al, Ibid.); patients in intensive care facilities; immunocompromised individuals; athletes with chronic or frequent wounds (e.g. football players, wrestlers); soldiers; individuals in institutions (e.g. nursing homes, assisted living facilities, schools for the handicapped); and other individuals in situations with a high risk of bacterial infection.

Methods and systems may access information regarding CYP3A4 substrates, for example, atorvastatin, cerivastatin, lovastatin and simvastatin, and accept input regarding an individual's CYP3A4 genotype (e.g. heterozygosity for CYP3A4 variants). Furthermore methods and systems may identify exogenous modulators (e.g. erythromycin, ketoconazole, rifampin) that inhibit or induce CYP3A4 metabolic activity to communicate the suggestion, for example, to coadminister erythromycin with atorvastatin, which may increase the AUC and Cmax for atorvastatin (Beaird, Ibid.). Methods and systems such as those described herein may also recommend dosages of erythromycin and atorvastatin based on information regarding statin toxicities and predicted changes in pharmacokinetic parameters (e.g. AUC and Cmax) of atorvastatin when coadministered with erythromycin (Beaird, Ibid.). For example, large changes (about threefold increases) in the AUC and half-life of atorvastatin have been observed when itraconazole is coadministered. Methods and systems such as those described herein may therefore communicate treatments that do not include both atorvastatin and itraconazole, or which do so with dosages that take into account the predicted activity of both drugs.

Methods and systems may also identify dietary factors associated with alteration in activity of one or more treatment. For example, grapefruit juice modulates (inhibits) CYP3A4 activity and increases AUC and half-life for atorvastatin (Beaird, Ibid.). For a patient with an existing bacterial infection or at risk for bacterial infection (e.g. intensive care patients, renal transplant patients) the methods and systems described herein may communicate treatments and alternate dosages to aid health care providers to prescribe statins and CYP450-family enzyme modulators and to advise patients regarding dietary intakes. Data derived from, for example, in vitro studies (Omari, Ibid.), preclinical studies, and clinical studies (Beaird, Ibid.) may provide a knowledge base for the methods and systems described herein.

Example 2

Several environmental toxins (e.g. aflatoxin $B_1$, ethyl carbamate) are putative carcinogens that have been predicted to undergo activation mediated by CYP450-family enzymes prior to forming DNA and protein adducts that ultimately lead to carcinogenesis. Methods and systems such as those described herein may access information regarding the CYP450-family enzymes (e.g. CYP3A4, CYP2E1, CYP1A2) primarily responsible for the activation of individual environmental toxins (see, for example, Guengerich et al, Cytochrome P450 and chemical toxicology, Chem. Res. Toxicol. vol. 21, pp. 70-83 (2008), which is incorporated by reference herein). Methods and systems such as those described herein may identify CYP450-family enzymes important for activation of environmental toxins and may identify modulators of the CYP450-family enzymes. Methods and systems may communicate treatments with a goal of preventing or minimizing toxin activation. Methods and systems may accept input regarding an individual's CYP450-family genotype, allowing personalized prescription of CYP450-family enzyme modulators and modulator dosages to address variant CYP450-family enzyme alleles and different CYP450-family enzyme phenotypes, such as poor metabolizer or ultrarapid metabolizer. Methods and systems such as those described herein may be useful to aid in prescribing treatments and giving advice to reduce or prevent toxin activation.

Aflatoxin $B_1$ is a mycotoxin produced by *Aspergillus* fungi, and human exposure is most often via foodstuffs such as nuts, cereals and spices. Chronic aflatoxin $B_1$ exposure is associated with a high risk of developing hepatocellular carcinoma, and carcinogenesis is likely promoted by the activation of aflatoxin $B_1$ to an epoxide derivative as a result of CYP3A4 enzymatic activity (Guengerich et al, Ibid.). Methods and systems such as those described herein may incorporate information regarding CYP3A4 substrate specificities and CYP3A4 modulators, such as itraconazole, erythromycin, and ritonavir, and may communicate treatments designed to reduce CYP3A4 metabolic activity and to reduce or prevent activation of aflatoxin $B_1$. Methods and systems may incorporate information resulting from clinical studies. For example, itraconazole given orally (200 mg/day) for 4 consecutive days reduces CYP3A metabolic activity and increases the Cmax and AUC of CYP3A substrates (e.g. simvastatin) by ten-fold (Neuvonen et al, Simvastatin but not pravastatin is very susceptible to interaction with the CYP3A4 inhibitor itraconazole, Clin. Pharmacol. Ther. vol. 63, pp. 332-341 (1998) which is incorporated by reference herein). Methods and systems may accept input with information regarding a CYP3A4 genotype for an individual and may identify one or more modulators of CYP3A4 relative to that genotype. For example, CYP3A4*1B is a variant associated with increased levels of CYP3A4 expression (Omari et al, Ibid.) that requires increased dosages of a modulator (e.g. Itraconazole) to reduce or prevent CYP3A4 enzymatic activity and aflatoxin $B_1$ activation (Omari et al, Ibid.).

Example 3

CYP450-family enzymes are relevant for environmental and occupational medicine due to their substrate spectrum, which includes a number of industrial chemicals such as alkanes, alkenes, aromatic and halogenated hydrocarbons. Methods and systems described herein may be useful to aid healthcare workers (such as doctors, nurses, paramedics) to prescribe treatments and give advice to individuals previously exposed to environmental toxins or at risk of exposure. Methods and systems such as those described herein may access information regarding: CYP450-family enzyme substrate specificity, CYP450-family enzyme metabolites, CYP450-family enzyme modulators, polymorphic CYP450-family genes, CYP450-family enzyme genotypes, and CYP450-family enzyme phenotypes. Methods and systems such as those described herein may communicate treatments and advice for individuals based on processes and information regarding one or more specific environmental toxicants, major CYP450-family enzyme(s) associated with the metabolism, the identity and bioactivity of metabolites derived from a toxicant, and the identity of modulators of a CYP450-family enzyme. An individual's CYP450-family enzyme, CYP450-family enzyme variants, CYP450-family gene and CYP450-family gene variants may be considered by the systems and methods.

For example, a computerized system may be useful to aid a physician in treating an individual exposed to an industrial solvent such as carbon tetrachloride. Carbon tetrachloride (CCL4) is metabolized primarily by CYP2E1, which converts CCL4 to a highly reactive trichloromethyl radical that induces lipid peroxidation, damages cellular membranes and ultimately causes hepatocellular toxicity. CCL4 cellular toxicity is proportional to CYP2E1 enzyme activity; cell lines overexpressing CYP2E1 are killed by reduced concentrations of CCL4 relative to parental cell lines with low expression of CYP2E1 (see Takahashi et al, Increase cytotoxicity of carbon tetrachloride in a human hepatoma cell line overexpressing Cytochrome P450 2E1, J. Int. Med. Res. vol. 30, pp. 400-405 (2002), which is herein incorporated by reference). Individual variation in CYP2E1 activity (which may be measured in vivo with a model substrate, chlorzoxazone) is associated with susceptibility to toxicity of environmental toxicants such as CCL4. Moreover, polymorphisms and variants in CYP2E1 genes have been associated with increased or reduced enzymatic activity (Omari et al, Ibid.) Following known or suspected exposure to CCL4, methods and system such as those described herein may be used to identify CYP2E1 variants, to identify modulators of CYP2E1 that inhibit CYP2E1 enzymatic activity, and to communicate treatments that may prevent or reduce the production of reactive metabolites, (e.g. trichloromethyl radicals) and thereby prevent or reduce hepatocellular toxicity. Methods and systems such as those described herein may identify modulators such as CYP2E1 inhibitors (e.g. 4-methyl pyrazole, diallyl sulfide, phenylethylisothiocyanate) which inhibit CYP2E1 enzymatic activity and reduce the toxicity of CCL4 (Cederbaum et al, CYP2E1-Biochemical and toxicological aspects and role in alcohol-induced liver injury, Mount Sinai J. of Med. 73, 657-672 (2006) which is incorporated by reference herein). Methods and systems may also associate CYP2E1 polymorphisms and variants with individuals, including representative individuals, in relation to their prevalence in various populations. For example, CYP2E1*1D is associated with greater inducibility and higher CYP1E activity, and has been found in 7% of Caucasians and 31% of African-Americans. CYP2E1*2 is associated with low activity (40% of CYP2E1) but has been found in only 2.5% of a Chinese population and not in other ethnic groups. Another variant, CYP2E1*5 has been found in 27% of Asian populations and associated with increased CYP2E1 expression (Omari et al, Ibid.). Methods and systems such as those described herein may incorporate databases and updated information regarding CYP2E1 genotypes and corresponding phenotypes. Methods and systems may access genotype data obtained from individuals as well as phenotype data obtained with model substrates and in vitro studies. Methods and systems may aid healthcare workers by integrating information on an environmental toxicant and an individual's CYP2E1 genotype and phenotype with comprehensive knowledge of CYP2E1 substrates, modulators, genes, variants and phenotypes. The system can communicate preferred treatments and advise individuals who are at risk, or susceptible to toxicity from specific toxicants.

Example 4

Methods and systems such as those described herein may be useful to aid in prescription of drugs and giving advice to patients based in part on the information that the CYP450-family enzyme CYP2E1 is an important enzyme for liver toxicity, and that modulation of CYP2E1 activity can reduce liver toxicity (see Cederbaum, CYP2E1-Biochemical and toxicological aspects and role in alcohol-induced liver injury, Mount Sinai Journal of Medicine, 73(4) 657-672, 2006, which is herein incorporated by reference). Methods and systems may incorporate information regarding many substrates that CYP2E1 metabolizes and activates, including ethanol, acetaminophen, carbon tetrachloride and N-nitrosodimethylamine. In some situations, the metabolism of substrates by CYP2E1 may yield more toxic products than the substrate itself. Methods and systems may identify modulators of CYP2E1 activity for example, ethanol (an inducer) and other modulators (e.g. isoniazid, phenobarbital and rifampin). Methods and systems may also incorporate information regarding chronic alcohol consumption, which increases the risk of acetaminophen toxicity as alcohol-induced CYP2E1 activity increases risk for the production of toxic metabolites derived from acetaminophen. Methods and systems may incorporate data from methods and assays measuring the relative level of CYP2E1 activity in human hepatocytes using a CYP2E1-specific substrate, chlorzoxazone, as described (e.g. Madan et al., Effects of protypical microsomal enzyme inducers on Cytochrome P450 expression in cultured human hepatocytes, DMD 31: 21-31, 2003; incorporated by reference herein). For example, human liver microsomes stored frozen at −80° C. with 0.25 M sucrose may be assayed for protein content with a BCA Protein Assay Kit (Pierce Chem. Co., Rockford, Ill.; the manual for which is hereby incorporated by reference). Fifty microgram aliquots of human liver microsome protein may be assayed in a total volume of 1 ml at 37° C. and chlorzoxazone-6 hydroxalase activity may be measured with 15, 30 and 120 micromolar chlorzoxazone (e.g. Robertson et al, In Vitro inhibition and induction of human hepatic Cytochrome P450 enzymes by modafinil, DMD 28: 664-671, 2000; incorporated by reference herein). Alternatively, methods and systems may incorporate information resulting from assays of the level of CYP2E1 activity in individuals determined by orally administering 500 mg of chlorzoxazone and taking venous blood samples over a 10 hr period, followed by calculations of areas under the curve of plasma concentration versus time (AUC) of chlorzoxazone and 6-OHchlorzoxazone. The 6-OHchlorzoxazone/chlorzoxazone concentration ratio at t=2 hr is a simple and non-traumatic marker of CYP2E1 induction (Girre et al, Assessment of Cytochrome P4502E1 induction in alcoholic patients by chlorzoxazone pharmacokinetics, Biochem. Pharmacol. 47: 1503-08, 1994; incorporated by reference herein). Methods and systems may incorporate information regarding CYP2E1 enzymatic activity and identify modulators of CYP2E1 activity that for example, would inhibit CYP2E1 activity to avoid generation of toxic metabolites from acetaminophen or ethanol in patients with hepatic toxicity.

Methods and systems disclosed herein may associate substrates and modulators recognized by CYP2E1 based in part on data obtained from in vitro assays using human hepatocytes (Madan et al, Ibid.; Robertson et al, Ibid.; Kalra, Cytochrome P450 enzyme isoforms and their therapeutic implications: an update, Indian Journal of Medical Sciences, 61, 102-116 (2007), which are incorporated by reference herein.). For example, Table 1 lists some known substrates, inhibitors and inducers of CYP2E1. To avoid toxicity or to treat toxicity due to CYP2E1 metabolic activity, methods and systems may identify CYP2E1 substrates and modulators as well as communicating treatments to lower the level of toxic metabolites. For example, if an individual chronically consumes alcohol and also takes acetaminophen, then at least two substrates for CYP2E1 are present in that individual's body. In some situations, ethanol may be identified as a modulator as it may act to induce CYP2E1 activity. The methods and systems described herein can identify interaction of ethanol and acetaminophen and recommend a reduction in ethanol consumption and an alternative to acetaminophen to reduce substrate levels. Methods and systems may communicate treatment including modulation of CYP2E1 activity with a specific modulator that inhibits activity, for example, disulfram, as well as reduction of the CYP2E1 inducer, ethanol.

TABLE 1

Substrates and Modulators of CYP2E1*

| Substrate | Inhibitor | Inducer |
|---|---|---|
| Acetaminophen | Disulfuram | Ethanol |
| Chlorzoxazone | 4-Methylpyrazole | Isoniazid |
| Ethanol | Diethyldithiocarbamate | Phenobarbital |
| Enflurane | Diallylsulfide | Rifampin |
| Halothane | Phenethylisothiocyanate | Acetone |
| Isoflurane | | |
| N-Nitrosodimethylamine | | |
| Carbon tetrachloride | | |
| Tamoxifen | | |

*Data taken from: Kalra et al, Ibid.; Madan et al, Ibid.; Jaeschke et al, FORUM mechanisms of hepatotoxicity, Toxicological Sciences, 65, 166-176, (2001), which are incorporated by reference herein.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

The herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, the recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

The various aspects and embodiments disclosed herein are for purposes of illustration and are not intended to be limiting, with the true scope and spirit being indicated by the following claims.

What is claimed is:

1. A method comprising:
   accepting input that specifies an individual;
   accepting input that specifies at least one environmental exposure of the individual;
   identifying at least one toxin associated with the at least one environmental exposure;
   identifying at least one CYP450-family enzyme associated with metabolism of one or more of the at least one toxin;
   identifying at least one modulator of one or more of the at least one CYP450-family enzyme; and
   invoking circuitry for communicating one or more treatment to a system user, wherein the one or more treatment includes the at least one modulator of one or more of the at least one CYP450-family enzyme.

2. The method of claim 1, comprising:
   accepting input identifying at least one variant of the at least one CYP450-family enzyme;

identifying at least one modulator of the at least one variant; and invoking circuitry for communicating the one or more treatment to the at least one system user, wherein the one or more treatment includes one or more of the at least one modulator of the at least one variant.

3. The method of claim 1, comprising:

accepting input identifying at least one variant of at least one CYP450-family gene;

identifying at least one modulator of the at least one variant CYP450-family gene; and invoking circuitry for communicating the one or more treatment to the at least one system user, wherein the one or more treatment includes one or more of the at least one modulator of the at least one variant CYP450-family gene.

4. The method of claim 1, comprising:

identifying at least one additional CYP450-family enzyme associated with metabolism of one or more of the at least one toxin;

identifying at least one modulator of one or more of the at least one additional CYP450-family enzyme; and invoking circuitry for communicating the one or more treatment for the individual to the at least one system user, wherein the one or more treatment includes both the at least one modulator of one or more of the at least one CYP450-family enzyme and the at least one modulator of one or more of the at least one additional CYP450-family enzyme.

5. The method of claim 1, comprising:

identifying at least one additional CYP450-family enzyme associated with metabolism of one or more of the at least one toxin;

accepting input regarding at least one variant of the at least one additional CYP450-family enzyme associated with the individual;

identifying at least one modulator of one or more of the at least one variant of the at least one additional CYP450-family enzyme; and invoking circuitry for suggesting the one or more treatment to the at least one system user, wherein the one or more treatment includes both the at least one modulator of one or more of the at least one CYP450-family enzyme and the at least one modulator of one or more of the at least one variant of the at least one additional CYP450-family enzyme.

6. The method of claim 1, comprising:

invoking circuitry for suggesting one or more dosages of the one or more treatment to the system user;

identifying at least one environmental factor associated with an alteration in activity of at least one of the one or more treatment; and invoking circuitry for communicating one or more alternate dosages of the one or more treatment to the at least one system user, wherein the one or more alternate dosages are calculated to compensate for the alteration in activity of at least one of the one or more treatment.

7. The method of claim 6, wherein the at least one environmental factor is associated with the individual.

8. The method of claim 1, comprising:

invoking circuitry for suggesting one or more dosages of the one or more treatment to the system user;

identifying at least one dietary factor associated with an alteration in activity of at least one of the one or more treatment; and invoking circuitry for communicating one or more alternate dosages of the one or more treatment to the at least one system user, wherein the one or more alternate dosages are calculated to compensate for the alteration in activity of at least one of the one or more treatment.

9. The method of claim 8, wherein the at least one dietary factor is associated with the individual.

10. The method of claim 1, comprising:

associating at least one anatomic location with predicted activity of the at least one CYP450-family enzyme;

associating the at least one anatomic location with one or more of the at least one modulator of one or more of the at least one CYP450-family enzyme; and invoking circuitry for communicating the one or more treatment to the system user, wherein the one or more treatment includes the at least one modulator of one or more of the at least one CYP450-family enzyme associated with the at least one anatomic location.

11. A system comprising:

circuitry for accepting input that specifies an individual;

circuitry for accepting input that specifies at least one environmental exposure of the individual;

circuitry for identifying at least one toxin associated with the at least one environmental exposure;

circuitry for identifying at least one CYP450-family enzyme associated with metabolism of one or more of the at least one toxin;

circuitry for identifying at least one modulator of one or more of the at least one CYP450-family enzyme; and circuitry for communicating one or more treatment to a system user, wherein the one or more treatment includes the at least one modulator of one or more of the at least one CYP450-family enzyme.

12. The system of claim 11, comprising:

circuitry for accepting input identifying at least one variant of the at least one CYP450-family enzyme;

circuitry for identifying at least one modulator of the at least one variant; and circuitry for communicating the one or more treatment to the at least one system user, wherein the one or more treatment includes one or more of the at least one modulator of the at least one variant.

13. The system of claim 11, comprising:

circuitry for accepting input identifying at least one variant of at least one CYP450-family gene;

circuitry for identifying at least one modulator of the at least one variant of the at least one CYP450-family gene; and circuitry for communicating the one or more treatment to the at least one system user, wherein the one or more treatment includes one or more of the at least one modulator of the at least one variant.

14. The system of claim 11, comprising:

circuitry for identifying at least one additional CYP450-family enzyme associated with metabolism of one or more of the at least one toxin;

circuitry for identifying at least one modulator of one or more of the at least one additional CYP450-family enzyme; and circuitry for communicating the one or more treatment for the individual to the at least one system user, wherein the one or more treatment includes both the at least one modulator of the at least one CYP450-family enzyme and the at least one modulator of the at least one additional CYP450-family enzyme.

15. The system of claim 11, comprising:

circuitry for identifying at least one additional CYP450-family enzyme associated with metabolism of one or more of the at least one toxin;

circuitry for accepting input regarding at least one variant of the at least one additional CYP450-family enzyme associated with the individual;
circuitry for identifying at least one modulator of one or more of the at least one variant of the at least one additional CYP450-family enzyme; and
circuitry for suggesting the one or more treatment to the at least one system user, wherein the one or more treatment includes both the at least one modulator of the at least one CYP450-family enzyme and the at least one modulator of the at least one variant of the at least one additional CYP450-family enzyme.

16. The system of claim 11, comprising:
circuitry for suggesting one or more dosages of the one or more treatment to the system user;
circuitry for identifying at least one environmental factor associated with an alteration in activity of at least one of the one or more treatment; and
circuitry for communicating one or more alternate dosages of the one or more treatment to the at least one system user, wherein the one or more alternate dosages are calculated to compensate for the alteration in activity of at least one of the one or more treatment.

17. The system of claim 16, wherein the at least one environmental factor is associated with the individual.

18. The system of claim 11, comprising:
circuitry for suggesting one or more dosages of the one or more treatment to the system user;
circuitry for identifying at least one dietary factor associated with an alteration in activity of at least one of the one or more treatment; and
circuitry for communicating one or more alternate dosages of the one or more treatment to the at least one system user, wherein the one or more alternate dosages are calculated to compensate for the alteration in activity of at least one of the one or more treatment.

19. The system of claim 18, wherein the at least one dietary factor is associated with the individual.

20. The system of claim 11, comprising:
circuitry for associating at least one anatomic location with predicted activity of the at least one CYP450-family enzyme;
circuitry for associating the at least one anatomic location with one or more of the at least one modulator; and
circuitry for communicating the one or more treatment to the system user, wherein the one or more treatment includes the at least one modulator of one or more of the at least one CYP450-family enzyme associated with the at least one anatomic location.

21. A method, comprising:
accepting input relating to microbial infection associated with an individual;
identifying at least one statin therapy, wherein the at least one statin therapy is associated with a reduction in the microbial infection;
identifying at least one CYP450-family enzyme, wherein the at least one CYP450-family enzyme is associated with metabolism of the at least one statin therapy;
identifying at least one modulator of the at least one CYP450-family enzyme; and
invoking circuitry for communicating at least one treatment to a system user, wherein the at least one treatment includes the at least one statin therapy and the at least one modulator.

22. The method of claim 21, comprising:
invoking circuitry for suggesting one or more dosages of the at least one treatment to the system user;
identifying at least one environmental factor associated with an alteration in activity of the at least one treatment; and
invoking circuitry for communicating one or more alternate dosages of the at least one treatment to the system user, wherein the one or more alternate dosages are calculated to compensate for the alteration in activity of the at least one treatment.

23. The method of claim 21, comprising:
invoking circuitry for suggesting one or more dosages of the at least one treatment to the system user;
identifying at least one dietary factor associated with an alteration in activity of the at least one treatment; and
invoking circuitry for communicating one or more alternate dosages of the at least one treatment to the system user, wherein the one or more alternate dosages are calculated to compensate for the alteration in activity of the at least one treatment.

24. The method of claim 21, comprising:
accepting input regarding at least one variant of the at least one CYP450-family enzyme associated with the individual;
identifying at least one modulator of the at least one variant of the at least one CYP450-family enzyme; and
invoking circuitry for communicating the at least one treatment to the system user, wherein the at least one treatment includes one or more of the at least one statin therapy and the at least one modulator of the at least one variant of the at least one CYP450-family enzyme.

25. The method of claim 21, comprising:
accepting input regarding at least one variant of the at least one CYP450-family gene associated with the individual;
identifying at least one modulator of the at least one variant of the at least one CYP450-family gene; and
invoking circuitry for communicating the at least one treatment to the system user, wherein the at least one treatment includes one or more of the at least one statin therapy and the at least one modulator of the at least one variant of the at least one CYP450-family gene.

26. The method of claim 21, comprising:
identifying at least one environmental factor associated with activity of the at least one CYP450-family enzyme;
requesting information regarding one or more of the at least one environmental factor in relation to the individual to be treated; and
invoking circuitry for communicating at least one environmental mitigation strategy to the system user.

27. The method of claim 25, wherein the at least one environmental factor is associated with the individual.

28. The method of claim 21, comprising:
identifying at least one dietary factor associated with activity of the at least one CYP450-family enzyme;
requesting information regarding one or more of the at least one dietary factor in relation to the individual to be treated; and
invoking circuitry for communicating at least one dietary mitigation strategy to the system user.

29. The method of claim 28, wherein the at least one dietary factor is associated with the individual.

30. The method of claim 21, comprising:
associating at least one anatomic location with predicted activity of the at least one CYP450-family enzyme;
associating the at least one anatomic location with one or more of the at least one modulator; and
invoking circuitry for communicating the at least one treatment to the system user, wherein the at least one treatment includes the at least one modulator of the at least one CYP450-family enzyme associated with the at least one anatomic location.

31. A system, comprising:
circuitry for accepting input relating to microbial infection associated with an individual;

circuitry for identifying at least one statin therapy, wherein the at least one statin therapy is associated with a reduction in the microbial infection;
circuitry for identifying at least one CYP450-family enzyme, wherein the at least one CYP450-family enzyme is associated with metabolism of the at least one statin therapy;
circuitry for identifying at least one modulator of the at least one CYP450-family enzyme; and
circuitry for communicating at least one treatment to a system user, wherein the at least one treatment includes the at least one statin therapy and the at least one modulator.

32. The system of claim 31, comprising:
circuitry for suggesting one or more dosages of the at least one treatment to the system user;
circuitry for identifying at least one environmental factor associated with an alteration in activity of the at least one treatment; and
circuitry for communicating one or more alternate dosages of the at least one treatment to the system user, wherein the one or more alternate dosages are calculated to compensate for the alteration in activity of the at least one treatment.

33. The system of claim 31, comprising:
circuitry for suggesting one or more dosages of the at least one treatment to the system user;
circuitry for identifying at least one dietary factor associated with an alteration in activity of the at least one treatment; and
circuitry for communicating one or more alternate dosages of the at least one treatment to the system user, wherein the one or more alternate dosages are calculated to compensate for the alteration in activity of at least one of the at least one treatment.

34. The system of claim 31, comprising:
circuitry for accepting input regarding at least one variant of the at least one CYP450-family enzyme associated with the individual;
circuitry for identifying at least one modulator of the at least one variant of the at least one CYP450-family enzyme; and
circuitry for communicating the at least one treatment to the system user, wherein the at least one treatment includes one or more of the at least one statin therapy and the at least one modulator of the at least one variant of the at least one CYP450-family enzyme.

35. The system of claim 31, comprising:
circuitry for accepting input regarding at least one variant of the at least one CYP450-family gene associated with the individual;
circuitry for identifying at least one modulator of the at least one variant of the at least one CYP450-family gene; and
circuitry for communicating the at least one treatment to the system user, wherein the at least one treatment includes one or more of the at least one statin therapy and the at least one modulator of the at least one variant of the at least one CYP450-family gene.

36. The system of claim 31, comprising:
circuitry for identifying at least one environmental factor associated with activity of the at least one CYP450-family enzyme;
circuitry for requesting information regarding one or more of the at least one environmental factor in relation to the individual to be treated; and
circuitry for communicating at least one environmental mitigation strategy to the system user.

37. The system of claim 35, wherein the at least one environmental factor is associated with the individual.

38. The system of claim 31, comprising:
circuitry for identifying at least one dietary factor associated with activity of the at least one CYP450-family enzyme;
circuitry for requesting information regarding one or more of the at least one dietary factor in relation to the individual to be treated; and
circuitry for communicating at least one dietary mitigation strategy to the system user.

39. The system of claim 38, wherein the at least one dietary factor is associated with the individual.

40. The system of claim 31, comprising:
associating at least one anatomic location with predicted activity of the at least one CYP450-family enzyme;
associating the at least one anatomic location with one or more of the at least one modulator; and
invoking circuitry for communicating the at least one treatment to the system user, wherein the at least one treatment includes the at least one modulator of the at least one CYP450-family enzyme associated with the at least one anatomic location.

41. A system comprising:
at least one computer program for use with at least one computer system and wherein the at least one computer program includes a plurality of instructions including but not limited to:
one or more instructions for accepting input that specifies an individual;
one or more instructions for accepting input that specifies at least one environmental exposure of the individual;
one or more instructions for identifying at least one toxin associated with the at least one environmental exposure;
one or more instructions for identifying at least one CYP450-family enzyme associated with metabolism of one or more of the at least one toxin;
one or more instructions for identifying at least one modulator of one or more of the at least one CYP450-family enzyme; and
one or more instructions for communicating one or more treatment to a system user, wherein the one or more treatment includes the at least one modulator of one or more of the at least one CYP450-family enzyme.

42. A system, comprising:
at least one computer program for use with at least one computer system and wherein the at least one computer program includes a plurality of instructions including but not limited to:
one or more instructions for accepting input relating to microbial infection associated with an individual;
one or more instructions for identifying at least one statin therapy, wherein the at least one statin therapy is associated with a reduction in the microbial infection;
one or more instructions for identifying at least one CYP450-family enzyme, wherein the at least one CYP450-family enzyme is associated with metabolism of the at least one statin therapy;
one or more instructions for identifying at least one modulator of the at least one CYP450-family enzyme; and
one or more instructions for communicating at least one treatment to a system user, wherein the at least one treatment includes the at least one statin therapy and the at least one modulator.

* * * * *